US008039211B2

(12) United States Patent
Brinkmann et al.

(10) Patent No.: US 8,039,211 B2

(45) Date of Patent: Oct. 18, 2011

(54) POLYMORPHISMS IN THE HUMAN GENE FOR THE MULTIDRUG RESISTANCE-ASSOCIATED PROTEIN 1 (MRP-1) AND THEIR USE IN DIAGNOSTIC AND THERAPEUTIC APPLICATIONS

(75) Inventors: Ulrich Brinkmann, Weilheim (DE); Sven Hoffmeyer, Eberfing (DE); Esther Mornhinweg, Weilheim (DE)

(73) Assignee: PGxHealth, LLC, Newton, MA (US)

(*) Notice: Subject to any disclaimer, the term of this patent is extended or adjusted under 35 U.S.C. 154(b) by 437 days.

(21) Appl. No.: 11/901,238

(22) Filed: Sep. 13, 2007

(65) Prior Publication Data

US 2009/0144841 A1 Jun. 4, 2009

Related U.S. Application Data

(63) Continuation of application No. 10/627,253, filed on Jul. 24, 2003, now abandoned, which is a continuation of application No. PCT/EP02/00796, filed on Jan. 25, 2002.

(30) Foreign Application Priority Data

Jan. 26, 2001 (EP) .................................... 01101651

(51) Int. Cl.
*C12Q 1/68* (2006.01)
*C12P 19/34* (2006.01)

(52) U.S. Cl. .......................... 435/6; 435/91.1; 435/91.2

(58) Field of Classification Search ........................ None
See application file for complete search history.

(56) References Cited

FOREIGN PATENT DOCUMENTS

| | | |
|---|---|---|
| WO | WO 94/29469 | 12/1994 |
| WO | WO 97/00957 | 1/1997 |

OTHER PUBLICATIONS

Zaman et al. PNAS USA 91:8822-8826, Sep. 1994.*
Cole et al. GenBank Accession L05628; GI: 292332; Mar. 29, 1993.*
Hacker et al. Gut 1997, vol. 40: 623-627.*
Leucentini. The Scientist, Dec. 20, 2004, p. 20.*
Mummidi et al. The Journal of Biological Chemistry, vol. 275, No. 25, 18946-18961, 2000.*
Juppner et al. Bone. vol. 17, No. 2, Supplement, p. 39S-42S, 1995.*
Rund et al. (Adv Exp Med Biol. 1999;457:71-5).*
Cole et al. (Science, vol. 258, Dec. 1992, pp. 1650-1654).*
Anderson, "Human Gene Therapy", *Science*, 256:808-813 (1992).
Bakos et al., "Functional Multidrug Resistance Protein (MRP1) Lacking the N-Terminal Transmembrane Domain," *Journal of Biological Chemistry*, 273(27):32167-32175 (1998).
Berry et al., "A Prototype Computer System for De Novo Protein Design," *Biochemical Society Transactions*, 2(4):1033-1036 (1994).
Bertz et al., "Use of In Vitro and In Vivo Data to Estimate the Likelihood of Metabolic Pharmacokinetic Interactions," *Clinical Pharmacokinetics*, 32(3):210-258 (1997).
Borst et al., "The Multidrug Resistance Protein Family," *Biochimica et Biophysica Acta*, 1461:347-357 (1999).
Borst et al., "A Family of Drug Transporters: The Multidrug Resistance-Associated Proteins," *Journal of National Cancer Institute*, 92(16):1295-1302 (2000).
Campling et al., "Expression of the *MRP* and *MDR1* Multidrug Resistance Genes in Small Cell Lung Cancer," *Clinical Cancer Research*, 3(1):115-122 (1997).
Chow et al. "Rising Incidence of Renal Cell Cancer in the United States," *JAMA*, 281(17):1628-1631 (1999).
Cole et al., "Multidrug resistance mediated by the ATP-binding cassette transporter protein MRP," *BioEssays*, 20(11):931-940 (1998).
Cole et al., "Pharmacological Characterization of Multidrug Resistant MRP-transfected Human Tumor Cells," *Cancer Research*, 54:5902-5910 (1994).
Database EMBL Online EBI; Seq ID No. 75, Database Accession No. AC026452, XP002217455 abstract (2000).
Database EMBL Online EBI; Database Accesion No. AC026452, Doe Joint Genome Institute: "Sequencing of Human Chromosome 16" XP002241553 for SEQ ID Nos. 171 and 172 Abstract (2000).
D'Hondt et al., "Retrovirus-Mediated Gene Transfer of the Multidrug Resistance-Associated Protein (MRP) cDNA Protects Cells from Chemotherapeutic Agents," *Human Gene Therapy*, 8(15):1745-1751 (1997). Dörner et al., "The Synthesis of Peptidomimetic Combinatorial Libraries Through Successive Amide Alkylations," *Bioorganic and Medicinial Chemistry*, 4(5):709-715 (1996).
Engel et al., "Prediction of CYP2D6-Mediated Polymorphic Drug Metabolism (Sparteine Type) Based on In Vitro Investigations," *Journal of Chromatography B: Biomedical Applications*, 678:93-103 (1996).
Evers et al., "Inhibitory Effect of the Reversal Agaents V-104, GF120918 and Pluronic L61 on MDR1 Pgp-, MRP1- and MR2-Mediated Transport," *British Journal of Cancer*, 83(3):366-374 (2000).

(Continued)

*Primary Examiner* — Juliet Switzer

(74) *Attorney, Agent, or Firm* — McCarter & English, LLP

(57) ABSTRACT

The present invention relates to a polymorphic MRP-1 polynucleotide. Moreover, the invention relates to genes or vectors comprising the polynucleotides of the invention and to a host cell genetically engineered with the polynucleotide or gene of the invention. Further, the invention relates to methods for producing molecular variant polypeptides or fragments thereof, methods for producing cells capable of expressing a molecular variant polypeptide and to a polypeptide or fragment thereof encoded by the polynucleotide or the gene of the invention or which is obtainable by the method or from the cells produced by the method of the invention. Furthermore, the invention relates to an antibody which binds specifically the polypeptide of the invention. Moreover, the invention relates to a transgenic non-human animal. The invention also relates to a solid support comprising one or a plurality of the above mentioned polynucleotides, genes, vectors, polypeptides, antibodies or host cells. Furthermore, methods of identifying a polymorphism, identifying and obtaining a pro-drug or drug or an inhibitor are also encompassed by the present invention. In addition, the invention relates to methods for producing of a pharmaceutical composition and to methods of diagnosing a disease. Further, the invention relates to a method of detection of the polynucleotide of the invention. Furthermore, comprised by the present invention are a diagnostic and a pharmaceutical composition. Even more, the invention relates to uses of the polynucleotides, genes, vectors, polypeptides or antibodies of the invention. Finally, the invention relates to a diagnostic kit.

5 Claims, 3 Drawing Sheets

OTHER PUBLICATIONS

Figure 1:
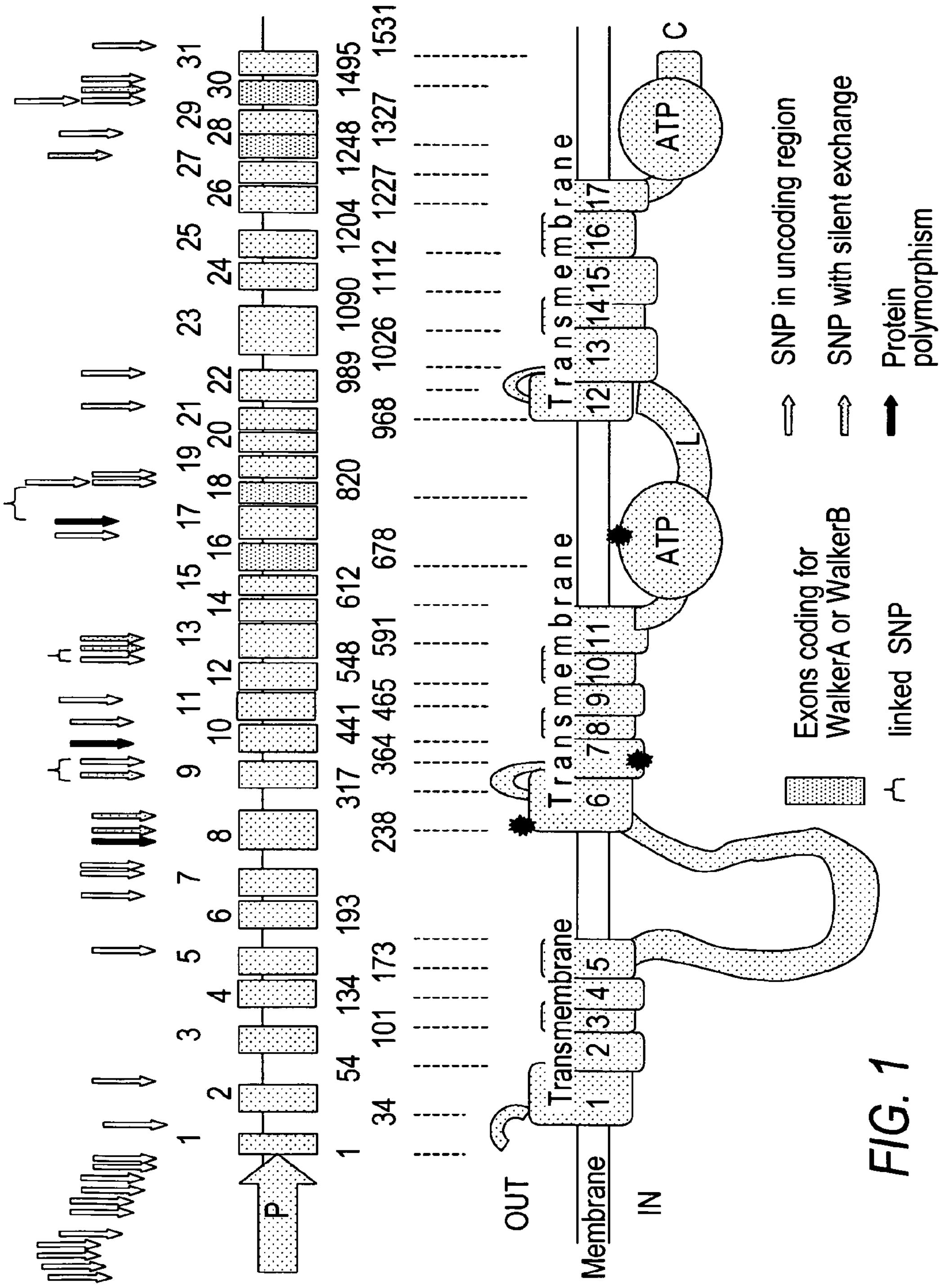

Fassina et al., "Identification of Interactive Sites of Proteins and Protein Receptors by Computer-Assisted Searches for Complementary Peptide Sequences," *Immunomethods*, 5:114-120 (1994).
Filipits et al., "Immunocytochemical Detection of the Multidrug Resistance-Associated Protein and P-Glycoprotein In Acute Myeloid Leukemia: Impact of Antibodies, Sample Source and Disease Status," *Leukemia*, 11(7):1073-1077 (1997).
Flens et al., "Immunochemical Detection of the Multidrug Resistance-Associated Protein MRP In Human Multidrug-Resistant Tumor Cells by Monoclonal Antibodies," *Cancer Research*, 54(17):4557-4563 (1994).
Galfrè et al., "Preparation of Monoclonal Antibodies: Strategies and Procedures," *Methods in Enzymology*, 73:3-46 (1981).
Giordano et al., "Intracoronary Gene Transfer of Fibroblast Growth Factor-5 Increases Blood Flow and Contractile Function in an Ischemic Region of the Heart," *Nature Medicine*, 2(5):534-539 (1996).
Grant et al., "Analysis of the Intron-Exon Organization of the Human Multidrug-Resistance Protein Gene (*MRP*) and Alternative Splicing of Its mRNA," *Genomics*, 45(2):368-378 (1997).
Heath et al., Hypertension, Diuretics, and Antihypertensive Medications as Possible Risk Factors for Renal Cell Cancer, *American Journal of Epidemiology*, 145(7):607-613 (1997).
Heijn et al., "Anthracyclines Modulate Multidrug Resistance Protein (MRP) Mediated Organic Anion Transport," *Biochimica et Biophysica Acta*, 1326: 12-22 (1997).
Hipfner et al., "Monoclonal Antibodies that Inhibit the Transport Function of the 190-kDa Multidrug Restistance Protein, MRP," *Journal of Biological Chemistry*, 274(22):15420-15426 (1999).
Hipfner et al., "Detection of the Mr190,000 Multidrug Resistance Protein, MRP, with Monoclonal Antibodies," *Cancer Research*, 54(22):5788-5792, 1994.
Hipfner et al., "Membrane Topology of the Multidrug Resistance Protein (MRP)," *Journal of Biological Chemistry*, 272(38):23623-23630 (1997).
Hipfner et al. "Structural, Mechanistic and Clinical Aspects of MRP1," *Biochimica et Biophysica Acta*, 1461:359-376 (1999).
Hoffman et al., "Rapid Protein Structure Classification Using One-Dimensional Structure Profiles on the Bioscan Parallel Computer," *CABIOS*, 11(6):675-679 (1995).
Hrycyna et al., Mechanism of Action of Human P-glycoprotein ATPase Activity,*Journal of Biological Chemistry*, 273(27):16631-16634 (1998).
Isner et al, "Clinical Evidence of Angiogenesis After Arterial Gene Transfer of phVEGF165 in Patient With Ischaemic Limb," *Lancet*, 348(10):370-374 (1996).
Jedlitschky et al., "ATP-Dependent Transport of Bilirubin Glucuronides by the Multidrug Resistance Protein MRP-1 and Its Hepatocyte Canalicular Isoform MRP2," *Biochemical Journal*, 327:305-310 (1997).
Jounaïdi et al., "Detection of a CYP3A5 Allelic Variant: A Candidate for the Polymorphic Expression of the Protein?," *Biochemical and Biophysical Research Communication*, 221:466-470 (1996).
Klein et al., "An Inventory of the Human ABC Proteins," *Biochimica et Biophysica Acta*, 1461:237-262 (1999).
Kohler et al., "Continuous Cultures of Fused Cells Secreting Antibody of Predefined Specificity," *Nature*, 256:495-497 (1975).
Levine, "Acquired Cystic Kidney Disease," *Radiologic Clinics of North America*, 34(5):947-964 (1996).
Linehan et al., "Identification of the Von Hippel-Lindau (VHL) Gene," *JAMA*, 273(7):564-570 (1995).
Loe et al., "ATP-Dependent Transport of Aflatoxin B1 and Its Glutathione Conjugates by the Product of the Multidrug Resistance Protein (MRP) Gene," *Molecular Pharmacology*, 51(6):1034-1041 (1997).
Loftus et al., "Genome Duplications and Other Features in 12 MB of DNA Sequence from Human Chromosome 16p and 16q," *Genomics*, 60(3):295-308 (1999).
Longuemaux et al., "Candidate Genetic Modifiers of Individual Susceptibility to Renal Cell Carcinoma: A Study of Polymorphic Human Xenobiotic-Metabolizing Enzymes," *Cancer Research*, 59:2903-2908 (1999).
Machiels et al., "Retrovirus-Mediated Gene Transfer of the Human Multidrug Resistance-Associated Protein into Hematopoietic Cells Protects Mice from Chemotherapy-Induced Leukopenia," *Human Gene Therapy*, 10(5): 801-811 (1999).
Malmborg et al., "BIAcore As a Tool in Antibody Engineering," *Journal of Immunological Methods*, 183:7-13 (1995).
Marshall, "Getting the Right Drug Into the Right Patient," *Nature Biotechnology*, 15(12):1249-1252 (1997).
Marshall, "Laying the Foundations For Personalized Medicines," *Nature Biotechnology*, 15(10):954-957 (1997).
Meyer et al., "Molecular Mechanisms of Genetic Polymorphisms of Drug Metabolism," *Annual Review of Pharmacology and Toxicology*, 37:269-296 (1997).
Meyer, "Overview of Enzymes of Drug Metabolism," *Journal of Pharmacokinetics and Biopharmaceutics*, 24(5):449-459 (1996).
Monge et al., "Computer Modeling of Protein Folding: Conformational and Energetic Analysis of Reduced and Detailed Proteins Models," *Journal of Molecular Biology*, 247(5):995-1012 (1995).
Mouellic et al., "Targeted Replacement of the Homeobox Gene *Hox-3.1* by the *Escherichia coli lacz* in Mouse Chimeric Embryos," *PNAS*, 87:4712-4716 (1990).
Mühlhauser et al., "VEGF165 Expressed by a Replication-Deficient Recombinant Adenovirus Vector Induces Angiogenesis In Vivo," *Circulation Research*, 77:1077-1086 (1995).
Nooter et al., "Molecular Mechanisms of Multidrug Resistance in Cancer Chemotherapy," *Pathology Research and Practice*, 192(7):768-780 (1996).
Norris et al., "Expression of the Gene For Multidrug-Resistance-Associated Protein and Outcome In Patients With Neuroblastoma," *New England Journal of Medicine*, 334(4):231-238 (1996).
Olszewski et al., "Folding Simulations and Computer Redesign of Protein A Three-Helix Bundle Motifs," *Proteins: Structure, Function, and Genetics*, 25(3):286-299 (1996).
Ostresh et al., "Generation and Use of Nonsupport-Bound Peptide and Peptidomimetic Combinatorial Libraries," *Methods in Enzymology*, 267:220-234 (1996).
Ozama, "Strategic Proposals for Avoiding Toxic Interactions With Drugs For Clinical Use During Development and After Marketing of a New Drug—Proposals For Designing Non-Clinical and Clinical Studies—Is the Non-Clinical Study Useful?," *Journal of Toxicological Sciences*, 21(5):323-329 (1996).
Pabo et al., "Computer-Aided Model-Building Strategies for Protein Design," *Biochemistry*, 25(20):5987-5991 (1986).
Perdu et al., "Identification of Novel Polymorphisms in the pM5 and MRP1 (ABCC1) Genes at Locus 16p13.1 and Exclusion of Both Genes as Responsible for Pseudozanthoma Elasticum," *Human Mutation*, 17(1):74-75 (2001).
Priebe et al., "Doxorubicin—and Daunorubicin-Glutathione Conjugates, but not Unconjugated Drugs, Competitively Inhibit Leukotriene C4 Transport Mediated by MRP/GS-X Pump," *Biochemical and Biophysical Research Communication*, 247(3):859-863 (1998).
Ramsay, "DNA Chips: State-of-the Art," *Nature Biotechnology*, 16:40-44 (1998).
Rao et al., "Choroid Plexus Epithelial Expression of *MDR1* P Glycoprotein and Multidrug Resistance-Associated Protein Contribute to the Blood-Cerebrospinal-Fluid Drug-Permeability Barrier," *PNAS*, 96:3900-3905 (1999).
Rappa et al., "New Insights into the Biology and Pharmacology of the Multidrug Resitance Protein (MRP) from the Gene Knockout Models," *Biochemical Pharmacology*, 58(4):557-562 (1999).
Renouf et al., "Molecular Modelling of Glycoproteins by Homology With Non-Glycosylated Protein Domains, Computer Simulated Glycosylation and Molecular Dynamics," *Glycoimmunology*, 376:37-45 (1995).
Rose et al., "Three-Dimensional Structures of HIV-1 and SIV Protease Product Complexes," *Biochemistry*, 35:12933-12944 (1996).
Ross et al., "High level multiplex genotyping by MALDI-TOF mass spectrometry," *Nature Biotechnology*, 16:1347-1351 (1998).

Rutenber et al., "A New Class of HIV-1 Protease Inhibitor: The Crystallographic Structure, Inhibition and Chemical Synthesis of an Aminimide Peptide Isostere," *Bioorganic and Medicinal Chemistry*, 4(9):1545-1558 (1996).
Schaper et al., "Molecular Mechanisms of Coronary Collateral Vessel Growth," *Circulation Research*, 79:911-919 (1996).
Schaper et al., "Therapeutic Targets in Cardiovascular Disorders," *Current Opinion in Biotechnology*, 7(6):635-640 (1996).
Schier et al., "Efficient In Vitro Affinity Maturation of Phage Antibodies Using Biacore Guided Selections," *Human Antibodies and Hybridomas*, 7(3):97-105 (1996).
Schlehofer et al., "International Renal-Cell-Cancer Study IV. The Role of Medical and Family History," *International Journal of Cancer*, 66(6):723-726 (1996).
Schneider et al., "ATP-Binding-Cassette (ABC) Transport Systems: Functional and Structural Aspects of the ATP-Hydrolyzing Subunits/Domains," *FEMS Microbiology Reviews*, 22:1-20 (1998).
Shimer et al., "Ligase Chain Reaction," *Methods in Molecular Biology*, 46:269-278 (1995).
Stewart et al., "Reduction of Expression of the Multidrug Resistance Protein (MRP) in Human Tumor Cells by Antisense Phosphorothioate Oligonucleotides," *Biochemical Pharmacology*, 51(4):461-469 (1996).
Stride et al., "Pharmacological Characterization of the Murine and Human Orthologs of Multidrug-Resistance Protein in Transfected Human Embryonic Kidney Cells," *Molecular Pharmacology*, 52:344-353 (1997).
Sullivan et al., "The Expression of Drug Resistance Gene Products During the Progressional of Human Prostrate Cancer," *Clinical Cancer Research*, 4(6):1393-1403 (1998).
Takebayashi et al., "The Expression of Multidrug Resistance Protein in Human Gastrointestinal Tract Carcinomas," *Cancer*, 82(4):661-666 (1998).
Ueda et al., "How Does P-Glycoprotein Recognize Its Substrates?," *Seminars in Cancer Biology*, 8(3):151-159 (1997).
Walker et al., "Distantly Related Sequences in the A- and B-Subunits of ATP Synthase, Myosin, Kinases and Other ATP-Requiring Enzymes and a Common Nucleotide Binding Fold," *The EMBO Journal*, 1(8):945-951 (1982).
Wang et al., "Second-Generation Adenovirus Vectors," *Nature Medicine*, 2(6):714-716 1996).
West et al, "Interpatient Variability: Genetic Predisposition and Other Genetic Factors," *Journal of Clinical Pharmacology*, 37(7):635-648 (1997).
Wijnholds et al., "Increased Sensitivity to Anticancer Drugs and Decreased Inflammatory Response in Mice Lacking the Multidrug Resistance-Associated Protein," *Nature Medicine*, 3(11):1275-1279 (1997).
Williams et al., "Introduction of Foreign Genes Into Tissues of Living Mice by DNA-Coated Microprojectiles," *PNAS*, 88:2726-2729 (1991).
Wingo et al., "Cancer Statistics, 1995," *CA—A Cancer Journal for Clinicians*, 45(1):8-30 (1995).
Wodak, "Computer-Aided Design in Protein Engineering," *Annals of the New York Academy of Science*, 501:1-13 (1987).
Yu et al., "Establishment and Characterization of Renal Cell Carcinoma Cell Lines With Multidrug Resistance," *Urology Research*, 28(2):86-92 (2000).
Zhang et al., "Glutathione-Related Mechanisms in Cellular Resistance to Anticancer Drugs (Review)," *International Journal of Oncology*, 12:871-882 (1998).
Zhu et al., "Functional Analysis of the Nucleotide Binding Domains of the Multidrug Resistance Protein (MRP)," *Oncology Research*, 9(5):229-236 (1997).
Japanese Single Nucleotide Polymorphisms (JSNP) Database, SNP Information for JSNP ID: IMS-JST094785 (2001).
Le Saux, O. et al., "Mutations in a gene encoding an ABC transporter cause pseudoxanthoma elasticum", *Nature Genetics*, vol. 25, pp. 223-227 (2000).
Marth, Gabor T., et al. "A general approach to single-nucleotide polymorphism discovery", *Nature Genetics*, Dec. 1999, vol. 23, pp. 452-456.
NCBI Single Nucleotide Polymorphism Database, SNP(ss) Details: ss39117 RefSNP(rs#) rs35587 (2000).
NCBI Single Nucleotide Polymorphism Database, SNP(ss) Details: ss39118 RefSNP (rs#) rs35588 (2000).
Taillon-Miller, P., et al., "Overlapping Genomic Sequences: A Treasure Trove of Single-Nucleotide Polymorphisms", *Genome Research*, vol. 8, pp. 748-754 (1998).

* cited by examiner

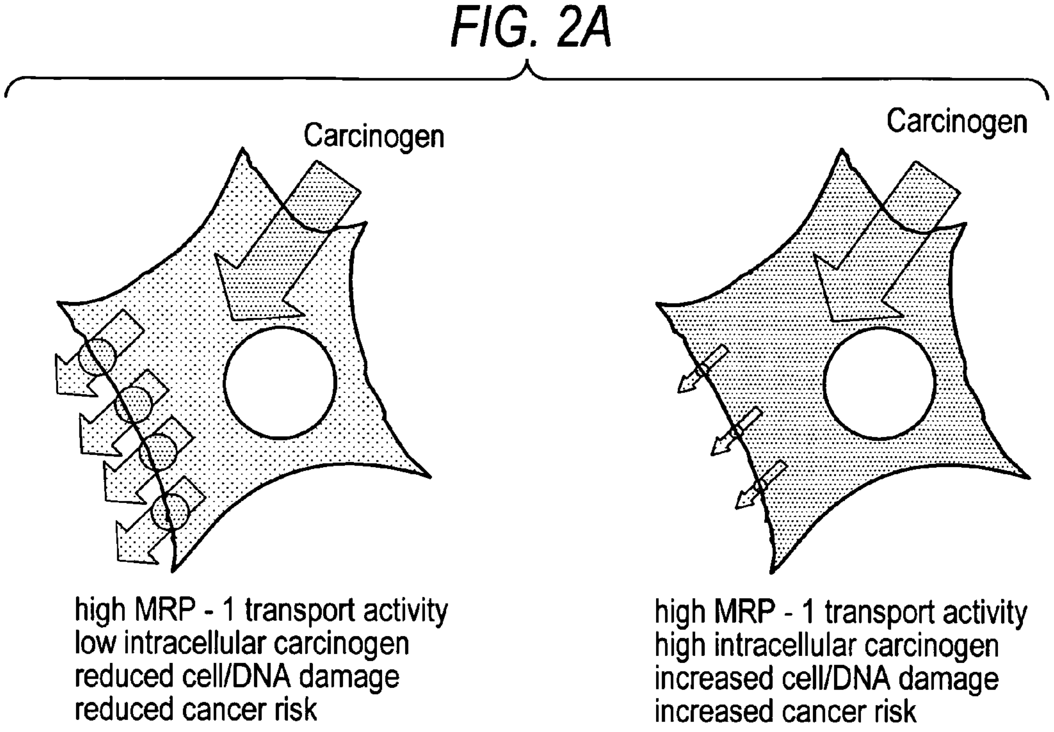

FIG. 2A high MRP - 1 transport activity
low intracellular carcinogen
reduced cell/DNA damage
reduced cancer risk high MRP - 1 transport activity
high intracellular carcinogen
increased cell/DNA damage
increased cancer risk

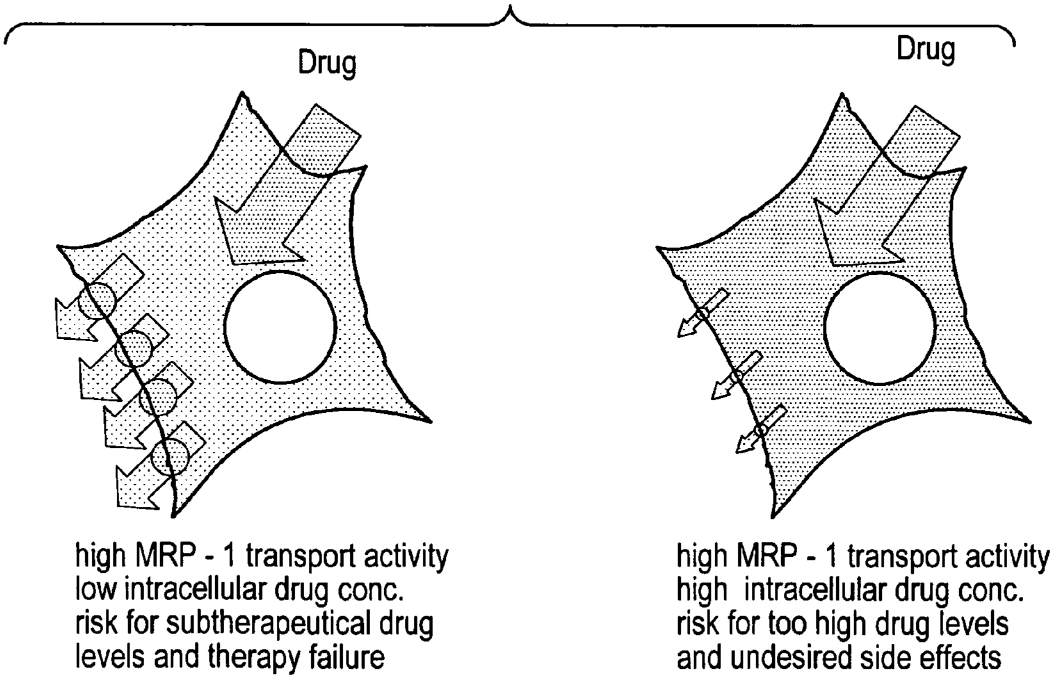

FIG. 2B high MRP - 1 transport activity
low intracellular drug conc.
risk for subtherapeutical drug
levels and therapy failure high MRP - 1 transport activity
high intracellular drug conc.
risk for too high drug levels
and undesired side effects

POLYMORPHISMS IN THE HUMAN GENE FOR THE MULTIDRUG RESISTANCE-ASSOCIATED PROTEIN 1 (MRP-1) AND THEIR USE IN DIAGNOSTIC AND THERAPEUTIC APPLICATIONS

This application is a continuation of U.S. patent application Ser. No. 10/627,253, filed Jul. 24, 2003, now abandoned, which is a continuation of international application PCT/EP02/00796, filed Jan. 25, 2002, which in turn, claims priority to EP Application No. 01101651.6, filed Jan. 26, 2001.

The present invention relates to a polymorphic MRP-1 polynucleotide. Moreover, the invention relates to genes or vectors comprising the polynucleotides of the invention and to a host cell genetically engineered with the polynucleotide or gene of the invention. Further, the invention relates to methods for producing molecular variant polypeptides or fragments thereof, methods for producing cells capable of expressing a molecular variant polypeptide and to a polypeptide or fragment thereof encoded by the polynucleotide or the gene of the invention or which is obtainable by the method or from the cells produced by the method of the invention. Furthermore, the invention relates to an antibody which binds specifically the polypeptide of the invention. Moreover, the invention relates to a transgenic non-human animal. The invention also relates to a solid support comprising one or a plurality of the above mentioned polynucleotides, genes, vectors, polypeptides, antibodies or host cells. Furthermore, methods of identifying a polymorphism, identifying and obtaining a pro-drug or drug or an inhibitor are also encompassed by the present invention. In addition, the invention relates to methods for producing of a pharmaceutical composition and to methods of diagnosing a disease. Further, the invention relates to a method of detection of the polynucleotide of the invention. Furthermore, comprised by the present invention are a diagnostic and a pharmaceutical composition. Even more, the invention relates to uses of the polynucleotides, genes, vectors, polypeptides or antibodies of the invention. Finally, the invention relates to a diagnostic kit.

The human multidrug resistance-associated protein (MRP) family, a subfamily of the ATP-binding cassette (ABC) protein superfamily, currently contains seven members. ABC proteins are composed of transmembrane domains (TMD's), and nucleotide binding domains (NBD's, or ATP-binding cassettes). The ability of several of these membrane proteins to transport a wide range of anticancer drugs out of cells and their expression in many tumor types, make them to possible candidates involved in unexplained cases of drug resistance (Borst et al. 2000, J Natl Cancer Inst 92 (16): 1295-1302; Borst et al. 1999, Biochimica et Biophysica Acta 1461: 347-357; Klein et al. 1999, Biochimica et Biophysica Acta 1461: 237-262).

One member of the human MRP family is MRP-1. The gene spans at least 200 kb and contains 31 exons. Several alternatively spliced variants of the MRP-1 mRNA could be characterized. The MRP-1 gene, encodes an integral membrane protein of 190 kDa whose function is the energy dependent export of substances from the inside of cells, and from membranes, to the outside. In contrast to P-glycoprotein that is invariably located in the apical membrane of epithelial cells, MRP-1 is located basolaterally and, therefore, tends to pump drugs into the body. The protein is present in many normal tissues and occurs mainly in lung, testis and muscle and very low in liver. The MRP-1 protein is located in plasma membranes in different tissues, like kidney and liver (Grant et al. 1997, Genomics 45: 368-378; Klein et al. 1999, Biochimica et Biophysica Acta 1461, 237-262; Cole and Deeley 1998, BioEssays 20: 931-940; Borst et al. 1999, Biochimica et Biophysica Acta 1461: 347-357). In addition it could be shown, that beside P-glycoprotein likewise MRP-1 is expressed in the epithelia of the choroid plexus (CP), in which the blood-cerebrospinal-fluid (CSF) drug permeability barrier is localized. The function of this blood-brain barrier is to isolate the brain from circulating drugs, toxins and xenobiotics. MRP-1 contributes to the basolateral broad-specificity drug-permeation barrier in CP (Rao et al. 1999, Proc. Natl. Acad. Sci. USA 96: 3900-3905).

In contrast to P-glycoprotein and to other members of the MRP family (MRP-4 and MRP-5), e.g. MRP-2 and MRP-1 possesses an additional N-terminal transmembrane domain (TMD0). Thus, these proteins contain two characteristic hydrophilic, cytosolic ATP-binding domains (NBD's) and 3 hydrophobic transmembrane domains, which include totally 17 transmembrane segments. This is designated as TMD0 (TMD-ABC)2 arrangement (Klein et al. 1999, Biochimica et Biophysica Acta 1461: 237-262). The NBD's are characterized by two sequence motifs, designated "Walker A" and "Walker B". Mutational analysis of a number of ABC proteins indicates that these two regions are critical for ATPase function (Walker et al. 1982, EMBO J. 1: 945-951; Schneider et al. 1998, FEMS Microbiol. Rev. 22: 1-20). Within the Walker A motif there exists a conserved lysine residue ($GX_4GKS/T$), which is essential in both nucleotide binding domains for full transport function. This is consistent with the role of this consensus sequence as the amino acid acceptor site of the phosphoryl moiety of the nucleotide. In addition, ABC transporters Pogsess a characteristic conserved "active transport family" signature (or "C") motif encompassing 14 amino acids ($LSSGGQX_3RHydXHydA$)(SEQ ID NO: 406). This region is located between the Walker A and B motifs. A possible significance of this motif referring to the binding and hydrolysis of nucleotide could be deduced from the observation, that it is highly conserved in NBD1, but not in NBD2 of the MRP-related proteins. This is in contrast to observations, which point to a invariant nature of this motif in NBD1 and NBD2 in P-glycoproteins (Cole and Deeley 1998, BioEssays 20: 931-940).

MRP-1 and the other members of the MRP family all contain a highly conserved "deletion" of 13 amino acids located between the Walker A and B motifs in NBD1, which alters the spacing between the two Walker motifs in the first nucleotide binding domain. Recent studies have shown, that this deletion affects the folding and activity of this domain (Hipfner et al. 1999, J. Biol. Chem. 274 (22): 15420-6). In contrast to the NBD's, the transmembrane domains of the ABC transporters are highly divergent. This sequence divergence is consistent with the notion that the transmembrane domains are important determinants of the different substrate specificities of various ABC transporters (Ueda et al. 1997, Semin. Cancer Biol. 8 (3): 151-159; Hrycyna et al. 1998, J. Biol. Chem. 273 (27): 16631-4). The study of post-translational modification of the MRP-1 protein by limited proteolysis and site-directed mutagenesis revealed, that the protein is glycosylated at Asn 19 and Asn 23 in the NH2-terminal transmembrane domain and at Asn 1006 in the COOH-proximal transmembrane domain (Hipfner et al. 1997, J. Biol. Chem. 272 (38): 23623-30). Interestingly, recent studies of deletion mutants of MRP-1, by the removal of the full TMD0 region, indicated that this region is neither required for the transport function of MRP-1 nor for its proper routing to the lateral plasma membrane compartment (Bakos et al. 1998, J. Biol. Chem. 273: 32167-32175).

The members of the MRP family transport anionic drugs, like methotrexate, neutral drugs conjugated to acidic ligands, such as glutathione (GSH), glucuronate, or sulfate. While for MRP-2 the major physiologic function is the transport of bilirubin glucuronides and other organic anions from liver into bile, for MRP-1 it is the transport of the cysteinyl leukotriene $LTC_4$. This is an important chemical mediator of inflammatory responses in receptor-mediated signal transduction pathways that control vascular permeability and smooth muscle contraction. So far no major physiologic function is known for the other members of the MRP family. MRP-1, -2 and -3 can additionally cause resistance to neutral organic drugs that are not known to be conjugated to acidic ligands by transporting these drugs together with free GSH (Borst et al. 2000, J Natl Cancer Inst 92 (16): 1295-1302; Hipfner et al. 1999, Biochimica et Biophysica Acta 1461: 359-376). Although MRP-1, MRP-2 and MRP-3 have many common substrates, the three transport proteins may differ in their relative affinities for individual compounds. $LTC_4$ remains the highest affinity substrate known for MRP-1. In addition to the cysteinyl leukotriene $LTC_4$ many of the identified endogenous MRP-1 substrates, like glutathione disulfide (GSSG) or bilirubin glucuronides are well characterized MRP-2 substrates (Heijn et al. 1997, Biochim. Biophys. Acta 1326: 12-22; Jedlitschky et al. 1997, Biochem. J. 327: 305-310). Beside $LTC_4$ the preferred substrates of MRP-1 are organic anions, like drugs conjugated to glutathione (GSH), glucuronate, or sulfate. MRP-1 transports for example substrates, such as methotrexate (MTX) or arsenite ($H_3AsO_3$). Likewise a variety of other GSH-conjugated xenobiotics, including conjugates of the activated forms of the potent carcinogen aflatoxin B1 can be actively transported by MRP-1, suggesting a protective role of MRP-1 in chemical carcinogenesis (Loe et al. 1997, Mol. Pharmacol. 51 (6): 1034-41). In contrast to that, P-glycoprotein has a low affinity for such negatively charged compounds.

Glutathione conjugation by GSTs and transport of glutathione S-conjugates out of cells into the extracellular space by MRP-1 have been shown to work as a system in the detoxification of many xenobiotics among them many anticancer drugs (Zhang et al., 1998, Int J One 12: 871-882). Because of that, the degree of expression and the functionality of the MRP-1 gene product can affect the therapeutic effectiveness of such agents. This is of particular importance in cancer therapy where high MRP-1, as well as P-gp expression and activity correlate With the resistance of cancer cells against chemotherapeutic drugs (Gottesman et al. 1996, Curr. Biol. 6: 610-617; Nooter and Stoter 1996, Path. Res. Pract. 192: 768-780).

Utilization of chemotherapy for the treatment of tumors can be limited by its hematological toxicity. Transduction of hematopoietic progenitors with the multidrug resistance 1 (MDR-1) or with the MRP-1 gene should provide protection from toxic effects of chemotherapeutic agents. The interest in the use of MRP-1 as an alternative to MDR-1 for bone marrow protection lies in its different modulation. Because MRP-1 expression is not reversed by agents, that decrease MDR-1 tumor resistance, these reversal agents can be used without reversing bone marrow (BM) protection of the MRP-1 transduced hematopoietic cells. These transduced cells have shown increased resistance to doxorubicin, vincristine and etoposide. In mice, a retrovirus-mediated MRP-1 gene transfer into hematopoietic cells leads to a protection from chemotherapy-induced leukopenia (Machiels et al. 1999, Hum Gene Ther 10 (5): 801-11; D'Hondt et al. 1997, Hum Gene Ther 8 (15): 1745-51).

For understanding the physiological mechanisms of action of MRP-1, such as mechanisms by which MRP-1 transports compounds and mediates multidrug resistance, mrp-1 knockout models in vitro, as well as in vivo have been generated (Wijnholds et al. 1997, Nat Med 3: 1275-1279). Because both the human and murine MRP-1 have an 88% amino acid identity and both can induce multidrug resistance when their respective cDNA's are transfected into drug-sensitive cells, it is conceivable that results from knockout studies can be transferred to humans (Stride et al. 1997, Mol Pharmacol 52: 344-353). A total block of the murine mrp-1 has been found to be compatible with life, suggesting that MRP-1 inhibitors can be safely used for treating cancer patients. The studies with mrp-1 knockout mice have given detailed insights in the MRP-1 transport characteristics, so that this protein catalyzes both the export of certain glutathione-S-conjugates and a cotransport of GSH and drugs or endogenous metabolites (Rappa et al. 1999, Biochem Pharmacol 58: 557-562).

Different forms of multidrug resistance (MDR) have been characterized. The classical MDR is defined by overexpression of P-glycoprotein, while the non-Pgp MDR phenotype has typically no expression of P-glycoprotein, but is caused by an overexpression of MRP-1. Such an overexpression has been observed so far in multidrug-resistant cell lines derived from many different tissue and tumor types, including both small cell and large cell lung cancer, carcinomas of the colon, breast, bladder, prostate, thyroid and cervix, glioma, neuroblastoma, fibrosarcoma, and various forms of leukemia (Hipfner et al. 1999, Biochimica et Biophysica Acta 1461: 359-376). Furthermore a cell line from renal cell carcinoma (RCC) could be established, which show resistance to adriamycin and epirubicin, in addition the cells demonstrated cross-resistance to cisplatin and 5-fluororubicin. Beside elevated MDR-1, GST-pi and topoisomerase II mRNA levels, likewise the mRNA content for MRP-1 was higher than in a control cell line (Yu et al. 2000, Urol. Res. 28 (2): 86-92). Multidrug resistance caused by MRP-1 and P-gp is characterized by an ATP-dependent reduction in drug accumulation. In respect to the drug resistance profiles of transfected cells, which overexpress P-gp or MRP-1 it could be shown that the substrate specificity of MRP-1 and P-glycoprotein is similar.

MRP-1 transfected mammalian cells are resistant to anthracyclines, such as doxorubicin and daunorubicin, to vinca alkaloids, such as vincristine and to the etoposide VP-16. The transfected cells accumulate lower levels of these drugs than do control cells (Zhu et al. 1997, Oncol. Res. 9: 229-236). In addition resistance to the vinca alkaloid vinblastine, to colchicine and to the taxane paclitaxel have been observed, but to a rather lower extent in MRP-1 transfected cells than in P-gp overexpressing cells. The basis of this differential sensitivity is still unknown. MRP-1 also confers resistance to certain antimonial and arsenical oxyanions (Cole et al. 1994, Cancer Res. 54: 5902-10).

Considerable interest exists in elucidating the potential involvement of MRP-1 in clinical MDR. For the analysis of the MRP-1 expression levels and its localization within both normal and malignant tissues, a number of different MRP-1 antibodies have been used in immunoassays (Flens et al. 1994, Cancer Res. 54 (17): 4557-63; Hipfner et al. 1994, Cancer Res. 54 (22): 5788-92). The expression of the MRP1 protein and/or mRNA has been detected in almost every tumor type examined. In the following some examples of the tumor types, which were analyzed: solid tumors, such as lung tumors, neuroblastoma, melanoma, retinoblastoma, breast and prostate cancer, as well as hematological malignancies (Takebayashi et al. 1998, Cancer 82 (4): 661-666; Campling et al. 1997, Clin. Cancer Res. 3 (1): 115-22; Sullivan et-al. 1998, Clin. Cancer Res. 4 (6): 1393-1403; Filipits et al. 1997, Leukemia 11 (7): 1073-7). Among the common tumor types, expression of high levels of MRP1 is particularly frequent in the major histologic forms of non-small cell lung cancer. These studies suggest that MRP1 may be involved in multidrug resistance of some tumor types or subgroups of patients, but up to now no comprehensive picture of the general relevance of this protein to clinical multidrug resistance has defined (Hipfner et al. 1999, Biochimica et Biophysica Acta 1461: 359-376).

Nevertheless several studies have detected MRP-1 expression levels to be of prognostic significance. In childhood neuroblastoma it could be shown, that the amplification of the N-myc oncogene is a powerful indicator of poor response to chemotherapy and poor outcome. The analysis of neuroblastoma tumor samples revealed significantly higher MRP-1 mRNA levels in tumors with N-myc amplification, than in tumors without such an amplification. In addition a correlation between levels of MRP-1 mRNA and a reduced survival rate independent of the N-myc amplification could be found (Norris et al. 1996, N. Engl. J. Med. 334 (4): 231-8).

The potential role of drug transporters in clinical multidrug resistance has lead to a search for strategies, which allow either an inhibition of these drug pumps, or a reduction of the expression in cancer patients. In respect to MRP's the attempts to find inhibitors have concentrated to MRP-1 and MRP-2. Examples of potent competitive inhibitors are high affinity substrates, such as leukotriene C4, S-decylglutathione and the leukotriene D4 anatgonist MK571. Other inhibitors are organic acids, such as probenecid and benzobromarone, which were originally developed to inhibit transport of uric acid (Borst et al. 2000, J Natl Cancer Inst 92 (16): 1295-1302). Furthermore experiments using polarized cell lines and ovarian carcinoma cells, both stably expressing MRP-1 cDNA have revealed, that V-104 (a pipecolinate derivative) partially inhibits daunorubicin transport by MRP-1. In addition this agent reverses etoposide resistance of MRP-1 expressing ovarian cancer cells (Evers et al. 2000, Br. J. Cancer 83 (3): 366-74). Another promising strategy for overcoming MRP-1 induced multidrug resistance is to use antisense oligonucleotides against this drug transporter. In MRP-1 transfected HeLa cells the treatment with an antisense oligonucleotide, targeted to the coding region of the MRP-1 mRNA results in a greater than 90% reduction of the MRP-1 mRNA level. Under these conditions an increased sensitivity to doxorubicin was observed (Stewart et al. 1996, Biochem. Pharmacol. 51 (4): 461-9). The findings concerning these two strategies have potential implications for the treatment of drug-resistant tumors.

Thus, means and methods for diagnosing and treating a variety of diseases and disorders based on dysfunctions or dysregulations of drug transport were not available yet but are nevertheless highly desirable. Thus, the technical problem underlying the present invention is to comply with the above specified needs.

The solution to this technical problem is achieved by providing the embodiments characterized in the claims.

Accordingly, the present invention relates to a polynucleotide comprising a polynucleotide selected from the group consisting of:

(a) a polynucleotide having the nucleic acid sequence of SEQ ID NO: 75, 76, 81, 82, 87, 88, 93, 94, 99, 100, 105, 106, 111, 112, 117, 118, 123, 124, 129, 130, 135, 136, 141, 142, 147, 148, 153, 154, 159, 160, 165, 166, 171, 172, 177, 178, 183, 184, 189, 190, 195, 196, 201, 202, 207, 208, 213, 214, 219, 220, 225, 226, 231, 232, 237, 238, 243, 244, 249, 250, 255, 256, 261, 262, 267, 268, 273, 274, 279, 280, 285, 286, 291, 292, 297, 298, 303, 304, 309, 310, 315, 316, 321, 322, 329, 330, 333, 334, 337, 338, 341, 342, 345, 346, 349, 350, 353, 354, 357, 358, 361, 362, 365, 366, 369, 370, 373, 374, 377, 378, 381, 382, 385, 386, 389, 390, 393, 394, 397 or 398;

(b) a polynucleotide encoding a polypeptide having the amino acid sequence of SEQ ID NO: 324, 326, 328, 401 or 403;

(c) a polynucleotide capable of hybridizing to a MRP-1 gene, wherein said polynucleotide is having a substitution or deletion of at least one nucleotide at a position corresponding to position 124667 of the MRP-1 gene (Accession No: AC026452), 1884, 1720 to 1723, 1163, 926, 437, 381, 233, 189, 440 or 1625 of the MRP-1 gene (Accession No: U07050), 39508 of the MRP-1 gene (GI No: 7209451), 79, 88 or 249 of the MRP-1 gene (Accession No: AF022830), 95 or 259 of the MRP-1 gene (Accession No: AF022831), 57998, 57853 or 53282 of the MRP-1 gene (GI No: 7209451), 137710, 137667, 38646 or 137647 of the MRP-1 gene (Accession No: AC026452), 27159, 27258, 34206 to 34207, 34218, 34215, 55156 or 55472 of the MRP-1 gene (Accession No: AC003026), 14008, 17970, 18195, 21133, 18067, 17900 of the MRP-1 gene (Accession No: U91318), or 150727 or 33551 of the MRP-1 gene (Accession No: AC025277), 174 of the MRP-1 gene (Accession No: AF022828), 248 or 258 of the MRP-1 gene (Accession No: AF022829), 51798 or 50892 of the MRP-1 gene (Accession No: GI 3582311), 37971 of the MRP-1 gene (Accession No: GI 7363401), 55296, 55132, 55114, 55112 or 20097 to 20099 of the MRP-1 gene (Accession No: GI 2815549), 109 to 122, 76 to 78, 73 to 78, 70 to 78, 67 to 78 or 58 to 78 of the MRP-1 gene (Accession No: GI 4826837), 60357, 61786 or 39541 of the MRP-1 gene (Accession No: GI 7209451) or a insertion of at least one nucleotide at a position corresponding to position 55156/55157 of the MRP-1 gene (Accession No: AC003026), 437/438 or 926/927 of the MRP-1 gene (Accession No: U07050) or 76437/76438 of the MRP-1 gene (Accession No: GI 7209451);

(d) a polynucleotide capable of hybridizing to a MRP-1 gene, wherein said polynucleotide is having at a position corresponding to position 124667 of the MRP-1 gene (Accession No: AC026452) a C, at a position corresponding to position 1884 of the MRP-1 gene (Accession No: U07050) a A, at a position corresponding to position 1720 to 1723 of the MRP-1 gene (Accession No: U07050) a deletion, at a position corresponding to position 1163 of the MRP-1 gene (Accession No: U07050) a T, at a position corresponding to position 926/927 of the MRP-1 gene (Accession No: U07050) a insertion, at a position corresponding to position 437/438 of the MRP-1 gene (Accession No: U07050) a insertion, at a position corresponding to position 381 of the MRP-1 gene (Accession No: U07050) a G, at a position corresponding to position 233 of the MRP-1 gene (Accession No: U07050) an A, at a position corresponding to position 189 of the MRP-1 gene (Accession No: U07050) an A, at a position corresponding to position 39508 of the MRP-1 gene (GI No: 7209451) an A, at a position corresponding to position 174 of the MRP-1 gene (Accession No: AF022828) a T, at a position corresponding to position 248 of the MRP-1 gene (Accession No: AF022829) an A, at a position corresponding to position 258 of the MRP-1 gene (Accession No: AF022829) a G, at a position corresponding to position 79 of the MRP-1 gene (Accession No: AF022830) an A, at a position corresponding to position 88 of the MRP-1 gene (Accession No: AF022830) a C, at a position corresponding to position 249 of the MRP-1 gene (Accession No: AF022830) a G, at a position corresponding to position 95 of the MRP-1 gene (Accession No: AF022831) a C, at apposition corresponding to position 259 of the MRP-1 gene (Accession No: AF022831) a G, at a position corresponding to position 57998 of the MRP-1 gene (GI No: 7209451) a T, at a position corresponding to position 57853 of the MRP-1 gene (GI. No: 7209451) a T, at a position corresponding to position 53282 of the MRP-1 gene (GI No: 7209451) a G, at a position corresponding to position 137710 of the MRP-1 gene (Accession No: AC026452) a G, at a position corresponding to position 137667 of the MRP-1 gene (Accession No: AC026452) a T, at a position corresponding to position 137647 of the MRP-1 gene (Accession No: AC026452) a T, at a position corresponding to position 27159 of the MRP-1 gene (Accession No: AC003026) a C, at a position corresponding to position 27258 of the MRP-1 gene (Accession No: AC003026) an A, at a position corresponding to position 34206 to 34207 of the MRP-1 gene (Accession No: AC003026) a deletion, at a position corresponding to position 34215 of the MRP-1 gene (Accession No: AC003026) a C, at a position corresponding to position 55156/55157 of the MRP-1 gene (Accession No: AC003026) a insertion, at a position corresponding to position 55472 of the MRP-1 gene (Accession No: AC003026) a C, at a position corresponding to position 14008 of the MRP-1 gene (Accession No: U91318) an A, at a position corresponding to position 150727 of the MRP-1 gene (Accession No: AC025277) an A, at a position corresponding to position 17970 of the MRP-1 gene (Accession No: U91318) a deletion, at a position corresponding to position 18195 of the MRP-1 gene (Accession No: U91318) an A, at a position corresponding to position 21133 of the MRP-1 gene (Accession No: U91318) an A, at a position corresponding to position 34218 of the MRP-1 gene (Accession No: AC003026) an A, at a position corresponding to position 18067 of the MRP-1 gene (Accession No: U91318) a T, at a position corresponding to position 440 of the MRP-1 gene (Accession No: U07050) a T, at a position corresponding to position 1625 of the MRP-1 gene (Accession No: U07050) an A, at a position corresponding to position 17900 of the MRP-1 gene (Accession No: U91318) a T, at a position corresponding to position 38646 of the MRP-1 gene (Accession No: AC026452) a C, at a position corresponding to position 33551 of the MRP-1 gene (Accession No: AC025277) an A, at a position corresponding to position 51798 of the MRP-1 gene (Accession No: 3582311) an G, at a position corresponding to position 37971 of the MRP-1 gene (Accession No: 7363401) an A, at a position corresponding to position 50892 of the MRP-1 gene (Accession No: 3582311) an A, at a position corresponding to position 55296 of the MRP-1 gene (Accession No: 2815549) an A, at a position corresponding to position 55132 of the MRP-1 gene (Accession No: 2815549) an A, at a position corresponding to position 55114 of the MRP-1 gene (Accession No: 2815549) an G, at a position corresponding to position 55112 of the MRP-1 gene (Accession No: 2815549) an G, at a position corresponding to position 109 to 122 of the MRP-1 gene (Accession No: 4826837) deletions, at a position corresponding to position 76 to 78 of the MRP-1 gene (Accession No: 4826837) deletions, at a position corresponding to position 73 to 78 of the MRP-1 gene (Accession No: 4826837) deletions, at a position corresponding to position 70 to 78 of the MRP-1 gene (Accession No: 4826837) deletions, at a position corresponding to position 67 to 78 of the MRP-1 gene (Accession No: 4826837) deletions, at a position corresponding to position 58 to 78 of the MRP-1 gene (Accession No: 4826837) deletions, at a position corresponding to position 20097 to 20099 of the MRP-1 gene (Accession No: 2815549) deletions, at a position corresponding to position 60357 of the MRP-1 gene (Accession No: 7209451) a T, at a position corresponding to position 61786 of the MRP-1 gene (Accession No: 7209451) an A, at a position corresponding to position 76437/76438 of the MRP-1 gene (Accession No: 7209451) an insertion or at a position corresponding to position 39541 of the MRP-1 gene (Accession No: 7209451) an A;

(e) a polynucleotide encoding an MRP-1 polypeptide or fragment thereof, wherein said polypeptide comprises an amino acid substitution at position 329, 433 or 723 of the MRP-1 polypeptide (Accession No: P33527) or 73 or 989 of the MRP-1 polypeptide (Accession No: GI 2828206); and (f) a polynucleotide encoding an MRP-1 polypeptide or fragment thereof, wherein said polypeptide comprises an amino acid substitution of Phe to Cys at position 329, Arg to Ser at position 433 or Arg to Gln at position 723 of the MRP-1 polypeptide (Accession No: P33527) or Thr to Ile at position 73 or Ala to Thr at position 989 of the MRP-1 polypeptide (Accession No: GI 2828206).

In the context of the present invention the term "polynucleotides" or the term "polypeptides" refers to different variants of a polynucleotide or polypeptide. Said variants comprise a reference or wild type sequence of the polynucleotides or polypeptides of the invention as well as variants which differ therefrom in structure or composition. Reference or wild type sequences for the polynucleotides are Accession No: U07050, AF022828, AF022829, AF022830, AF022831, AC026452, AC003026, U91318, AC025277 or GI No: 7209451. Reference or wild type sequence for the polypeptides of the invention is Accession No: P33527. The differences in structure or composition usually occur by way of nucleotide or amino acid substitution(s), addition(s) and/or deletion(s). Preferred deletions in accordance with the invention are a GGTA deletion at a position corresponding to position 1720 to 1723 of the MRP-1 gene (Accession No: U07050), an AT deletion at a position corresponding to position 34206 to 34207 of the MRP-1 gene (Accession No: AC003026) or a T deletion at a position corresponding to position 17970 of the MRP-1 gene (Accession No: U91318), preferred insertions are a TCCTTCC insertion at a position corresponding to position 437/438 of the MRP-1 gene (Accession No: U07050), a TGGGGC insertion at a position corresponding to position 55156/55157 of the MRP-1 gene (Accession No: AC003026) or a T insertion at a position corresponding to position 926/927 of the MRP-1 gene (Accession No: U07050). Preferably, said nucleotide substitution(s), addition(s) or deletion(s) comprised by the present invention result(s) in one or more changes of the corresponding amino acid(s) of the polypeptides of the invention. The variant polynucleotides and polypeptides also comprise fragments of said polynucleotides or polypeptides of the invention. The polynucleotides and polypeptides as well as the aforementioned fragments thereof of the present invention are characterized as being associated with a MRP-1 dysfunction or dysregulation comprising, e.g., insufficient and/or altered drug uptake. Said dysfunctions or dysregulations referred to in the present invention cause a disease or disorder or a prevalence for said disease or disorder. Preferably, as will be discussed below in detail, said disease is cancer or diseases related to multidrug resistance or any other disease caused by a dysfunction or dysregulation due to a polynucleotide or polypeptides of the invention, also referred to as MRP-1 gene associated diseases in the following.

The term "hybridizing" as used herein refers to polynucleotides which are capable of hybridizing to the polynucleotides of the invention or parts thereof which are associated with a MRP-1 dysfunction or dysregulation. Thus, said hybridizing polynucleotides are also associated with said dysfunctions and dysregulations. Preferably, said polynucleotides capable of hybridizing to the polynucleotides of the invention or parts thereof which are associated with MRP-1 dysfunctions or dysregulations are at least 70%, at least 80%, at least 95% or at least 100% identical to the polynucleotides of the invention or parts thereof which are associated with MRP-1 dysfunctions or dysregulations. Therefore, said polynucleotides may be useful as probes in Northern or Southern Blot analysis of RNA or DNA preparations, respectively, or can be used as oligonucleotide primers in PCR analysis dependent on their respective size. Also comprised by the invention are hybridizing polynucleotides which are useful for analysing DNA-Protein interactions via, e.g., electrophoretic mobility shift analysis (EMSA). Preferably, said hybridizing polynucleotides comprise at least 10, more preferably at least 15 nucleotides in length while a hybridizing polynucleotide of the present invention to be used as a probe preferably comprises at least 100, more preferably at least 200, or most preferably at least 500 nucleotides in length.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Molecular Cloning A Laboratory Manual, Cold Spring Harbor Laboratory (1989) N.Y. Preferred in accordance with the present inventions are polynucleotides which are capable of hybridizing to the polynucleotides of the invention or parts thereof which are associated with a MRP-1 dysfunction or dysregulation under stringent hybridization conditions, i.e. which do not cross hybridize to unrelated polynucleotides such as polynucleotides encoding a polypeptide different from the MRP-1 polypeptides of the invention.

The term "corresponding" as used herein means that a position is not only determined by the number of the preceding nucleotides and amino acids, respectively. The position of a given nucleotide or amino acid in accordance with the present invention which may be deleted, substituted or comprise one or more additional nucleotide(s) may vary due to deletions or additional nucleotides or amino acids elsewhere in the gene or the polypeptide. Thus, under a "corresponding position" in accordance with the present invention it is to be understood that nucleotides or amino acids may differ in the indicated number but may still have similar neighboring nucleotides or amino acids. Said nucleotides or amino acids which may be exchanged, deleted or comprise additional nucleotides or amino acids are also comprised by the term "corresponding position". Said nucleotides or amino acids may for instance together with their neighbors form sequences which may be involved in the regulation of gene expression, stability of the corresponding RNA or RNA editing, as well as encode functional domains or motifs of the protein of the invention.

By, e.g., "position 1720 to 1723" it is meant that said polynucleotide comprises one or more deleted nucleotides which are deleted between positions 1720 and position 1723 of the corresponding wild type version of said polynucleotide. The same applies mutatis mutandis to all other position numbers referred to in the above embodiment which are drafted in the same format.

By, e.g., "position 437/438" it is meant that said polynucleotide comprises one or more additional nucleotide(s) which are inserted between positions 437 and position 438 of the corresponding wild type version of said polynucleotide. The same applies mutatis mutandis to all other position numbers referred to in the above embodiment which are drafted in the same format, i.e. two consecutive position numbers separated by a slash (/).

In accordance with the present invention, the mode and population distribution of genetic variations in the MRP-1 gene has been analyzed by sequence analysis of relevant regions of the human said gene from many different individuals. It is a well known fact that genomic DNA of individuals, which harbor the individual genetic makeup of all genes, including the MRP-1 gene, can easily be purified from individual blood samples. These individual DNA samples are then used for the analysis of the sequence composition of the alleles of the MRP-1 gene that are present in the individual which provided the blood sample. The sequence analysis was carried out by PCR amplification of relevant regions of said genes, subsequent purification of the PCR products, followed by automated DNA sequencing with established methods (e.g. ABI dyeterminator cycle sequencing).

One important parameter that had to be considered in the attempt to determine the individual genotypes and identify novel variants of the MRP-1 gene by direct DNA-sequencing of PCR-products from human blood genomic DNA is the fact that each human harbors (usually, with very few abnormal exceptions) two gene copies of each autosomal gene (diploidy). Because of that, great care had to be taken in the evaluation of the sequences to be able to identify unambiguously not only homozygous sequence variations but also heterozygous variations. The details of the different steps in the identification and characterization of novel polymorphisms in the MRP-1 gene (homozygous and heterozygous) are described in the Examples below.

Over the past 20 years, genetic heterogeneity has been increasingly recognized as a significant source of variation in drug response. Many scientific communications (Meyer, Ann. Rev. Pharmacol. Toxicol. 37 (1997), 269-296 and West, J. Clin. Pharmacol. 37 (1997), 635-648) have clearly shown that some drugs work better or may even be highly toxic in some patients than in others and that these variations in patient's responses to drugs can be related to molecular basis. This "pharmacogenomic" concept spots correlations between responses to drugs and genetic profiles of patient's (Marshall, Nature Biotechnology, 15 (1997), 954-957; Marshall, Nature Biotechnology, 15 (1997), 1249-1252). In this context of population variability with regard to drug therapy, pharmacogenomics has been proposed as a tool useful in the identification and selection of patients which can respond to a particular drug without side effects. This identification/selection can be based upon molecular diagnosis of genetic polymorphisms by genotyping DNA from leukocytes in the blood of patient, for example, and characterization of disease (Bertz, Clin. Pharmacokinet. 32 (1997), 210-256; Engel, J. Chromatogra. B. Biomed. Appl. 678 (1996), 93-103). For the founders of health care, such as health maintenance organizations in the US and government public health services in many European countries, this pharmacogenomics approach can represent a way of both improving health care and reducing overheads because there is a large cost to unnecessary drugs, ineffective drugs and drugs with side effects.

The mutations in the variant genes of the invention sometime result in amino acid deletion(s), insertion(s) and in particular in substitution(s) either alone or in combination. It is of course also possible to genetically engineer such mutations in wild type genes or other mutant forms. Methods for introducing such modifications in the DNA sequence of said genes are well known to the person skilled in the art; see, e.g., Sambrook, Molecular Cloning A Laboratory Manual, Cold Spring Harbor Laboratory (1989) N.Y.

For the investigation of the nature of the alterations in the amino acid sequence of the polypeptides of the invention may be used such as BRASMOL that are obtainable from the Internet. Furthermore, folding simulations and computer redesign of structural motifs can be performed using other appropriate computer programs (Olszewski, Proteins 25 (1996), 286-299; Hoffman, Comput. Appl. Biosci. 11 (1995), 675-679). Computers can be used for the conformational and energetic analysis of detailed protein models (Monge, J. Mol. Biol. 247 (1995), 995-1012; Renouf, Adv. Exp. Med. Biol. 376 (1995), 37-45). These analysis can be used for the identification of the influence of a particular mutation on binding and/or transport of drugs.

Usually, said amino acid deletion, addition or substitution in the amino acid sequence of the protein encoded by the polynucleotide of the invention is due to one or more nucleotide substitution, insertion or deletion, or any combinations thereof. Preferably said nucleotide substitution, insertion or deletion may result in an amino acid substitution of F to C at position corresponding to position 329 of the MRP-1 polypeptide (Accession No: P33527), R to S at position corresponding to position 433 of the MRP-1 polypeptide (Accession No: P33527) or R to Q at position corresponding to position 723 of the MRP-1 polypeptide (Accession No: P33527). The polypeptides of encoded by the polynucleotides of the invention have altered biological or immunological properties due to the mutations referred to in accordance with the present invention. Examples for said altered properties are stability of the polypeptides which may be effected or an altered substrate specificity or an altered transport activity characterized by, e.g., insufficiencies in drug transport or a complete loss of the capability of transporting drugs.

The mutations in the MRP-1 gene detected in accordance with the present invention are listed in Table 2. The methods of the mutation analysis followed standard protocols and are described in detail in the Examples. In general such methods are to be used in accordance with the present invention for evaluating the phenotypic spectrum as well as the overlapping clinical characteristics of diseases or conditions related to dysfunctions or dysregulations and diseases related to impaired drug transport. Advantageously, the characterization of said mutants may form the basis of the development of improved drugs, such as drugs which are used in therapy of diseases related to multidrug resistance such as in cancer therapy. Said methods encompass for example haplotype analysis, single-strand conformation polymorphism analysis (SSCA), PCR and direct sequencing. On the basis of thorough clinical characterization of many patients the phenotypes can then be correlated to these mutations as well as to mutations that had been described earlier, for example in Jounaidi, Biochem Biophys Res Commun, 221, pp. 466-470, 1996.

Also comprised by the polynucleotides referred to in the present invention are polynucleotides which comprise at least two of the polynucleotides specified hereinabove, i.e. polynucleotides having a nucleotide sequence which contains at least two of the mutations comprised by the above polynucleotides or listed in Table 2 below. This allows the study of synergistic effects of said mutations in the MRP-1 gene and/or a polypeptide encoded by said polynucleotide on the pharmacological profile of drugs in patients who bear such mutant forms of the gene or similar mutant forms that can be mimicked by the above described proteins. It is expected that the analysis of said synergistic effects provides deeper insights into the onset of MRP-1 dysfunctions or dysregulations or diseases related to altered drug transport as described supra. From said deeper insight the development of diagnostic and pharmaceutical compositions related to MRP-1 dysfunctions or dysregulations or diseases related to altered drug transport will greatly benefit.

As is evident to the person skilled in the art, the genetic knowledge deduced from the present invention can now be used to exactly and reliably characterize the genotype of a patient. Advantageously, diseases or a prevalence for a disease which are associated with MRP-1 dysfunction or dysregulation, such as cancer or other multidrug resistance related diseases referred to herein can be predicted and preventive or therapeutical measures can be applied accordingly. Moreover in accordance with the foregoing, in cases where a given drug takes an unusual effect, a suitable individual therapy can be designed based on the knowledge of the individual genetic makeup of a subject with respect to the polynucleotides of the invention and improved therapeutics can be developed as will be further discussed below.

In general, the MRP-1 "status", defined by the expression level and activity of the MRP-1 protein, can be not only altered in many disease or disorders including cancer (see above), but can also be variable in normal tissue, due to genetic variations/polymorphisms. The identification of polymorphisms associated with altered MRP-1 expression and/or activity is important for the prediction of drug uptake and subsequently for the prediction of therapy outcome, including side effects of medications. Therefore, analysis of MRP-1 variations indicative of MRP-1 function, is a valuable tool for therapy with drugs, which are substrates of MRP-1 and has, thanks to the present invention, now become possible.

Finally, the polynucleotides and polypeptides referred to in accordance with the present invention are also useful as forensic markers, which improve the identification of subjects which have been murdered or killed by, for example a crime of violence or any other violence and can not be identified by the well known conventional forensic methods. The application of forensic methods based on the detection of the polymorphisms comprised by the polynucleotides of this invention in the genome of a subject are particularly well suited in cases where a (dead) body is disfigured in a severe manner such as identification by other body characteristics such as the features of the face is not possible. This is the case, for example, for corpses found in water which are usually entirely disfigured. Advantageously, methods which are based on the provision of the polynucleotides of the invention merely require a minimal amount of tissue or cells in order to be carried out. Said tissues or cells may be blood droplets, hair roots, epidermal scales, salivia droplets, sperms etc. Since only such a minimal amount of tissue or cells is required for the identification of a subject, the polymorphism comprised by the polynucleotides of this invention can also be used as forensic markers in order to proof someone guilty for a crime, such as a violation or a ravishment. Moreover, the polymorphisms comprised by the polynucleotides of this invention can be used to proof paternity. In accordance with the forensic methods referred herein the presence or absence of the polynucleotides of the invention is determined and compared with a reference sample which is unambiguously derived from the subject to be identified. The forensic methods which require detection of the presence or absence of the polynucleotides of this invention in a sample of a subject the polymorphisms comprised by the polynucleotides of this invention can be for example PCR-based techniques which are particularly well suited in cases where only minimal amount of tissue or cells is available as forensic samples. On the other hand, where enough tissue or cells is available, hybridization based techniques may be performed in order to detect the presence or absence of a polynucleotide of this invention. These techniques are well known by the person skilled in the art and can be adopted to the individual purposes referred to herein without further ado. In conclusion, thanks to the present invention forensic means which allow improved and reliable predictions as regards the aforementioned aspects are now available.

In line with the foregoing, preferably, the polynucleotide of the present invention is associated with a disease selected from the group of cancer diseases or multidrug resistance related diseases.

The term "cancer" used herein is very well known and characterized in the art. Several variants of cancer exist and are comprised by said term as meant in accordance with the invention. For a detailed list of symptoms which are indicative for cancer it is referred to text book knowledge, e.g. Pschyrembel.

More preferably, said cancer disease is kidney cancer, such as renal cell carcinoma (RCC). The meaning of renal cancer is explicitly disclosed in Example 4.

In a further embodiment the present invention relates to a polynucleotide which is DNA or RNA.

The polynucleotide of the invention may be, e.g., DNA, cDNA, genomic DNA, RNA or synthetically produced DNA or RNA or a recombinantly produced chimeric nucleic acid molecule comprising any of those polynucleotides either alone or in combination. Preferably said polynucleotide is part of a vector, particularly plasmids, cosmids, viruses and bacteriophages used conventionally in genetic engineering that comprise a polynucleotide of the invention. Such vectors may comprise further genes such as marker genes which allow for the selection of said vector in a suitable host cell and under suitable conditions.

The invention furthermore relates to a gene comprising the polynucleotide of the invention.

It is well known in the art that genes comprise structural elements which encode an amino acid sequence as well as regulatory elements which are involved in the regulation of the expression of said genes. Structural elements are represented by exons which may either encode an amino acid sequence or which may encode for RNA which is not encoding an amino acid sequence but is nevertheless involved in RNA function, e.g. by regulating the stability of the RNA or the nuclear export of the RNA.

Regulatory elements of a gene may comprise promoter elements or enhancer elements both of which could be involved in transcriptional control of gene expression. It is very well known in the art that a promoter is to be found upstream of the structural elements of a gene. Regulatory elements such as enhancer elements, however, can be found distributed over the entire locus of a gene. Said elements could be reside, e.g., in introns, regions of genomic DNA which separate the exons of a gene. Promoter or enhancer elements correspond to polynucleotide fragments which are capable of attracting or binding polypeptides involved in the regulation of the gene comprising said promoter or enhancer elements. For example, polypeptides involved in regulation of said gene comprise the so called transcription factors.

Said introns may comprise further regulatory elements which are required for proper gene expression. Introns are usually transcribed together with the exons of a gene resulting in a nascent RNA transcript which contains both, exon and intron sequences. The intron encoded RNA sequences are usually removed by a process known as RNA splicing. However, said process also requires regulatory sequences present on a RNA transcript said regulatory sequences may be encoded by the introns.

In addition, besides their function in transcriptional control and control of proper RNA processing and/or stability, regulatory elements of a gene could be also involved in the control of genetic stability of a gene locus. Said elements control, e.g., recombination events or serve to maintain a certain structure of the DNA or the arrangement of DNA in a chromosome.

Therefore, single nucleotide polymorphisms can occur in exons of a gene which encode an amino acid sequence as discussed supra as well as in regulatory regions which are involved in the above discussed process. The analysis of the nucleotide sequence of a gene locus in its entirety including, e.g., introns is in light of the above desirable. The polymorphisms comprised by the polynucleotides of the present invention can influence the expression level of MRP-1 protein via mechanisms involving enhanced or reduced transcription of the MRP-1 gene, stabilization of the gene's RNA transcripts and alteration of the processing of the primary RNA transcripts.

Therefore, in a furthermore preferred embodiment of the gene of the invention a nucleotide deletion, addition and/or substitution results in altered expression of the variant gene compared to the corresponding wild type gene.

In another embodiment the present invention relates to a vector comprising the polynucleotide of the invention or the gene of the invention.

Said vector may be, for example, a phage, plasmid, viral or retroviral vector. Retroviral vectors may be replication competent or replication defective. In the latter case, viral propagation generally will occur only in complementing host/cells.

The polynucleotides or genes of the invention may be joined to a vector containing selectable markers for propagation in a host. Generally, a plasmid vector is introduced in a precipitate such as a calcium phosphate precipitate, or in a complex with a charged lipid or in carbon-based clusters. Should the vector be a virus, it may be packaged in vitro using an appropriate packaging cell line prior to application to host cells.

In a more preferred embodiment of the vector of the invention the polynucleotide is operatively linked to expression control sequences allowing expression in prokaryotic or eukaryotic cells or isolated fractions thereof.

Expression of said polynucleotide comprises transcription of the polynucleotide, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells.

The term "isolated fractions thereof" refers to fractions of eukaryotic or prokaryotic cells or tissues which are capable of transcribing or transcribing and translating RNA from the vector of the invention. Said fractions comprise proteins which are required for transcription of RNA or transcription of RNA and translation of said RNA into a polypeptide. Said isolated fractions may be, e.g., nuclear and cytoplasmic fractions of eukaryotic cells such as of reticulocytes.

The present invention furthermore relates to a host cell genetically engineered with the polynucleotide of the invention, the gene of the invention or the vector of the invention.

Said host cell may be a prokaryotic or eukaryotic cell; see supra. The polynucleotide or vector of the invention which is present in the host cell may either be integrated into the genome of the host cell or it may be maintained extrachromosomally. In this respect, it is also to be understood that the recombinant DNA molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

The host cell can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as, for example, *E. coli, S. typhimurium, Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused, operably linked genes and expressing them in bacteria or animal cells are well-known in the art (Sambrook, supra). The genetic constructs and methods described therein can be utilized for expression of variant polypeptides of the invention in, e.g., prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The proteins of the invention can then be isolated from the grown medium, cellular lysates, or cellular membrane fractions. The isolation and purification of the microbially or otherwise expressed polypeptides of the invention may be by any conventional means such as, for example, preparative chromatographic separations and immunological separations such as those involving the use of monoclonal or polyclonal antibodies.

Thus, in a further embodiment the invention relates to a method for producing a molecular variant MRP-1 polypeptide or fragment thereof comprising culturing the above described host cell; and recovering said protein or fragment from the culture.

In another embodiment the present invention relates to a method for producing cells capable of expressing a molecular variant MRP-1 polypeptide comprising genetically engineering cells with the polynucleotide of the invention, the gene of the invention or the vector of the invention.

The cells obtainable by the method of the invention can be used, for example, to test drugs according to the methods described in D. L. Spector, R. D. Goldman, L. A. Leinwand, Cells, a Lab manual, CSH Press 1998. Furthermore, the cells can be used to study known drugs and unknown derivatives thereof for their ability to complement the deficiency caused by mutations in the MRP-1 gene. For these embodiments the host cells preferably lack a wild type allele, preferably both alleles of the MRP-1 gene and/or have at least one mutated from thereof. Ideally, the gene comprising an allele as comprised by the polynucleotides of the invention could be introduced into the wild type locus by homologous replacement. Alternatively, strong overexpression of a mutated allele over the normal allele and comparison with a recombinant cell line overexpressing the normal allele at a similar level may be used as a screening and analysis system. The cells obtainable by the above-described method may also be used for the screening methods referred to herein below.

Furthermore, the invention relates to a polypeptide or fragment thereof encoded by the polynucleotide of the invention, the gene of the invention or obtainable by the method described above or from cells produced by the method described above.

In this context it is also understood that the variant polypeptide of the invention can be further modified by conventional methods known in the art. By providing said variant proteins according to the present invention it is also possible to determine the portions relevant for their biological activity or inhibition of the same. The terms "polypeptide" and "protein" as used herein are exchangeable. Moreover, what is comprised by said terms is standard textbook knowledge.

The present invention furthermore relates to an antibody which binds specifically to the polypeptide of the invention.

Advantageously, the antibody specifically recognizes or binds an epitope containing one or more amino acid substitution(s) as defined above. Antibodies against the variant polypeptides of the invention can be prepared by well known methods using a purified protein according to the invention or a (synthetic) fragment derived therefrom as an antigen. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. In a preferred embodiment of the invention, said antibody is a monoclonal antibody, a polyclonal antibody, a single chain antibody, human or humanized antibody, primatized, chimerized or fragment thereof that specifically binds said peptide or polypeptide also including bispecific antibody, synthetic antibody, antibody fragment, such as Fab, Fv or scFv fragments etc., or a chemically modified derivative of any of these. Furthermore, antibodies or fragments thereof to the aforementioned polypeptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of the variant polypeptides of the invention as well as for the monitoring of the presence of said variant polypeptides, for example in recombinant organisms, and for the identification of compounds interacting with the proteins according to the invention. For example, surface plasmon resonance as employed in the BIAcore system can be used to increase the efficiency of phage antibodies which bind to an epitope of the protein of the invention (Schier, Human Antibodies Hybridomas 7 (1996), 97-105; Malmborg, J. Immunol. Methods 183 (1995), 7-13).

In a preferred embodiment the antibody of the present invention specifically recognizes an epitope containing one or more amino acid substitution(s) resulting from a nucleotide exchange as defined supra.

Antibodies which specifically recognize modified amino acids such as phospho-Tyrosine residues are well known in the art. Similarly, in accordance with the present invention antibodies which specifically recognize even a single amino acid exchange in an epitope may be generated by the well known methods described supra.

In light of the foregoing, in a more preferred embodiment the antibody of the present invention is monoclonal or polyclonal.

The invention also relates to a transgenic non-human animal comprising at least one polynucleotide of the invention, the gene of the invention or the vector of the invention as described supra.

The present invention also encompasses a method for the production of a transgenic non-human animal comprising introduction of a polynucleotide or vector of the invention into a germ cell, an embryonic cell, stem cell or an egg or a cell derived therefrom. The non-human animal can be used in accordance with the method of the invention described below and may be a non-transgenic healthy animal, or may have a disease or disorder, preferably a disease caused by at least one mutation in the gene of the invention. Such transgenic animals are well suited for, e.g., pharmacological studies of drugs in connection with variant forms of the above described variant polypeptides since these polypeptides or at least their functional domains are conserved between species in higher eukaryotes, particularly in mammals. Production of transgenic embryos and screening of those can be performed, e.g., as described by A. L. Joyner Ed., Gene Targeting, A Practical Approach (1993), Oxford University Press. The DNA of the embryos can be analyzed using, e.g., Southern blots with an appropriate probe or based on PCR techniques. A transgenic non-human animal in accordance with the invention may be a transgenic mouse, rat, hamster, dog, monkey, rabbit, pig, frog, nematode such as *Caenorhabditis elegans*, fruitfly such as *Drosophila melanogaster* or fish such as torpedo fish or zebrafish comprising a polynucleotide or vector of the invention or obtained by the method described above, preferably wherein said polynucleotide or vector is stably integrated into the genome of said non-human animal, preferably such that the presence of said polynucleotide or vector leads to the expression of the variant polypeptide of the invention. It may comprise one or several copies of the same or different polynucleotides or genes of the invention. This animal has numerous utilities, including as a research model for cardiovascular research and therefore, presents a novel and valuable animal in the development of therapies, treatment, etc. for diseases caused by cardiovascular diseases. Accordingly, in this instance, the mammal is preferably a laboratory animal such as a mouse or rat.

Thus, in a preferred embodiment the transgenic non-human animal of the invention is a mouse, a rat or a zebrafish.

Numerous reports revealed that said animals are particularly well suited as model organisms for the investigation of the drug metabolism and its deficiencies or cancer. Advantageously, transgenic animals can be easily created using said model organisms, due to the availability of various suitable techniques well known in the art.

The invention also relates to a solid support comprising one or a plurality of the polynucleotide, the gene, the vector, the polypeptide, the antibody or the host cell of the invention in immobilized form.

The term "solid support" as used herein refers to a flexible or non-flexible support that is suitable for carrying said immobilized targets. Said solid support may be homogenous or inhomogeneous. For example, said solid support may consist of different materials having the same or different properties with respect to flexibility and immobilization, for instance, or said solid support may consist of one material exhibiting a plurality of properties also comprising flexibility and immobilization properties. Said solid support may comprise glass-, polypropylene- or silicon-chips, membranes oligonucleotide-conjugated beads or bead arrays.

The term "immobilized" means that the molecular species of interest is fixed to a solid support, preferably covalently linked thereto. This covalent linkage can be achieved by different means depending on the molecular nature of the molecular species. Moreover, the molecular species may be also fixed on the solid support by electrostatic forces, hydrophobic or hydrophilic interactions or Van-der-Waals forces. The above described physico-chemical interactions typically occur in interactions between molecules. For example, biotinylated polypeptides may be fixed on a avidin-coated solid support due to interactions of the above described types. Further, polypeptides such as antibodies, may be fixed on an antibody coated solid support. Moreover, the immobilization is dependent on the chemical properties of the solid support. For example, the nucleic acid molecules can be immobilized on a membrane by standard techniques such as UV-crosslinking or heat.

In a preferred embodiment of the invention said solid support is a membrane, a glass- or poylpropylene- or silicon-chip, are membranes oligonucleotide-conjugated beads or a bead array, which is assembled on an optical filter substrate.

Moreover, the present invention relates to an in vitro method for identifying a polymorphism said method comprising the steps of:

(a) isolating a polynucleotide or the gene of the invention from a plurality of subgroups of individuals, wherein one subgroup has no prevalence for a MRP-1 associated disease and at least one or more further subgroup(s) do have prevalence for a MRP-1 associated disease; and
(b) identifying a polymorphism by comparing the nucleic acid sequence of said polynucleotide or said gene of said one subgroup having no prevalence for a MRP-1 associated disease with said at least one or more further subgroup(s) having a prevalence for a MRP-1 associated disease.

The term "prevalence" as used herein means that individuals are be susceptible for one or more disease(s) which are associated with MRP-1 dysfuntion or dysregulation or could already have one or more of said disease(s). Thereby, one MRP-1 associated disease can be used to determine the susceptibility for another MRP-1 associated disease, e.g. altered drug transport may be indicative for a prevalence for, e.g. cancer. Moreover, symptoms which are indicative for a prevalence for developing said diseases are very well known in the art and have been sufficiently described in standard textbooks such as Pschyrembel.

Advantageously, polymorphisms according to the present invention which are associated with MRP-1 dysfunction or dysregulation or one or more disease(s) based thereon should be enriched in subgroups of individuals which have a prevalence for said diseases versus subgroups which have no prevalence for said diseases. Thus, the above described method allows the rapid and reliable detection of polymorphism which are indicative for one or more MRP-1 associated disease(s) or a susceptibility therefor. Advantageously, due to the phenotypic preselection a large number of individuals having no prevalence might be screened for polymorphisms in general. Thereby, a reference sequences comprising polymorphisms which do not correlate to one or more MRP-1 associated disease(s) can be obtained. Based on said reference sequences it is possible to efficiently and reliably determine the relevant polymorphisms.

In a further embodiment the present invention relates to a method for identifying and obtaining a pro-drug or a drug capable of modulating the activity of a molecular variant of a MRP-1 polypeptide comprising the steps of:

(a) contacting the polypeptide, the solid support of the invention, a cell expressing a molecular variant gene comprising a polynucleotide of the invention, the gene or the vector of the invention in the presence of components capable of providing a detectable signal in response to drug activity with a compound to be screened for pro-drug or drug activity; and (b) detecting the presence or absence of a signal or increase or decrease of a signal generated from the pro-drug or the drug activity, wherein the absence, presence, increase or decrease of the signal is indicative for a putative pro-drug or drug.

The term "compound" in a method of the invention includes a single substance or a plurality of substances which may or may not be identical.

Said compound(s) may be chemically synthesized or produced via microbial fermentation but can also be comprised in, for example, samples, e.g., cell extracts from, e.g., plants, animals or microorganisms. Furthermore, said compounds may be known in the art but hitherto not known to be useful as an inhibitor, respectively. The plurality of compounds may be, e.g., added to the culture medium or injected into a cell or non-human animal of the invention.

If a sample containing (a) compound(s) is identified in the method of the invention, then it is either possible to isolate the compound from the original sample identified as containing the compound, in question or one can further subdivide the original sample, for example, if it consists of a plurality of different compounds, so as to reduce the number of different substances per sample and repeat the method with the subdivisions of the original sample. It can then be determined whether said sample or compound displays the desired properties, for example, by the methods described herein or in the literature (Spector et al., Cells manual; see supra). Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. The methods of the present invention can be easily performed and designed by the person skilled in the art, for example in accordance with other cell based assays described in the prior art or by using and modifying the methods as described herein. Furthermore, the person skilled in the art will readily recognize which further compounds may be used in order to perform the methods of the invention, for example, enzymes, if necessary, that convert a certain compound into a precursor. Such adaptation of the method of the invention is well within the skill of the person skilled in the art and can be performed without undue experimentation.

Compounds which can be used in accordance with the present invention include peptides, proteins, nucleic acids, antibodies, small organic compounds, ligands, peptidomimetics, PNAs and the like. Said compounds may act as agonists or antagonists of the invention. Said compounds can also be functional derivatives or analogues of known drugs. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art or as described. Furthermore, peptide mimetics and/or computer aided design of appropriate drug derivatives and analogues can be used, for example, according to the methods described below. Such analogs comprise molecules may have as the basis structure of known MRP-1 substrates and/or inhibitors and/or modulators; see infra.

Appropriate computer programs can be used for the identification of interactive sites of a putative inhibitor and the polypeptides of the invention by computer assistant searches for complementary structural motifs (Fassina, Immunomethods 5 (1994), 114-120). Further appropriate computer systems for the computer aided design of protein and peptides are described in the prior art, for example, in Berry, Biochem; Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used in combination with the method of the invention for, e.g., optimizing known inhibitors, analogs, antagonists or agonists. Appropriate peptidomimetics and other inhibitors can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of said compounds and the polypeptides of the invention can be used for the design of peptidomimetic drugs (Rose, Biochemistry 35 (1996), 12933-12944; Rutenber, Bioorg. Med. Chem. 4 (1996), 1545-1558). It is very well known how to obtain said compounds, e.g. by chemical or biochemical standard techniques. Thus, also comprised by the method of the invention are means of making or producing said compounds. In summary, the present invention provides methods for identifying and obtaining compounds which can be used in specific doses for the treatment of specific forms of MRP-1 associated diseases, e.g. dysfunctions or dysregulations of the drug transport such as cancer or multidrug resistance.

The above definitions apply mutatis mutandis to all of the methods described in the following.

In a further embodiment the present invention relates to a method for identifying and obtaining an inhibitor of the activity of a molecular variant of a MRP-1 polypeptide comprising the steps of:

(a) contacting the protein, the solid support of the invention or a cell expressing a molecular variant gene comprising a polynucleotide or the gene or the vector of the invention in the presence of components capable of providing a detectable signal in response to drug activity with a compound to be screened for inhibiting activity; and (b) detecting the presence or absence of a signal or increase or decrease of a signal generated from the inhibiting activity, wherein the absence or decrease of the signal is indicative for a putative inhibitor.

In a preferred embodiment of the method of the invention said cell is a cell, obtained by the method of the invention or can be obtained from the transgenic non-human animal as described supra.

In a still further embodiment the present invention relates to a method of identifying and obtaining a pro-drug or drug capable of modulating the activity of a molecular variant of a MRP-1 polypeptide comprising the steps of:

(a) contacting the host cell, the cell obtained by the method of the invention, the polypeptide or the solid support of the invention with the first molecule known to be bound by a MRP-1 polypeptide to form a first complex of said polypeptide and said first molecule;

(b) contacting said first complex with a compound to be screened, and (c) measuring whether said compound displaces said first molecule from said first complex.

Advantageously, in said method said measuring step comprises measuring the formation of a second complex of said protein and said inhibitor candidate. Preferably, said measuring step comprises measuring the amount of said first molecule that is not bound to said protein.

In a particularly preferred embodiment of the above-described method of said first molecule is a agonist or antagonist or a substrate and/or a inhibitor and/or a modulator of the polypeptide: of the invention, e.g., with a radioactive or fluorescent label.

In a still another embodiment the present invention relates to a method of identifying and obtaining an inhibitor capable of modulating the activity of a molecular variant of a MRP-1 polypeptide comprising the steps of:

(a) contacting the host cell or the cell obtained by the method of the invention, the protein or the solid support of the invention with the first molecule known to be bound by the MRP-1 polypeptide to form a first complex of said protein and said first molecule;

(b) contacting said first complex with a compound to be screened, and (c) measuring whether said compound displaces said first molecule from said first complex.

In a preferred embodiment of the method of the invention said measuring step comprises measuring the formation of a second complex of said protein and said compound.

In another preferred embodiment of the method of the invention said measuring step comprises measuring the amount of said first molecule that is not bound to said protein.

In a more preferred embodiment of the method of the invention said first molecule is labeled.

The invention furthermore relates to a method for the production of a pharmaceutical composition comprising the steps of the method as described supra; and the further step of formulating the compound identified and obtained or a derivative thereof in a pharmaceutically acceptable form.

The therapeutically useful compounds identified according to the methods of the invention can be formulated and administered to a patient as discussed above. For uses and therapeutic doses determined to be appropriate by one skilled in the art and for definitions of the term "pharmaceutical composition" see infra.

Furthermore, the present invention encompasses a method for the preparation of a pharmaceutical composition comprising the steps of the above-described methods; and formulating a drug or pro-drug in the form suitable for therapeutic application and preventing or ameliorating the disorder of the subject diagnosed in the method of the invention.

Drugs or pro-drugs after their in vivo administration are metabolized in order to be eliminated either by excretion or by metabolism to one or more active or inactive metabolites (Meyer, J. Pharmacokinet. Biopharm. 24 (1996), 449-459). Thus, rather than using the actual compound or inhibitor identified and obtained in accordance with the methods of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323-329).

In a preferred embodiment of the method of the present invention said drug or prodrug is a derivative of a medicament as defined hereinafter.

The present invention also relates to a method of diagnosing a disorder related to the presence of a molecular variant of the MRP-1 gene or susceptibility to such a disorder comprising determining the presence of a polynucleotide or the gene of the invention in a sample from a subject.

In accordance with this embodiment of the present invention, the method of testing the status of a disorder or susceptibility to such a disorder can be effected by using a polynucleotide gene or nucleic acid of the invention, e.g., in the form of a Southern or Northern blot or in situ analysis. Said nucleic acid sequence may hybridize to a coding region of either of the genes or to a non-coding region, e.g. intron. In the case that a complementary sequence is employed in the method of the invention, said nucleic acid molecule can again be used in Northern blots. Additionally, said testing can be done in conjunction with an actual blocking, e.g., of the transcription of the gene and thus is expected to have therapeutic relevance. Furthermore, a primer or oligonucleotide can also be used for hybridizing to one of the above mentioned MRP-1 gene or corresponding mRNAs. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence or expression of variant MRP-1 gene can be monitored by using a primer pair that specifically hybridizes to either of the corresponding nucleic acid sequences and by carrying out a PCR reaction according to standard procedures. Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual"

second ed., CSH Press, Cold Spring Harbor, 1989; "Nucleic Acid Hybridisation, A Practical Approach", Hames and Higgins eds., IRL Press, Oxford, 1985. Furthermore, the mRNA, cRNA, cDNA or genomic DNA obtained from the subject may be sequenced to identify mutations which may be characteristic fingerprints of mutations in the polynucleotide or the gene of the invention. The present invention further comprises methods wherein such a fingerprint may be generated by RFLPs of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments as described above. Further modifications of the above-mentioned embodiment of the invention can be easily devised by the person skilled in the art, without any undue experimentation from this disclosure; see, e.g., the examples. An additional embodiment of the present invention relates to a method wherein said determination is effected by employing an antibody of the invention or fragment thereof. The antibody used in the method of the invention may be labeled with detectable tags such as a histidine flags or a biotin molecule.

The invention relates to a method of diagnosing a disorder related to the presence of a molecular variant of a MRP-1 gene or susceptibility to such a disorder comprising determining the presence of a polypeptide or the antibody of the invention in a sample from a subject.

In a preferred embodiment of the above described method said disorder is a cancer disease or a disease related to multidrug resistance.

In a preferred embodiment of the present invention, the above described method is comprising PCR, ligase chain reaction, restriction digestion, direct sequencing, nucleic acid amplification techniques, hybridization techniques or immunoassays. Said techniques are very well known in the art.

Moreover, the invention relates to a method of detection of the polynucleotide or the gene of the invention in a sample comprising the steps of (a) contacting the solid support described supra with the sample under conditions allowing interaction of the polynucleotide or the gene of the invention with the immobilized targets on a solid support and;
(b) determining the binding of said polynucleotide or said gene to said immobilized targets on a solid support.

The invention also relates to an in vitro method for diagnosing a disease comprising the steps of the method described supra, wherein binding of said polynucleotide or gene to said immobilized targets on said solid support is indicative for the presence or the absence of said disease or a prevalence for said disease.

The invention furthermore relates to a diagnostic composition comprising the polynucleotide, the gene, the vector, the polypeptide or the antibody of the invention.

In addition, the invention relates to a pharmaceutical composition comprising the polynucleotide, the gene, the vector, the polypeptide or the antibody of the invention. These pharmaceutical compositions comprising, e.g., the antibody may conveniently be administered by any of the routes conventionally used for drug administration, for instance, orally, topically, parenterally or by inhalation. Acceptable salts comprise acetate, methylester, HCl, sulfate, chloride and the like. The compounds may be administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

Furthermore, the use of pharmaceutical compositions which comprise antisense-oligonucleotides which specifically hybridize to RNA encoding mutated versions of the polynucleotitde or gene according to the invention or which comprise antibodies specifically recognizing a mutated polypeptide of the invention but not or not substantially the functional wild-type form is conceivable in cases in which the concentration of the mutated form in the cells should be reduced.

Thanks to the present invention the particular drug selection, dosage regimen and corresponding patients to be treated can be determined in accordance with the present invention. The dosing recommendations will be indicated in product labeling by allowing the prescriber to anticipate dose adjustments depending on the considered patient group, with information that avoids prescribing the wrong drug to the wrong patients at the wrong dose.

In another embodiment the present invention relates to the use of the polynucleotide, the gene, the vector, the polypeptide the polynucleotides having at a position corresponding to position 926 of the MRP-1 gene (Accession No: U07050) a T insertion, at a position corresponding to position 79 of the MRP-1 gene (Accession No: AF022830) an A or at a position corresponding to position 137647 of the MRP-1 gene (Accession No: AC026452) a T, or at a position corresponding to position 150727 of the MRP-1 gene (Accession No: AC025277) an A, or the antibody of the invention for the preparation of a diagnostic composition for diagnosing a disease.

A gene encoding a functional and expressible polypeptide of the invention can be introduced into the cells which in turn produce the protein of interest. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813;

Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The gene may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

As is evident from the above, it is preferred that in the use of the invention the nucleic acid sequence is operatively linked to regulatory elements allowing for the expression and/or targeting of the polypeptides of the invention to specific cells. Suitable gene delivery systems that can be employed in accordance with the invention may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726-2729). Standard methods for transfecting cells with recombinant DNA are well known to those skilled in the art of molecular biology, see, e.g., WO 94/29469; see also supra. Gene therapy may be carried out by directly administering the recombinant DNA molecule or vector of the invention to a patient or by transfecting cells with the polynucleotide or vector of the invention ex vivo and infusing the transfected cells into the patient.

In a further embodiment the present invention relates to the use of the polynucleotide, the gene, the vector, the polypeptide the polynucleotides having at a position corresponding to position 926 of the MRP-1 gene (Accession No: U07050) a T insertion, at a position corresponding to position 79 of the MRP-1 gene (Accession No: AF022830) an A or at a position corresponding to position 137647 of the MRP-1 gene (Accession No: AC026452) a T, or at a position corresponding to position 150727 of the MRP-1 gene (Accession No: AC025277) an A, or the antibody of the invention for the preparation of a pharmaceutical composition for treating a disease.

In a more preferred embodiment of the use of the present invention said disease is cancer or a disease related to multidrug resistance.

Finally, the present invention relates to a diagnostic kit for detection of a single nucleotide polymorphism comprising the polynucleotide, the gene, the vector, the polypeptide, the antibody, the host cell, the transgenic non-human animal or the solid support of the invention.

The kit of the invention may contain further ingredients such as selection markers and components for selective media suitable for the generation of transgenic cells and animals. The kit of the invention can be used for carrying out a method of the invention and could be, inter alia, employed in a variety of applications, e.g., in the diagnostic field or as research tool. The parts of the kit of the invention can be packaged individually in vials or other appropriate means depending on the respective ingredient or in combination in suitable containers or multicontainer units. Manufacture of the kit follows preferably standard procedures which are known to the person skilled in the art. The kit may be used for methods for detecting expression of a mutant form of the polypeptides, genes or polynucleotides in accordance with any one of the above-described methods of the invention, employing, for example, immunoassay techniques such as radioimmunoassay or enzymeimmunoassay or preferably nucleic acid hybridization and/or amplification techniques such as those described herein before and in the Examples as well as pharmacokinetic studies when using non-human transgenic animals of the invention.

The figures illustrate the invention:

FIG. 1: The figure shows, where the novel MRP-1 SNP's are located on the gene and the protein, respectively.

FIG. 2: The figure illustrates the correlation between MRP-1 transport activity and (2A) intracellular carcinogen concentration and cancer risk, or (2B) intracellular drug concentration, therapy outcome and side effects.

Figure 3A:
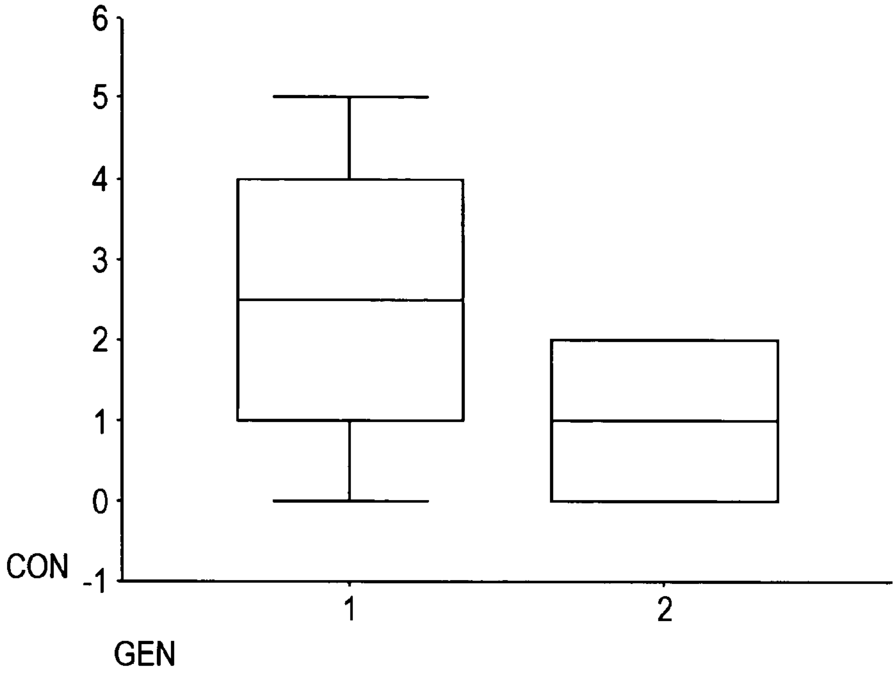
Figure 3B:
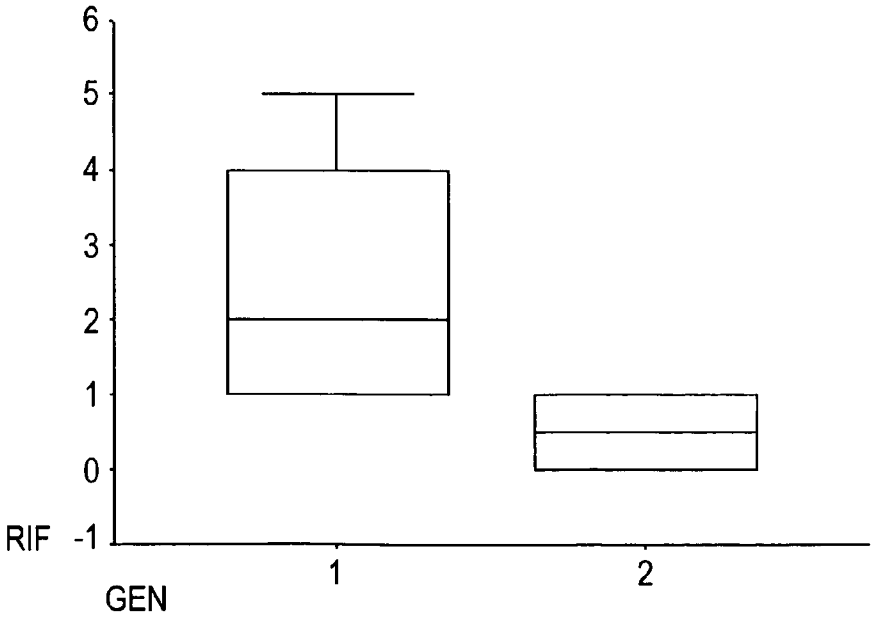

FIG. 3: Diagram 1A and 1B represent the correlation of the genotype (wt/wt: 1; wt/mut and mut/mut:2) with MRP-1 mRNA content in duodenal biopsies from healthy volunteers derived from two independent experiments, before (A) and after (B) application of rifampicin. The p-value of the statistical evaluation (Kruskal-Wallis-Test), which result in a genotyp/phenotype correlation is p=0.086. The p-value of the paired T-test ($p<0.001$) demonstrates, that rifampicin has no effect on MRP-1 mRNA expression. Thus, the differences in the MRP-1 mRNA content are based on interindividual differences. The statistical analyses were performed using the computer program SPSS 10.0 (SPSS, Chicago, USA).

The invention will now be described by reference to the following biological Examples which are merely illustrative and are not constructed as a limitation of the scope of the present invention.

EXAMPLE 1

Isolation of Genomic DNA from Human Blood, Generation and Purification of MRP-1 Fragments Genomic DNA was obtained by standard ion exchange chromatography techniques (Quiagen kits for isolation of genomic DNA from blood). Specific oligonucleotide primers, 2 for each fragment, were applied to obtain defined DNA fragments by polymerase chain reaction (PCR) containing specific parts of the MRP-1 gene. These specific oligonucleotide primers were designed to bind to sequences upstream and downstream of various exons of the gene. The resulting DNA fragments were to encode not only exon sequences, but also some intron sequences at the exon-intron boundaries. Such intronic sequences adjacent to the exons are known to be important for correct splicing and subsequent expression of the mRNA, which encodes for the respective protein. Oligonucleotide primer pairs that were optimized for each of the PCR fragments, synthesized and purified by affinity chromatography (OPC cartridges). The primer sequences for the amplification of the single fragments are listed in Table 1.

Polymerase chain reactions for the single MRP-1 gene fragments, were performed under conditions, that were optimized for each of these fragments. These MRP-1 gene fragments cover the respective exons, as well as regulatory regions, like promoter, 5'-UTR and 3'-UTR (see Table 1). PCRs were carried out for all fragments in a reaction volume of 50 μl. 40 ng DNA template was added to standard PCR buffer containing 1.5 mM MgCl2 (Qiagen, Hilden), 200 μM dNTP's (Roth, Karlsruhe), 0.4 μM (conditions A and C) or 1.6 μM (condition B) of each primer (Metabion, Munich), 10 μl Q-Solution (condition C; Qiagen, Hilden), 4 μl DMSO (condition B) and 1 U Taq polymerase (Qiagen, Hilden). All PCRs (conditions A and C) were performed on a Perkin Elmer thermocycler (model 9700) with an initial denaturation step of 2 min at 94° C. and 34 amplification cycles of denaturation at 94° C. for 45 sec, primer annealing at 62° C. for 45 sec, and 1 min for 72° C. followed by a final extension of 72° C. for 10 min. In the case of condition B the PCR reaction was performed with an initial denaturation step of 3 min at 96° C. and 35 amplification cycles of denaturation at 96° C. for 45 sec, primer annealing at 62° C. for 30 sec, and 1 min for 72° C. followed by a final extension of 72° C. for 10 min.

The optimized PCR-conditions and the resulting size of the desired and obtained fragments are listed in Table 1. The defined DNA fragments containing specific parts of the human MRP-1 gene were processed to remove nonincorporated nucleotides and buffer components that otherwise interfere with the subsequent determination of the individual MRP-1 genotype by direct DNA sequencing. For this purification, standard ion exchange chromatography techniques were used (Quiagen kits for PCR fragment purification). For all of the fragments, sufficient yields of purified fragments, suitable for direct DNA sequence analyses, were obtained.

EXAMPLE 2

Identification of Different MRP-1 Gene Alleles by Sequence Determination in Various Individuals For sequence analysis of relevant regions of the human MRP-1 gene from 24 different individuals, PCR amplification of the relevant fragments of this gene was carried out (see Table 1) and the purified PCR products subsequently sequenced with established methods (ABI dyeterminator cycle sequencing). A very important parameter that was needed to consider using this approach was that each normal human individual harbors two copies of this gene. Because of this diploidy (of autosomal genes; the MRP-1 gene is an autosomal gene on chromosome 16), great care had to be taken in the evaluation of the sequences to be able to identify unambiguously not only homozygous sequence variations but also heterozygous variations.

For the initial evaluation of gene variations in the human population, sequence analyses of the relevant regions of the MRP-1 gene were carried out from the genomic DNA from 24 different individuals. This number of individual samples was then extended for a screening for all the MRP-1 gene fragments, in which SNP's could be identified. The sequences were inspected for the occurrence of DNA sequences that were deviant from the published sequences of the MRP-1 gene. These reference sequences are considered as "wildtype" sequences in all of this work. Because population genetics enables a calculation of the expected frequency of homozygous vs. heterozygous alleles of a defined gene (Hardy-Weinberg distribution, using the formulas $p=(2\times AA+1\times Aa)/2N$ and $p+q=1$: AA=number of probands homozygous for the wt-allele, Aa=number of heterozygotes, N=size of the sample test, p=frequency of the wt-allele, q=frequency of the mut-allele, $q^2$=frequency of the genotype homozygous for the mut-allele), it was possible to confirm the predicted (using these formulas) distribution of homozygous vs. heterozygous alleles and deviations with the experimental findings (see Table 2). This serves as internal control and confirmation that a detected sequence deviation indeed represents a novel allele.

In total 42 new and still unpublished polymorphisms could be found in the MRP-1 gene. The localisation of these novel SNP's in the MRP-1 gene and in the MRP-1 protein, respectively, is shown in FIG. 1. 6 of all these new polymorphisms could be identified only in renal cell carcinoma (RCC) samples (see also example 4). The following table, gives an overview over all different types of novel MRP-1 polymorphisms, which have been identified in the initial screen (24 control samples, example 2), as well as in the extended screen, that includes clinical samples (70 RCC samples, see example 4):

| SNP location | Total number of newly found SNP's | comments |
|---|---|---|
| Promoter: | 11 | 2 SNP's in RCC samples only |
| Introns: | 20 | 2 SNP's in RCC samples only |
| Exons: total | 10 | |
| silent | 7 | 1 SNP in RCC samples only |
| amino acid substitution | 3 | R723Q (splicing variant region, first ATP binding domain)<br>R433S (cytoplasmic domain)<br>F329C (transmembrane domain no. 6; in RCC samples only) |
| 3'-UTR | 1 | |

In regard to the 42 newly found SNP's, the different types of polymorphisms that were detected, as well as their distribution over the MRP-1 gene and the possible meaning of the new SNP's are described in more detail below. The exact positions and further details of the novel alleles, including the exact novel sequence and sequence deviation, and the homozygous vs. heterozygous distribution of the respective allele in the population are listed in Table 2. The expected frequency for homozygotes of the variant allele were calculated on the basis of the Hardy-Weinberg distribution (formulas see above). The deviant base in the sequence is bold and underlined.

The polymorphisms newly found in the MRP-1 gene might have an effect either on the function of the MRP-1 polypeptide or its expression or translation. The promoter polymorphisms may especially affect the transcription level, while the SNP which was identified in the 3'-UTR might have an effect on the stability of the respective mRNA. Because the amino acid substitutions F329C, R433S and R723Q are localized in specific functional domains of the MRP-1 polypeptide (see above in the table), an effect of these SNP's on folding, activity or substrate specificity of the respective domains is conceivable. The single nucleotide polymorphisms resulting in silent mutations may effect interaction with a tRNA during translation of mRNA encoded by a gene comprising said single nucleotide polymorphisms. The polymorphisms, which could be found in the introns of the MRP-1 gene might have an effect on splicing of MRP-1 transcripts containing said single nucleotide polymorphisms.

The described single nucleotide polymorphisms are useful as e.g. diagnostic markers since they could be correlated with phenotypes resulting thereof, such as cancer, like kidney cancer. Furthermore the single nucleotide polymorphisms in MRP-1 may cause unsufficient and/or altered drug uptake, transport or elimination.

EXAMPLE 3

Methods for Specific Detection and Diagnosis of MRP-1 Alleles

Methods to detect the various MRP-1 alleles that have been identified utilize the principle that specific sequence differences can be translated into reagents for allele differentiation. These reagents provide the necessary backbone for the development of diagnostic tests. Examples for such reagents include—but are not limited to—oligonucleotides that deviate from the wildtype MRP-1 sequence in the newly identified base substitution. Frequently, the principles of diagnostic tests for the determination of the individual MRP-1 gene status include—but are not limited to—differences in the hybridization efficiencies of such reagents to the various MRP-1 alleles. In addition, differences in efficacy of such reagents in, or as different substrates for, enzymatic reactions, e.g. ligases or polymerases or restriction enzymes can be applied. The principles of these are well known to experts of the field. Examples are PCR- and LCR techniques, Chip-hybridizations or MALDI-TOF analyses. Such techniques are described in the prior art, e.g., PCR technique: Newton, (1994) PCR, BIOS Scientific Publishers, Oxford; LCR-technique: Shimer, Ligase chain reaction. Methods Mol. Biol. 46 (1995), 269-278; Chip hybridization: Ramsay, DNA chips: State-of-the art. Nature Biotechnology 16 (1998), 40-44; and MALDI-TOF analysis: Ross, High level multiplex genotyping by MALDI-TOF mass spectrometry, Nature Biotechnology 16 (1998), 1347-1351. Other test principles are based on the application of reagents that specifically recognize the MRP-1 variant as translated expressed protein. Examples are allele-specific antibodies, peptides, substrate analogs, inhibitors, or other substances which bind to (and in some instances may also modify the action of) the various MRP-1 protein forms that are encoded by the new MRP-1 alleles. The examples that are presented here, to demonstrate the principles of diagnostic tests with reagents derived from the novel nucleotide substitutions defined in this application, are based on PCR-methods. It is obvious that, applying the described specific reagents, any of the other methods will also work for the differentiation of MRP-1 alleles.

EXAMPLE 4

Distribution of MRP-1 Single Nucleotide Polymorphisms in Kidney Cancer Samples To identify potential direct correlations of MRP-1 polymorphisms with clinical relevant phenotypes in humans, totally 70 renal cell carcinoma (RCC) samples were subjected to the determination of MRP-1 polymorphisms as described in example 2. Kidney cancer is the third most frequent urological tumor, accounting in the United States for 28.000 cases in the year 1995 and approximately 11.000 deads each year in the US (Wingo et al. 1995, CA Cancer J Clin 45 (1): 8-30). One of the major risk factors for sporadic RCC are somatic mutations in the VHL tumor suppressor gene (Levine 1996, Radiol Clin North Am 34: 947-964; Linehan et al. 1995, JAMA 273: 564-570). The incidence of kidney cancer increases continuously by 2 to 4% per year in the United States and other industrialized countries (Chow et al. 1999, JAMA 281 (17): 1628-1631). These data support, that environmental factors, i.e. exposure to carcinogens, diuretic and antihypertensive drugs, tobacco smoke and dietary constituents may be involved in the occurence of RCC (Schlehofer et al. 1996, Int. J. Cancer 66: 723-726; Heath et al. 1997, Am. J. Epidemiol 145 (7): 607-613).

As excretory organs the kidneys are committed to the detoxification and excretion of carcinogens and metabolites. It is feasible to assume that factors or genes that play a role in the defense of kidney cells against dietary and environmental toxins or metabolites may influence the individual susceptibility towards RCC. Consequently, genetic polymorphisms in xenobiotic-metabolizing enzymes have been reported to modify RCC risk in the Caucasian population (Longuemaux et al. 1999, Cancer Res. 59: 2903-2908). Due to its role in detoxification, the gene for the human multidrug resistance-associated protein (MRP-1) may be another interesting candidate.

For the evaluation, if some of the newly found MRP-1 single nucleotide polymorphisms are overrepresented and underrepresented in these kidney cancer samples, respectively, the allele distribution was determined. The allele, as well as the genotype frequencies for all new MRP-1 polymorphisms distributed on the kidney cancer samples and in comparison to that distributed on control samples are listed in the following table.

| | | | | Frequency in % | | |
|---|---|---|---|---|---|---|
| | | Frequency in % | | | | Homozygotes mutant (expected |
| SNP | Sample collection | Wt-allele | Mut-allele | heterozygotes | Homozygotes mutant | Hardy Weinberg) |
| T124667C | Controls | 62.5 | 37.5 | 50 | 12.5 | 14.1 |
| (intron 1) | RCC | | | | | |
| G1884A | Controls | 93.3 | 6.7 | 13.3 | 0 | 0.5 |
| (Prom 1/exon 1) | RCC | | | | | |
| 1720- | Controls | 87.5 | 12.5 | 25 | 0 | 1.5 |
| 1723delGGTA (Prom 2) | RCC | 83.6 | 16.4 | 23.4 | 4.7 | 2.7 |
| C1163T | Controls | 91.3 | 8.7 | 17.4 | 0 | 0.7 |
| (Prom 3) | RCC | 84.5 | 15.5 | 27.7 | 1.7 | 2.4 |
| 926insT | Controls | 82.4 | 17.6 | 11.8 | 11.8 | 3.1 |
| (Prom 3) | RCC | 62.9 | 37.1 | 51.6 | 11.3 | 13.8 |
| 437insTCCTTCC | Controls | 97.6 | 2.4 | 4.8 | 0 | 0.1 |
| (Prom 4) | RCC | 96.3 | 3.7 | 7.4 | 0 | 0.1 |
| A381G | Controls | 72.7 | 27.3 | 36.4 | 9.1 | 7.4 |
| (Prom 5) | RCC | 61.5 | 38.5 | 50.8 | 13.1 | 14.8 |
| G233A | Controls | 84.8 | 15.2 | 30.4 | 0 | 2.3 |
| (Prom 5) | RCC | 77.9 | 22.1 | 34.4 | 4.9 | 4.9 |
| C189A | Controls | 95.7 | 4.3 | 8.7 | 0 | 0.2 |
| (Prom 5) | RCC | | | | | |

-continued

| SNP | Sample collection | Frequency in % Wt-allele | Mut-allele | Frequency in % heterozygotes | Homozygotes mutant | Homozygotes mutant (expected Hardy Weinberg) |
|---|---|---|---|---|---|---|
| G39508A (intron 2) | Controls | 93.5 | 6.5 | 13.04 | 0 | 0.4 |
| | RCC | 92.7 | 7.3 | 11.3 | 1.6 | 0.5 |
| C174T (intron 6) | Controls | 95.8 | 4.2 | 8.3 | 0 | 0.2 |
| | RCC | 100 | 0 | 0 | 0 | 0 |
| C248A (intron 7) | Controls | 79.2 | 20.8 | 25 | 8.3 | 4.3 |
| | RCC | 80 | 20 | 40 | 0 | 4 |
| C258G (intron 7) | Controls | 70.8 | 29.2 | 33.3 | 12.5 | 8.5 |
| | RCC | 71.8 | 28.2 | 45.5 | 5.5 | 7.9 |
| G79A (exon 8, Pro to Pro) | Controls | 93.7 | 6.3 | 12.5 | 0 | 0.4 |
| | RCC | 96.3 | 3.7 | 7.5 | 0 | 0.1 |
| T88C (exon 8, Val to Val) | Controls | 72.9 | 27.1 | 37.5 | 8.3 | 7.3 |
| | RCC | 71.3 | 28.7 | 42.6 | 7.4 | 8.2 |
| T249G (exon 8, Phe329Cys) | RCC (only in these samples) | 99.3 | 0.7 | 1.5 | 0 | 0.01 |
| *T95C (exon 9, Asn to Asn) | Controls | 71.7 | 28.3 | 39.1 | 8.7 | 7.9 |
| | RCC | 73.1 | 26.9 | 44.8 | 4.5 | 7.2 |
| *A259G (intron 9) | Controls | 71.7 | 28.3 | 39.1 | 8.7 | 7.9 |
| | RCC | 73.9 | 26.1 | 43.3 | 4.5 | 6.8 |
| G57998T (exon 10, Arg433Ser) | Controls | 96.9 | 3.1 | 6.3 | 0 | 0.1 |
| | RCC | 99.3 | 0.7 | 1.5 | 0 | 0.01 |
| C57853T (intron 10) | Controls | 97.9 | 2.1 | 4.2 | 0 | 0.1 |
| | RCC | 97.1 | 2.9 | 5.8 | 0 | 0.1 |
| C53282G (intron 11) | Controls | 77.1 | 22.9 | 37.5 | 4.2 | 5.3 |
| | RCC | 73.8 | 26.2 | 46.2 | 3.1 | 6.8 |
| *A137710G (intron 12) | Controls | 79.2 | 20.8 | 33.3 | 4.2 | 4.4 |
| | RCC | 81.5 | 18.5 | 29.6 | 3.7 | 3.4 |
| *C137667T (exon 13, Leu to Leu) | Controls | 79.2 | 20.8 | 33.3 | 4.2 | 4.4 |
| | RCC | 81.5 | 18.5 | 29.6 | 3.7 | 3.4 |
| C137647T (exon 13, Tyr to Tyr) | Controls | 85.4 | 14.6 | 29.2 | 0 | 2.1 |
| | RCC | 94.4 | 5.6 | 7.4 | 1.9 | 0.3 |
| *G27258A (exon 17, Arg723Gln) | Controls | 95.8 | 4.2 | 8.3 | 0 | 0.2 |
| | RCC | 96.2 | 3.8 | 7.7 | 0 | 0.2 |
| *34207delAT (intron 18) | Controls | 95.8 | 4.2 | 8.3 | 0 | 0.2 |
| | RCC | 96.3 | 3.7 | 7.4 | 0 | 0.1 |
| G34215C (intron 18) | Controls | 84.8 | 15.2 | 30.4 | 0 | 2.3 |
| | RCC | 84.3 | 15.7 | 25.7 | 2.9 | 2.5 |
| 55156insTGGGC (intron 21) | Controls | 75 | 25 | 0 | 25 | 6.3 |
| | RCC | 77.6 | 22.4 | 0 | 22.4 | 5.03 |
| T55472C (intron 22) | Controls | 83.3 | 16.7 | 8.3 | 12.5 | 2.8 |
| | RCC | 78.6 | 21.4 | 10.7 | 16.1 | 4.6 |
| G14008A (exon 28, Ser to Ser) | Controls | 80.4 | 19.6 | 39.1 | 0 | 3.8 |
| | RCC | 73.3 | 26.7 | 44.2 | 4.7 | 7.2 |
| G150727A (intron 28) | Controls | 66.7 | 33.3 | 50 | 8.3 | 10.9 |
| | RCC | 55 | 45 | 44.3 | 22.9 | 20.3 |
| 17970delT (intron 29) | Controls | 75 | 25 | 41.7 | 4.2 | 6.3 |
| | RCC | 75.7 | 24.3 | 34.3 | 7.2 | 5.9 |
| G18195A (intron 30) | Controls | 73.3 | 26.7 | 40 | 6.7 | 7.1 |
| | RCC | 80.4 | 19.6 | 21.7 | 8.7 | 3.8 |
| G21133A (3' flanking region) | Controls | 97.9 | 2.1 | 4.2 | 0 | 0.1 |
| | RCC | 95.7 | 4.3 | 8.7 | 0 | 0.2 |
| G38646C (Prom 1) | Controls | 73.3 | 26.7 | 53.3 | 0 | 7.1 |
| | RCC | | | | | |
| G34218A (intron 18) | RCC (only in these samples) | 96.3 | 3.7 | 7.4 | 0 | 0.1 |

-continued

| SNP | Sample collection | Frequency in % Wt-allele | Mut-allele | Frequency in % heterozygotes | Homozygotes mutant | Homozygotes mutant (expected Hardy Weinberg) |
|---|---|---|---|---|---|---|
| C18067T (exon 30, Ala to Ala) | RCC (only in these samples) | 98.9 | 1.1 | 2.2 | 0 | 0.02 |
| C440T (Prom 5) | RCC (only in these samples) | 99.3 | 0.7 | 1.5 | 0 | 0.01 |
| C1625A (prom 2) | RCC (only in these samples) | 96.9 | 3.1 | 6.3 | 0 | 0.1 |
| C17900T (intron 29) | RCC (only in these samples) | 97.9 | 2.1 | 4.3 | 0 | 0.1 |

Three pairs of linked polymorphisms are listed in this table, whereas each SNP is marked by an asterics. In regard to their under- and overrepresentation in the RCC samples in comparison to the control samples, respectively, all of the new single nucleotide polymorphisms are of great interest, because they represent genetic variety in humans, which may serve as potential targets for diagnosis and therapy and as risk factors for kidney cancer. Some examples: in contrast to the control samples the mutant alleles of 4 promoter SNP's found in the MRP-1 gene (C1163T (Prom 3), 926insT (Prom 3), A381G (Prom 5) and G233A (Prom 5)) are overrepresented in the RCC sample group. Likewise some of the new intron SNP's, like G150727A (intron 28) and T55472C (intron 22), as well as the silent mutation G14008A (exon 28, Ser to Ser) show allele distributions, which point to correlation with kidney cancer. In addition, especially the 6 SNP's, which could be only detected in the RCC samples may have an impact for the diagnosis and therapy of kidney cancer.

EXAMPLE 5

Statistical Analyses of Correlations Between MRP-1 Single Nucleotide Polymorphisms and Renal Cell Carcinoma (RCC)

Statistical evaluations were performed in regard to the presence of SNP's in RCC samples compared to their frequencies in a control population. For this purpose, 70 RCC samples and 24 control samples were compared. Statistical analysis was performed using the computer programm SPSS 10.0 (SPSS, Chicago, USA). This evaluation results in statistically significant correlations of definite SNP's with the existence of renal cell carcinoma (RCC).

The p-values of the statistical evaluation (Chi-Quadrat-Test), which result in genotype/phenotype correlations are:

| gene | SNP | Controls vs. RCC, p-value |
|---|---|---|
| MRP-1 | 926insT (Promoter) | 0.005 |
| | G79A (exon 8) | 0.063 |
| | C137647T (exon 13) | 0.039 |

EXAMPLE 6

Effects of Kidney Cancer Associated MRP-1 Polymorphisms on Drug Transport Activity and Pharmacology As excretory organs the kidneys are committed to the detoxification and excretion of watersoluble carcinogens and metabolites. Therefore, factors or genes that influence the individual susceptibility towards kidney cancer are related to the defense capacity of kidney cells against dietary and environmental toxins or metabolites (Epidauros MDR-1 risk factor patent). Among these factors, the gene for the P-glycoprotein (Pgp), which transports toxic substances, has been shown to confer a significant risk factor for kidney cancer, such as for RCC, if it is present in an allelic version that corresponds to low transport activity (Epidauros MDR-1 risk factor patent).

The multidrug resistance-associated protein 1 (MRP-1) is, like MDR-1 expressed in the renal tubular cells of the kidney and extrude different classes of substances in an ATP dependent manner from the inside to the outside of plasma membranes within these cells. The physiological role of this energy-dependent export mechanism in the kidney is the protection of cells. The fact that, like MDR-1 SNP's, also polymorphisms in the MRP-1 gene (which has a very similar function) confer significantly increased risk to develop kidney cancer, such as RCC (see tables in examples 2, 4 and the results of the statistical evaluation in example 5, respectively), indicates the underlying molecular mechanism to be the same for the functional polymorphisms in MDR-1 as well as in MRP-1: altered and/or reduced transport capacities lead to increased exposure of renal cells to carcinogenic, toxic and/or noxic substances, which is responsible for the increased risk to develop malignant changes in tubular cells.

Beside the Promoter SNP 926insT, which shows a statistically significant correlation with RCC (p=0.005), also the following MRP-1 promoter SNP's C1163T, A381G and G233A, which are overrepresented in RCC are good candidates for such risk factors.

Variable transport capacities of MRP-1-variants play a role not only in influencing the individual risk of developing kidney cancer, such as RCC, but such variations will also affect individual pharmacological responses to medications. For example, the expression of MRP-1 correlates with therapy outcome in cancer therapy: Higher MRP-1 activity leads to a resistance of the cell against MRP-1 substrates. This multidrug resistance could be shown for numerous MRP-1 substrates.

Therefore, MRP-1 polymorphisms, especially those with functional importance, even up to a degree that associated with increased risk for kidney cancer, such as RCC due to a decreased capacity of tubular cells to clear damaging agents, are important for predicting clearance and uptake of MRP-1 substrates, or drugs whose metabolites are MRP-1 substrates (see FIGS. 2 A and B).

EXAMPLE 7

Correlation of MRP-1 Polymorphisms with MRP-1 Expression and Side Effects During Therapy with MRP-1 Substrates Functional polymorphisms in the MRP-1 gene (see tables in examples 2 and 4) affect the transport activity and subsequently the levels of drugs which are substrates of MRP-1. Increased levels of such drugs can lead to side effects whereas decreased levels may result in subtherapeutical drug levels that lead to therapy failure. Three different patient collectives, two show side effects during drug therapy and one for which the MRP-1 mRNA levels had been defined, were analyzed to determine whether MRP-1 polymorphisms correlate with transporter activity and subsequently with alterations in drug activities and side effects. Statistical evaluations were performed in regard to the presence of SNP's in these collectives with side effects during drug therapy and increased/decreased mRNA levels compared to their frequencies in control samples. For this purpose, the 3 collectives (collective 1: samples with nephrotoxicities after cisplatin therapy; collective 2: liver and kidney side effects; collective 3: samples with defined high or low MRP-1 mRNA levels) were screened for all MRP-1 gene fragments, in which the new SNP's could be detected. For those of the newly identified MRP-1 SNP's which are overrepresented or underrepresented, the allele distribution was determined. As an example, the allele and genotype frequencies for one MRP-1 polymorphism are listed in the following table for collective 2 and compared to control samples:

| | | Frequency in % | | Frequency in % | | |
|---|---|---|---|---|---|---|
| SNP | Sample collection | Wt-allele | Mut-allele | heterozygotes | Homozygotes mutant | Homozygotes mutant (expected Hardy Weinberg) |
| G150727A (intron 28) | Controls | 66.7 | 33.3 | 50 | 8.3 | 10.9 |
| | Collective 2 | 50 | 50 | 14.3 | 42.9 | 25 |

In contrast to control samples the mutant allele (150727A) of one SNP found in the MRP-1 gene (G150727A, intron 28) is overrepresented in the samples of collective 2. Statistical evaluations were performed in regard to the presence of this SNP in samples with liver and kidney side effects (collective 2) compared to their frequencies in a control population. The statistical analysis was performed using the computer program SPSS 10.0 (SPSS, Chicago, USA). This evaluation results in a statistically significant correlation of a definite SNP with liver and kidney side effects.

The genotyp/phenotype correlation is confirmed by the p-value of the statistical evaluation (Chi-Quadrat-Test):

| gene | SNP | Controls vs. liver and kidney side effects, p-value |
|---|---|---|
| MRP-1 | G150727A (intron 28) | 0.044 |

Furthermore, a correlation of MRP-1 gene variants and mRNA expression of MRP-1 could be found for two new MRP-1 SNP's (T95C, exon 9, Asn to Asn and A259G, intron 9). These are linked SNP's (see also table in example 4). As shown in FIG. 3 (Diagramm A and B), the mutant allele correlates with decreased MRP-1 mRNA expression. Thus, the analysis of these functional important SNP's is of high diagnostic/prognostic value, because it allows the prediction of therapy outcome and side effects, and of expression levels of MRP-1.

EXAMPLE 8

MRP1 Genotypes in Patients Suffering from Drug-Induced Hepatic Toxicity

MRP1 genotypes were investigated in patients suffering from drug-induced hepatic toxicity (n=7) and healthy controls (n=95). Pearson chi-square was calculated from contingency tables to test the equality of proportions between patients and controls. When appropriate Fisher's Exact Test was applied. The level of significance was set to p=0.05. Statistical analysis was performed using SPSS 10.1 (SPSS, Chicago, USA). The level of significance was set to p=0.05.

Three SNPs (T>$C_{95}$, A>$G_{259}$, and C>$G_{53282}$) were found to be associated with the occurance of liver toxicity. The frequency of homozyguosly mutant genotypes was statistically significant elevated as summarized in the following table.

Frequency Distribution of MRP1 Genotypes

| SNP | | | Controls [%] | | | | Controls [%] | | | | |
|---|---|---|---|---|---|---|---|---|---|---|---|
| wt > $mut_{position}$ | AccNo[1] | SeqID | N | wt/wt | wt/m | m/m | N | wt/wt | wt/m | m/m | P[2] |
| T > $C_{95}$ | AF022831 | 171 | 7 | 47.8 | 44.6 | 7.6 | 92 | 85.7 | | 14.3 | 0.035 |
| A > $G_{259}$ | AF022831 | 177 | 7 | 47.8 | 44.6 | 7.6 | 92 | 85.7 | | 14.3 | 0.035 |
| C > $G_{53282}$ | GI: 7209451 | 195 | 6 | 55.3 | 40.4 | 4.3 | 94 | 85.3 | | 16.7 | 0.05 |

[1]Accession Number of reference sequence (wt allele)
[2]P value of statistical test
wt/wt homozygous wild types
wt/m heterozygots
m/m homozygous mutants Two of these SNPs are linked (T>$C_{95}$ and A>$G_{259}$) and have been demonstrated (example 7) to correlate with decreased MRP1 expression. It can be concluded that a reduced hepatic MRP1 expression leads to a decreased capacity of hepatocytes to transport toxic substrates with the consequence of an elevated risk to hepatocellular damage. Thus, SNPs in the MRP1 can explain interindividual variations in the susceptibility to adverse drug events (ADEs) and are important diagnostic markers to predict the individual risk of patients in order to prevent patients from ADEs by e.g. dosage adjustments or switching to other medications.

EXAMPLE 9

MRP1 Genotypes in Patients Suffering from Renal Carcinoma (RCC)

MRP1 genotypes were investigated in patients suffering from renal carcinoma (RCC) and healthy controls. Pearson chi-square was calculated from contingency tables to test the equality of proportions between RCC and controls. When appropriate Fisher's Exact Test was applied. The level of significance was set to p=0.05. Statistical analysis was performed using SPSS 10.1 (SPSS, Chicago, USA). Pearson chi-square was calculated to test the equality of proportions. The level of significance was set to p=0.05.

Three SNPs have been already described to be correlated with RCC in example 5. Additionally, the nucleotide substitution A>$G_{381}$ was found to be statistically significant associated with RCC and T>$C_{124667}$ tended to be associated with renal carcinoma confirming further the important role of MRP1 for pharmacology and toxicology of drugs.

Frequency Distribution of MRP1 Genotypes

| SNP | | | Patients [%] | | | | Controls [%] | | | | |
|---|---|---|---|---|---|---|---|---|---|---|---|
| wt > $mut_{position}$ | AccNo[1] | SeqID | N | wt/wt | wt/m | m/m | N | wt/wt | wt/m | m/m | P[2] |
| T > $C_{124667}$ | AC026452 | 075 | 33 | 45.5 | 51.5 | 3.0 | 90 | 57.8 | 31.1 | 11.1 | 0.075 |
| A > $G_{381}$ | U07050 | 111 | 59 | 35.6 | 52.5 | 11.9 | 88 | 53.6 | 32.1 | 14.3 | 0.027 |

[1]Accession Number of reference sequence (wt allele)
[2]P value of statistical test
wt/wt homozygous wild types
wt/m heterozygots
m/m homozygous mutants

TABLE 1

Primers for the amplification of fragments of the MRP1 gene

| PCR fragment name | PCR primer position | Primer sequence (5' to 3' orientation) | | PCR condition | Fragment size |
|---|---|---|---|---|---|
| | Accession number AC026452 | | | | |
| Exon 1/Prom 1 | 38590-38608 | MRP1-P1f | GTA GGG GGC TCC GTT CAC G | B | 880 bp |
| | 124576-124600 | MRP1-E1r2 | CCT GGA AGG TTG TTT TTA CAG ACG G | | |
| | Accession number U07050 | | | | |
| Promoter fragment 2 | 1359-1377 | MRP1-P2f | TGG AGA CTG GCG CCG TCT G | C | 408 bp |
| | 1767-1746 | MRP1-P2r | AAG GAC AGT ATC CGT CAC CAG G | | |

TABLE 1-continued

Primers for the amplification of fragments of the MRP1 gene

| PCR fragment name | PCR primer position | Primer sequence (5' to 3' orientation) | | PCR condition | Fragment size |
|---|---|---|---|---|---|
| Promoter fragment 3 | 830-851 | MRP1-P3f | CAT GGG GTT GTG AGG ATT GCA C | A | 590 bp |
| | 1423-1401 | MRP1-P3r | TGA GAT TCA AAC CCG TGA GCA GC | | |
| Promoter fragment 4 | 351-374 | MRP1-P4f | CTT AGA AAC TCA TTC ACC CTT GGG | A | 550 bp |
| | 902-881 | MRP1-P4r | GTG ACA AGG CTT CCT AAG GCT G | | |
| Promoter fragment 5 | 144-170 | MRP1-P5f | GAT TAA CAT CTG CCA TCT TAC CAT AAG | A | 321 bp |
| | 465-445 | MRP1-P5r | GCT CCC CCC AAT CAA AGG ACC | | |
| | GI number 7209451 | | | | |
| Exon 2 | 39769-39789 | MRP1-E2f1 | AGC TGG TTT CAT GCT CCA GGC | A | 374 bp |
| | 39416-39440 | MRP1-E2r1 | CTA GAA GAA GGA ACT TAG GGT CAA C | | |
| | Accession number AF022825 | | | | |
| Exon 3 | 24-44 | MRP1-E3f | TTC CAG GGC GGT CTG TTG TAG | A | 233 bp |
| | 257-235 | MRP1-E3r | ATT ACT TTT GGT CTC CAC TGA GC | | |
| | Accession number AF022826 | | | | |
| Exon 4 | 68-90 | MRP1-E4f2 | AAA ACC CAA CAA CTC CTG TCT TG | A | 230 bp |
| | 297-278 | MRP1-E4r | CCA TCT TTC CCT CCG GCT CC | | |
| | Accession number AF022827 | | | | |
| Exon 5 | 35-55 | MRP1-E5f1 | ACC CAG CCC CAG AAT GTG ATC | A | 206 bp |
| | 240-219 | MRP1-E5r2 | GCA CAC ACA CTC ATT TGT GGT C | | |
| | Accession number AF022828 | | | | |
| Exon 6 | 4-26 | MRP1-E6f | GAG CAG CTG ACT ACT TGC TAA GC | A | 209 bp |
| | 212-190 | MRP1-E6r1 | CAT TCA TTC ATT CAC TCC CCA CC | | |
| | Accession number AF022829 | | | | |
| Exon 7 | 17-41 | MRP1-E7f | CTG TCA TTG ACT CTC ATT GCC TAA C | A | 279 bp |
| | 295-275 | MRP1-E7r1 | AGT AAC AGG CAG CAC TGC GAG | | |
| | Accession number AF022830 | | | | |
| Exon 8 | 29-49 | MRP1-E8f | ATC TCT GGC AGA CCC CAC AAC | A | 336 bp |
| | 364-341 | MRP1-E8r1 | AAC TGA AAG ATC AAA GCC AAG GAG | | |
| | Accession number AF022831 | | | | |
| Exon 9 | 26-47 | MRP1-E9f | CCC CAC GTG TCA CAA GTC ATT C | A | 322 bp |
| | 347-328 | MRP1-E9r | TGG GCT GGA AAT CCC CAC GC | | |
| | GI number | | | | |

TABLE 1-continued

Primers for the amplification of fragments of the MRP1 gene

| PCR fragment name | PCR primer position | Primer sequence (5' to 3' orientation) | | PCR condition | Fragment size |
|---|---|---|---|---|---|
| | 7209451 | | | | |
| Exon 10 | 58203-58184 | MRP1-E10f1 | GGG AGG AGG AGA GAT CTG CG | A | 413 bp |
| | 57791-57810 | MRP1-E10r1 | TGA ACC ACA GCC GGA ACT GC | | |
| | GI number 7209451 | | | | |
| Exon 11 | 53578-53559 | MRP1-E11f | GGA TGG ATC AAC CGG GGA AG | A | 353 bp |
| | 53226-53248 | MRP1-E11r | TCA GAA TCC CAG ATA TGC AGC CG | | |
| | GI number 7209451 | | | | |
| Exon 12 | 22183-22204 | MRP1-E12f1 | TGT TGA GTG ATG GGC TGA TCC C | A | 344 bp |
| | 22526-22499 | MRP1-E12r | CCT TTT AAA AAT ATT CAG GTA CGC AGA G | | |
| | Accession number AC003026 | | | | |
| Exon 13 | 11927-11949 | MRP1-E13f | CAC TGC TCC TAG GAT GAT GAC TC | A | 312 bp |
| | 12238-12218 | MRP1-E13r | GAG TGT GAT CTA GAG GCT GCG | | |
| Exon 14 | 15397-15419 | MRP1-E14f | GGG GAA ACC CTT GAA AGT TAA CC | A | 264 bp |
| | 15660-15638 | MRP1-E14r | CAG CCA AGG GAA AGA AAT GCA AG | | |
| Exon 15 | 20044-20063 | MRP1-E15f | ATG CCT AGC GCC ATT CGT GC | A | 285 bp |
| | 20328-20309 | MRP1-E15r | GGG AGC ACG GTG GGA ATT CG | | |
| Exon 16 | 23040-23063 | MRP1-E16f | GAA GGA ATG TTG AGG CCT TCA GTG | A | 402 bp |
| | 23441-23418 | MRP1-E16r | GAA AAG AGA CGT TGC TGC TTT CGC | | |
| Exon 17 | 27108-27128 | MRP1-E17f | AAG TGA GGC CCT CCT AGC AGG | C | 372 bp |
| | 27479-27458 | MRP1-E17r | TGA TAG CAG CAG ACT CAC AGC C | | |
| Exon 18 | 30588-30607 | MRP1-E18f | ACA CTC GGC CTG CTT CTA CG | A | 326 bp |
| | 30913-30892 | MRP1-E18r | AAG GAC TCC TAA AGG GGA CAC G | | |
| Exon 19 | 34085-34105 | MRP1-E19f | GCT CCT GGA TGC TGT TAT CGC | A | 430 bp |
| | 34514-34495 | MRP1-E19r2 | TGG CTG GTG GCA ACC TCA AAG | | |
| | Accession number AC003026 | | | | |
| Exon 20 | 46405-46427 | MR-E20f2 | CCC TTG GTT TTA GCA TCT GCC TC | A | 239 bp |
| | 46643-46621 | MR-E20r | GGG CTG AGG CCT TTT TTT GTT CC | | |
| Exon 21 | 50449-50471 | MRP1-E21f | TGT GTG CAT GTG GAA ACA CTC CG | A | 368 bp |
| | 50816-50792 | MRP1-E21r | GAC AGG TGA GTT AAC ATA GAC AAG G | | |
| | Accession number AC003026 | | | | |
| Exon 22 | 55116-55134 | MRP1-E22f | TGC TGG TGA AGC CCC CGA C | A | 402 bp |
| | 55517-55497 | MRP1-E22r | GTT TGG GGT CCC ACA AAA CGC | | |
| Exon 23 | 58530-58548 | MRP1-E23f3 | CTC CCT GCA GTG CCT GGT C | A | 474 bp |
| | 59003-58983 | MRP1-E23r3 | CCA CAC TGG GGA CAT GGT AAG | | |
| Exon 24 | 65670-65688 | MRP1-E24f1 | AGG GCA GCC CGG CTC TAA C | A | 444 bp |
| | 66113-66093 | MRP1-E24r | GCC GGG GTT TGG CTT TAT ACC | | |
| | Accession number U91318 | | | | |
| Exon 25 | 4270-4292 | MRP1-E25f | CTC TCT CTG GAA TTA CTG CGG AG | A | 385 bp |
| | 4654-4634 | MRP1-E25r | CTG CTC CTC AAA CTC CGT ACC | | |

TABLE 1-continued

Primers for the amplification of fragments of the MRP1 gene

| PCR fragment name | PCR primer position | Primer sequence (5' to 3' orientation) | | PCR condition | Fragment size |
|---|---|---|---|---|---|
| Exon 26 | 5371-5393 | MRP1-E26f | GAA AGT CAA GTA CGC CCG CTT AC | A | 242 bp |
| | 5612-5593 | MRP1-E26r | AGG TGC ACA GGA TAG GGT CC | | |
| Exon 27 | 11200-11220 | MRP1-E27f | CTG AGA GGG TGC TCT GTA TCG | A | 545 bp |
| | 11744-11721 | MRP1-E27r | CAC TTC TGC AAG TTG TAT GCG CTC | | |
| Exon 28 | 13844-13863 | MR-E28f | GAG AGG GCT GTC GAG TTG GG | C | 349 bp |
| | 14192-14170 | MR-E28r | TCA GTG CAA TCA TAG GGC TTG CC | | |
| | Accession number U91318 | | | | |
| Exon 29 | 16017-16036 | MR-E29f | CCA GAA GTC CTT AGG TCG CC | A | 317 bp |
| | 16333-16311 | MR-E29r | CTT CAA ACA CCC CTA CCG AGA TG | | |
| Exon 30 | 17859-17880 | MR-E30f | GGA CAT GCT TTC CTG GTC AAG C | A | 430 bp |
| | 18288-18268 | MR-E30r | GGG CTG TCA CTA GGG ATA AGG | | |
| Exon 31, (incl. 3'-UTR) | 20650-20670 | MR-E31f | GCA ACC AGC TGG AAG GTA CTG | A | 592 bp |
| | 21241-21219 | MR-E31r | CAG AAG TCT GGC TGC CAA AAC TC | | |

Conditions for the different PCR fragments:

PCRs were carried out for all fragments in a reaction volume of 50 μl. 40 ng DNA template was added to standard PCR buffer containing 1.5 mM MgCl2 (Qiagen, Hilden), 200 μM dNTP's (Roth, Karlsruhe), 0.4 μM (conditions A and C) or 1.6 μM (condition B) of each primer (Metabion, Munich), 10 μl Q-Solution (condition C; Qiagen, Hilden), 4 μl DMSO (condition B) and 1 U Taq polymerase (Qiagen, Hilden). All PCRs (conditions A and C) were performed on a Perkin Elmer thermocycler (model 9700) with an initial denaturation step of 2 min at 94° C. and 34 amplification cycles of denaturation at 94° C. for 45 sec, primer annealing at 62° C. for 45 sec, and 1 min for 72° C. followed by a final extension of 72° C. for 10 min. In the case of condition B the PCR reaction was performed with an initial denaturation step of 3 min at 96° C. and 35 amplification cycles of denaturation at 96° C. for 45 sec, primer annealing at 62° C. for 30 sec, and 1 min for 72° C. followed by a final extension of 72° C. for 10 min.

TABLE 2

New SNP's in the gene for MRP1

| PCR fragment name | Position of the variation | wt-sequence | wt/mut- and/or mut-sequence |
|---|---|---|---|
| | Accession number AC026452 | | |
| Exon 1/Prom 1 (intron 1) | 124667 (SNP 34) | f: GCGTGCCCAG**T**CCTGGGGTTT (SEQ ID No: 071)<br>r: AAACCCCAGG**A**CTGGGCACGC (SEQ ID No: 072) | wt/mut:<br>f: GCGTGCCCAG**T/C**CCTGGGGTTT (SEQ ID No: 073)<br>r: AAACCCCAGG**A/G**CTGGGCACGC (SEQ ID No: 074)<br>mut/mut:<br>f: GCGTGCCCAG**C**CCTGGGGTTT (SEQ ID No: 075)<br>r: AAACCCCAGG**G**CTGGGCACGC (SEQ ID No: 076) |
| | Accession number U07050 | | |
| Exon 1/Prom 1 | 1884 (SNP 33) | f: AGCCTTGGAG**G**ATCTGGGGTG (SEQ ID No: 077)<br>r: CACCCCAGAT**C**CTCCAAGGCT (SEQ ID No: 078) | wt/mut:<br>f: AGCCTTGGAG**G/A**ATCTGGGGTG (SEQ ID No: 079)<br>r: CACCCCAGAT**C/T**CTCCAAGGCT (SEQ ID No: 080)<br>mut/mut:<br>f: AGCCTTGGAG**A**ATCTGGGGTG (SEQ ID No: 081)<br>r: CACCCCAGAT**T**CTCCAAGGCT (SEQ ID No: 082) |
| | | | wt/mut: |

TABLE 2-continued

New SNP's in the gene for MRP1

| PCR fragment name | Position of the variation | wt-sequence | wt/mut- and/or mut-sequence |
|---|---|---|---|
| Promoter fragment 2 | 1720-1723 del GGTA (SNP 25) | f: ACTCCAGGCA**GGTA**GGGGGCTCCG (SEQ ID No: 083) r: CGGAGCCCCC**TACC**TGCCTGGAGT (SEQ ID No: 084) | f: ACTCCAGGCA**GGTA/delGGTA**GGGGGCTCCG (SEQ ID No: 085) r: CGGAGCCCCC**TACC/delTACC**TGCCTGGAGT (SEQ ID No: 086) mut/mut: f: ACTCCAGGCA**delGGTA**GGGGGCTCCG (SEQ ID No: 087) r: CGGAGCCCCC**delTACC**TGCCTGGAGT (SEQ ID No: 088) |
| | Accession number U07050 | | wt/mut: |
| Promoter fragment 3 | 1163 (SNP22) | f: TGTGATCGGC**C**CGCCTCGGCT (SEQ ID No: 089) r: AGCCGAGGCG**G**GCCGATCACA (SEQ ID No: 090) | f: TGTGATCGGC**C/T**CGCCTCGGCT (SEQ ID No: 091) r: AGCCGAGGCG**G/A**GCCGATCACA (SEQ ID No: 092) mut/mut: f: TGTGATCGGC**T**CGCCTCGGCT (SEQ ID No: 093) r: AGCCGAGGCG**A**GCCGATCACA (SEQ ID No: 094) |
| | | | wt/mut: |
| Promoter fragment 3 | 926 (SNP 21) | f: TTAATTTTTT**T**ATTATTATTT (SEQ ID No: 095) r: AAATAATAAT**A**AAAAAATTAA (SEQ ID No: 096) | f: TTAATTTTTT**T/insT**ATTATTATTT (SEQ ID No: 097) r: AAATAATAAT**A/insA**AAAAAATTAA (SEQ ID No: 098) mut/mut: f: TTAATTTTTTT**InsT**ATTATTATTT (SEQ ID No: 099) r: AAATAATAAT**insA**AAAAAAATTAA (SEQ ID No: 100) |
| | | | wt/mut: |
| Promoter fragment 4 | 437 (SNP 31) | f: TTCCTCCTTC**C**CTCGCTAGGT (SEQ ID No: 101) r: ACCTAGCGAG**G**GAAGGAGGAA (SEQ ID No: 102) | f: TTCCTCCTTC**C/insTCCTTCC**CTCGCTAGGT (SEQ ID No: 103) r: ACCTAGCGAG**G/insAGGAAGG**GAAGGAGGAA (SEQ ID No: 104) mut/mut: f: TTCCTCCTTCC**TCCTTCC**CTCGCTAGGT (SEQ ID No: 105) r: ACCTAGCGAG**GGAAGGA**GGAAGGAGGAA (SEQ ID No: 106) |
| | Accession number U07050 | | wt/mut: |
| Promoter fragment 5 | 381 (SNP 20/30) | f: TGGGGGACCC**A**GGCCAATAAA (SEQ ID No: 107) r: TTTATTGGCC**T**GGGTCCCCCA (SEQ ID No: 108) | f: TGGGGGACCC**A/G**GGCCAATAAA (SEQ ID No: 109) r: TTTATTGGCC**T/C**GGGTCCCCCA (SEQ ID No: 110) mut/mut: f: TGGGGGACCC**G**GGCCAATAAA (SEQ ID No: 111) r: TTTATTGGCC**C**GGGTCCCCCA (SEQ ID No: 112) |
| | | | wt/mut: |
| Promoter fragment 5 | 233 (SNP 19) | f: AAGAGTAGCA**G**TTTTATCTTG (SEQ ID No: 113) r: CAAGATAAAA**C**TGCTACTCTT (SEQ ID No: 114) | f: AAGAGTAGCA**G/A**TTTTATCTTG (SEQ ID No: 115) r: CAAGATAAAA**C/T**TGCTACTCTT (SEQ ID No:116) mut/mut: f: AAGAGTAGCA**A**TTTTATCTTG (SEQ ID No: 117) r: CAAGATAAAA**T**TGCTACTCTT (SEQ ID No: 118) |
| | | | wt/mut: |

TABLE 2-continued

New SNP's in the gene for MRP1

| PCR fragment name | Position of the variation | wt-sequence | wt/mut- and/or mut-sequence |
|---|---|---|---|
| Promoter fragment 5 | 189<br>(SNP 35) | f: AAAAAAATCC**C**AATCCAAAAA<br>(SEQ ID No: 119)<br>r: TTTTTGGATT**G**GGATTTTTTT<br>(SEQ ID No: 120) | f: AAAAAAATCC**C/A**AATCCAAAAA<br>(SEQ ID No: 121)<br>r: TTTTTGGATT**G/T**GGATTTTTTT<br>(SEQ ID No: 122)<br>mut/mut:<br>f: AAAAAAATCC**A**AATCCAAAAA<br>(SEQ ID No: 123)<br>r: TTTTTGGATT**T**GGATTTTTTT<br>(SEQ ID No: 124) |
| Exon 2<br>(intron 2) | GI number<br>7209451<br>39508<br>(SNP 1) | f: GTTTCGTTGT**G**GGGGGTGGGA<br>(SEQ ID No: 125)<br>r: TCCCACCCCC**C**ACAACGAAAC<br>(SEQ ID No: 126) | wt/mut:<br>f: GTTTCGTTGT**G/A**GGGGGTGGGA<br>(SEQ ID No: 127)<br>r: TCCCACCCCC**C/T**ACAACGAAAC<br>(SEQ ID No: 128)<br>mut/mut:<br>f: GTTTCGTTGT**A**GGGGGTGGGA<br>(SEQ ID No: 129)<br>r: TCCCACCCCC**T**ACAACGAAAC<br>(SEQ ID No: 130) |
| Exon 6<br>(intron 6) | Accession number<br>AF022828<br>174<br>(SNP 10) | f: CCAGGCCCCC**C**AGACCTCAGG<br>(SEQ ID No: 131)<br>r: CCTGAGGTCT**G**GGGGGCCTGG<br>(SEQ ID No: 132) | wt/mut:<br>f: CCAGGCCCCC**C/T**AGACCTCAGG<br>(SEQ ID No: 133)<br>r: CCTGAGGTCT**G/A**GGGGGCCTGG<br>(SEQ ID No: 134)<br>mut/mut:<br>f: CCAGGCCCCC**T**AGACCTCAGG<br>(SEQ ID No: 135)<br>r: CCTGAGGTCT**A**GGGGGCCTGG<br>(SEQ ID No: 136) |
| Exon 7<br>(intron 7) | Accession number<br>AF022829<br>248<br>(SNP 2) | f: CCTTTCCACT**C**CTGTGGCCTC<br>(SEQ ID No: 137)<br>r: GAGGCCACAG**G**AGTGGAAAGG<br>(SEQ ID No: 138) | wt/mut:<br>f: CCTTTCCACT**C/A**CTGTGGCCTC<br>(SEQ ID No: 139)<br>r: GAGGCCACAG**G/T**AGTGGAAAGG<br>(SEQ ID No: 140)<br>mut/mut:<br>f: CCTTTCCACT**A**CTGTGGCCTC<br>(SEQ ID No: 141)<br>r: GAGGCCACAG**T**AGTGGAAAGG<br>(SEQ ID No: 142) |
| Exon 7<br>(intron 7) | 258<br>(SNP 3) | f: CCTGTGGCCT**C**AATCCAGGAT<br>(SEQ ID No: 143)<br>r: ATCCTGGATT**G**AGGCCACAGG<br>(SEQ ID No: 144) | wt/mut:<br>f: CCTGTGGCCT**C/G**AATCCAGGAT<br>(SEQ ID No: 145)<br>r: ATCCTGGATT**G/C**AGGCCACAGG<br>(SEQ ID No: 146)<br>mut/mut:<br>f: CCTGTGGCCT**G**AATCCAGGAT<br>(SEQ ID No: 147)<br>r: ATCCTGGATT**C**AGGCCACAGG<br>(SEQ ID No: 148) |
| Exon 8 | Accession number<br>AF022830<br>79<br>(SNP 4) | f: CCAGGCAGCC**G**GTGAAGGTTG<br>(SEQ ID No: 149)<br>r: CAACCTTCAC**C**GGCTGCCTGG<br>(SEQ ID No: 150) | wt/mut:<br>f: CCAGGCAGCC**G/A**GTGAAGGTTG<br>(SEQ ID No: 151)<br>r: CAACCTTCAC**C/T**GGCTGCCTGG<br>(SEQ ID No: 152)<br>mut/mut:<br>f: CCAGGCAGCC**A**GTGAAGGTTG<br>(SEQ ID No: 153) |

TABLE 2-continued

New SNP's in the gene for MRP1

| PCR fragment name | Position of the variation | wt-sequence | wt/mut- and/or mut-sequence |
|---|---|---|---|
| | | | r: CAACCTTCAC**T**GGCTGCCTGG (SEQ ID No: 154) |
| Exon 8 | Accession number AF022830 88 (SNP 5) | f: CGGTGAAGGT**T**GTGTACTCCT (SEQ ID No: 155) r: AGGAGTACAC**A**ACCTTCACCG (SEQ ID No: 156) | wt/mut: f: CGGTGAAGGT**T/C**GTGTACTCCT (SEQ ID No: 157) r: AGGAGTACAC**A/G**ACCTTCACCG (SEQ ID No: 158) mut/mut: f: CGGTGAAGGT**C**GTGTACTCCT (SEQ ID No: 159) r: AGGAGTACAC**G**ACCTTCACCG (SEQ ID No: 160) |
| Exon 8 | 249 (SNP 37) (only in RCC samples) | f: CTCATGAGCT**T**CTTCTTCAAG (SEQ ID No: 161) r: CTTGAAGAAG**A**AGCTCATGAG (SEQ ID No: 162) | wt/mut: f: CTCATGAGCT**T/G**CTTCTTCAAG (SEQ ID No: 163) r: CTTGAAGAAG**A/C**AGCTCATGAG (SEQ ID No: 164) mut/mut: f: CTCATGAGCT**G**CTTCTTCAAG (SEQ ID No: 165) r: CTTGAAGAAG**C**AGCTCATGAG (SEQ ID No: 166) |
| Exon 9 | Accession number AF022831 95 (SNP 6) | f: AGTTCGTGAA**T**GACACGAAGG (SEQ ID No: 167) r: CCTTCGTGTC**A**TTCACGAACT (SEQ ID No: 168) | wt/mut: f: AGTTCGTGAA**T/C**GACACGAAGG (SEQ ID No: 169) r: CCTTCGTGTC**A/G**TTCACGAACT (SEQ ID No: 170) mut/mut: f: AGTTCGTGAA**C**GACACGAAGG (SEQ ID No: 171) r: CCTTCGTGTC**G**TTCACGAACT (SEQ ID No: 172) |
| Exon 9 (intron 9) | 259 (SNP 7) | f: AAGGTAGGGG**A**CGCTGTGCCA (SEQ ID No: 173) r: TGGCACAGCG**T**CCCCTACCTT (SEQ ID No: 174) | wt/mut: f: AAGGTAGGGG**A/G**CGCTGTGCCA (SEQ ID No: 175) r: TGGCACAGCG**T/C**CCCCTACCTT (SEQ ID No: 176) mut/mut: f: AAGGTAGGGG**G**CGCTGTGCCA (SEQ ID No: 177) r: TGGCACAGCG**C**CCCCTACCTT (SEQ ID No: 178) |
| Exon 10 | GI number 7209451 57998 (SNP 11) | f: ACGCTCAGAG**G**TTCATGGACT (SEQ ID No: 179) r: AGTCCATGAA**C**CTCTGAGCGT (SEQ ID No: 180) | wt/mut: f: ACGCTCAGAG**G/T**TTCATGGACT (SEQ ID No: 181) r: AGTCCATGAA**C/A**CTCTGAGCGT (SEQ ID No: 182) mut/mut: f: ACGCTCAGAG**T**TTCATGGACT (SEQ ID No: 183) r: AGTCCATGAA**A**CTCTGAGCGT (SEQ ID No: 184) |
| | | | wt/mut: |

TABLE 2-continued

New SNP's in the gene for MRP1

| PCR fragment name | Position of the variation | wt-sequence | wt/mut- and/or mut-sequence |
|---|---|---|---|
| Exon 10<br>(intron 10) | 57853<br>(SNP 8) | f: GGCAGTGGGC**C**GAGGGAGTGG<br>(SEQ ID No: 185)<br>r: CCACTCCCTC**G**GCCCACTGCC<br>(SEQ ID No: 186) | f: GGCAGTGGGC**C/T**GAGGGAGTGG<br>(SEQ ID No: 187)<br>r: CCACTCCCTC**G/A**GCCCACTGCC<br>(SEQ ID No: 188)<br>mut/mut:<br>f: GGCAGTGGGC**T**GAGGGAGTGG<br>(SEQ ID No: 189)<br>r: CCACTCCCTC**A**GCCCACTGCC<br>(SEQ ID No: 190) |
| Exon 11<br>(intron 11) | 53282<br>(SNP 12) | f: GCCAGTTGGA**C**TCACTTGGGG<br>(SEQ ID No: 191)<br>r: CCCCAAGTGA**G**TCCAACTGGC<br>(SEQ ID No: 192) | wt/mut:<br>f: GCCAGTTGGA**C/G**TCACTTGGGG<br>(SEQ ID No: 193)<br>r: CCCCAAGTGA**G/C**TCCAACTGGC<br>(SEQ ID No: 194)<br>mut/mut:<br>f: GCCAGTTGGA**G**TCACTTGGGG<br>(SEQ ID No: 195)<br>r: CCCCAAGTGA**C**TCCAACTGGC<br>(SEQ ID No: 196) |
| Exon 13<br>(intron 12) | Accession number AC026452<br>137710<br>(SNP 26) | f: ACTCTCACTC**A**GGGCACAGCA<br>(SEQ ID No: 197)<br>r: TGCTGTGCCC**T**GAGTGAGAGT<br>(SEQ ID No: 198) | wt/mut:<br>f: ACTCTCACTC**A/G**GGGCACAGCA<br>(SEQ ID No: 199)<br>r: TGCTGTGCCC**T/C**GAGTGAGAGT<br>(SEQ ID No: 200)<br>mut/mut:<br>f: ACTCTCACTC**G**GGGCACAGCA<br>(SEQ ID No: 201)<br>r: TGCTGTGCCC**C**GAGTGAGAGT<br>(SEQ ID No: 202) |
| Exon 13 | Accession number AC026452<br>137667<br>(SNP 13) | f: GCAGGTGGCC**C**TGTGCACATT<br>(SEQ ID No: 203)<br>r: AATGTGCACA**G**GGCCACCTGC<br>(SEQ ID No: 204) | wt/mut:<br>f: GCAGGTGGCC**C/T**TGTGCACATT<br>(SEQ ID No: 205)<br>r: AATGTGCACA**G/A**GGCCACCTGC<br>(SEQ ID No: 206)<br>mut/mut:<br>f: GCAGGTGGCC**T**TGTGCACATT<br>(SEQ ID No: 207)<br>r: AATGTGCACA**A**GGCCACCTGC<br>(SEQ ID No: 208) |
| Exon 13 | 137647<br>(SNP 14) | f: TTGCCGTCTA**C**GTGACCATTG<br>(SEQ ID No: 209)<br>r: CAATGGTCAC**G**TAGACGGCAA<br>(SEQ ID No: 210) | wt/mut:<br>f: TTGCCGTCTA**C/T**GTGACCATTG<br>(SEQ ID No: 211)<br>r: CAATGGTCAC**G/A**TAGACGGCAA<br>(SEQ ID No: 212)<br>mut/mut:<br>f: TTGCCGTCTA**T**GTGACCATTG<br>(SEQ ID No: 213)<br>r: CAATGGTCAC**A**TAGACGGCAA<br>(SEQ ID No: 214) |
| Exon 17<br>(intron 16) | Accession number A0003026<br>27159<br>(SNP: mr-v-024) | f: TCGTTGATCA**G**ATCTGTCTGT<br>(SEQ ID No: 215)<br>r: ACAGACAGAT**C**TGATCAACGA<br>(SEQ ID No: 216) | wt/mut:<br>f: TCGTTGATCA**G/C**ATCTGTCTGT<br>(SEQ ID No: 217)<br>r: ACAGACAGAT**C/G**TGATCAACGA<br>(SEQ ID No: 218)<br>mut/mut:<br>f: TCGTTGATCA**C**ATCTGTCTGT<br>(SEQ ID No: 219)<br>r: ACAGACAGAT**G**TGATCAACGA<br>(SEQ ID No: 220) |
| | | | wt/mut: |

TABLE 2-continued

New SNP's in the gene for MRP1

| PCR fragment name | Position of the variation | wt-sequence | wt/mut- and/or mut-sequence |
|---|---|---|---|
| Exon 17 | 27258<br>(SNP 9) | f: GATTCTCTCC**G**AGAAAACATC<br>(SEQ ID No: 221)<br>r: GATGTTTTCT**C**GGAGAGAATC<br>(SEQ ID No: 222) | f: GATTCTCTCC**G/A**AGAAAACATC<br>(SEQ ID No: 223)<br>r: GATGTTTTCT**C/T**GGAGAGAATC<br>(SEQ ID No: 224)<br>mut/mut:<br>f: GATTCTCTCC**A**AGAAAACATC<br>(SEQ ID No: 225)<br>r: GATGTTTTCT**T**GGAGAGAATC<br>(SEQ ID No: 226) |
| Exon 19<br>(intron 18) | Accession number AC003026<br>34206/34207<br>(SNP 18) | f: AGTCTCACAC**AT**GTGCACTCAC<br>(SEQ ID No: 227)<br>r: GTGAGTGCAC**AT**GTGTGAGACT<br>(SEQ ID No: 228) | wt/mut:<br>f: AGTCTCACAC**AT/delAT**GTGCACTCAC<br>(SEQ ID No: 229)<br>r: GTGAGTGCAC**AT/delAT**GTGTGAGACT<br>(SEQ ID No: 230)<br>mut/mut:<br>f: AGTCTCACAC**delAT**GTGCACTCAC<br>(SEQ ID No: 231)<br>r: GTGAGTGCAC**delAT**GTGTGAGACT<br>(SEQ ID No: 232) |
| Exon 19<br>(intron 18) | 34215<br>(SNP 17) | f: CATGTGCACT**G**ACGTGGCCGG<br>(SEQ ID No: 233)<br>r: CCGGCCACGT**C**AGTGCACATG<br>(SEQ ID No: 234) | wt/mut:<br>f: CATGTGCACT**G/C**ACGTGGCCGG<br>(SEQ ID No: 235)<br>r: CCGGCCACGT**C/G**AGTGCACATG<br>(SEQ ID No: 236)<br>mut/mut:<br>f: CATGTGCACT**C**ACGTGGCCGG<br>(SEQ ID No: 237)<br>r: CCGGCCACGT**G**AGTGCACATG<br>(SEQ ID No: 238) |
| Exon 22<br>(intron 21) | 55156<br>(SNP 28) | f: GGGGCTGGGG**C**TGGGTGCGTG<br>(SEQ ID No: 239)<br>r: CACGCACCCA**G**CCCCAGCCCC<br>(SEQ ID No: 240) | wt/mut:<br>f: GGGGCTGGGG**C/insTGGGGC**TGGGTGCGTG<br>(SEQ ID No: 241)<br>r: CACGCACCCA**G/insGCCCCA**CCCCAGCCCC<br>(SEQ ID No: 242)<br>mut/mut:<br>f: GGGGCTGGGGC**insTGGGGC**TGGGTGCGTG<br>(SEQ ID No: 243)<br>r: CACGCACCCA**insGCCCCA**GCCCCAGCCCC<br>(SEQ ID No: 244) |
| Exon 22<br>(intron 22) | Accession number AC003026<br>55472<br>(SNP 27) | f: TGTCTAATTA**T**AGAAATGGAT<br>(SEQ ID No: 245)<br>r: ATCCATTTCT**A**TAATTAGACA<br>(SEQ ID No: 246) | wt/mut:<br>f: TGTCTAATTA**T/C**AGAAATGGAT<br>(SEQ ID No: 247)<br>r: ATCCATTTCT**A/G**TAATTAGACA<br>(SEQ ID No: 248)<br>mut/mut:<br>f: TGTCTAATTA**C**AGAAATGGAT<br>(SEQ ID No: 249)<br>r: ATCCATTTCT**G**TAATTAGACA<br>(SEQ ID No: 250) |
| Exon 28 | Accession number U91318<br>14008<br>(SNP 23) | f: CTGGGAAGTC**G**TCCCTGACCC<br>(SEQ ID No: 251)<br>r: GGGTCAGGGA**C**GACTTCCCAG<br>(SEQ ID No: 252) | wt/mut:<br>f: CTGGGAAGTC**G/A**TCCCTGACCC<br>(SEQ ID No: 253)<br>r: GGGTCAGGGA**C/T**GACTTCCCAG<br>(SEQ ID No: 254)<br>mut/mut:<br>f: CTGGGAAGTC**A**TCCCTGACCC<br>(SEQ ID No: 255)<br>r: GGGTCAGGGA**T**GACTTCCCAG<br>(SEQ ID No: 256) |
| | Accession number AC025277 | | wt/mut: |

TABLE 2-continued

New SNP's in the gene for MRP1

| PCR fragment name | Position of the variation | wt-sequence | wt/mut- and/or mut-sequence |
|---|---|---|---|
| Exon 29 (intron 28) | 150727 (SNP 24) | f: CCATGTCAGC**G**TGACACAGGT (SEQ ID No: 257) r: ACCTGTGTCA**C**GCTGACATGG (SEQ ID No: 258) | f: CCATGTCAGC**G/A**TGACACAGGT (SEQ ID No: 259) r: ACCTGTGTCA**C/T**GCTGACATGG (SEQ ID No: 260) mut/mut: f: CCATGTCAGC**A**TGACACAGGT (SEQ ID No: 261) r: ACCTGTGTCA**T**GCTGACATGG (SEQ ID No: 262) |
| Exon 30 (intron 29) | Accession number U91318 17970 (SNP 15) | f: CTGGTTTTTT**T**CTTCCGGTCA (SEQ ID No: 263) r: TGACCGGAAG**A**AAAAAACCAG (SEQ ID No: 264) | wt/mut: f: CTGGTTTTTT**T/delT**CTTCCGGTCA (SEQ ID No: 265) r: TGACCGGAAG**A/delA**AAAAAACCAG (SEQ ID No: 266) mut/mut: f: CTGGTTTTTT**delT**CTTCCGGTCA (SEQ ID No: 267) r: TGACCGGAAG**delA**AAAAAACCAG (SEQ ID No: 268) |
| Exon 30 (intron 30) | Accession number U91318 18195 (SNP 16) | f: CACTGGCACA**G**TGGCCTCTAG (SEQ ID No: 269) r: CTAGAGGCCA**C**TGTGCCAGTG (SEQ ID No: 270) | wt/mut: f: CACTGGCACA**G/A**TGGCCTCTAG (SEQ ID No: 271) r: CTAGAGGCCA**C/T**TGTGCCAGTG (SEQ ID No: 272) mut/mut: f: CACTGGCACA**A**TGGCCTCTAG (SEQ ID No: 273) r: CTAGAGGCCA**T**TGTGCCAGTG (SEQ ID No: 274) |
| Exon 31 (3' flanking region) | 21133 (SNP 29) | f: CCCAAAACAC**G**CACACCCTGC (SEQ ID No: 275) r: GCAGGGTGTG**C**GTGTTTTGGG (SEQ ID No: 276) | wt/mut: f: CCCAAAACAC**G/A**CACACCCTGC (SEQ ID No: 277) r: GCAGGGTGTG**C/T**GTGTTTTGGG (SEQ ID No: 278) mut/mut: f: CCCAAAACAC**A**CACACCCTGC (SEQ ID No: 279) r: GCAGGGTGTG**T**GTGTTTTGGG (SEQ ID No: 280) |
| Exon 19 (intron 18) | Accession number AC003026 34218 (SNP 38) (only in RCC samples) | f: GTGCACTCAC**G**TGGCCGGGTG (SEQ ID No: 281) r: CACCCGGCCA**C**GTGAGTGCAC (SEQ ID No: 282) | wt/mut: f: GTGCACTCAC**G/A**TGGCCGGGTG (SEQ ID No: 283) r: CACCCGGCCA**C/T**GTGAGTGCAC (SEQ ID No: 284) mut/mut: f: GTGCACTCAC**A**TGGCCGGGTG (SEQ ID No: 285) r: CACCCGGCCA**T**GTGAGTGCAC (SEQ ID No: 286) |
| Exon 30 | Accession number U91318 18067 (SNP 39) (only in RCC samples) | f: CCACGGCAGC**C**GTGGACCTGG (SEQ ID No: 287) r: CCAGGTCCAC**G**GCTGCCGTGG (SEQ ID No: 288) | wt/mut: f: CCACGGCAGC**C/T**GTGGACCTGG (SEQ ID No: 289) r: CCAGGTCCAC**G/A**GCTGCCGTGG (SEQ ID No: 290) mut/mut: f: CCACGGCAGC**T**GTGGACCTGG (SEQ ID No: 291) R: CCAGGTCCAC**A**GCTGCCGTGG (SEQ ID No: 292) |

TABLE 2-continued

New SNP's in the gene for MRP1

| PCR fragment name | Position of the variation | wt-sequence | wt/mut- and/or mut-sequence |
|---|---|---|---|
| | Accession number U07050 | | wt/mut: |
| Promoter fragment 5 | 440 (SNP 40) (only in RCC samples) | f: CTCCTTCCCT**C**GCTAGGTCCT (SEQ ID No: 293) r: AGGACCTAGC**G**AGGGAAGGAG (SEQ ID No: 294) | f: CTCCTTCCCT**C/T**GCTAGGTCCT (SEQ ID No: 295) r: AGGACCTAGC**G/A**AGGGAAGGAG (SEQ ID No: 296) |
| | | | mut/mut: f: CTCCTTCCCT**T**GCTAGGTCCT (SEQ ID No: 297) r: AGGACCTAGC**A**AGGGAAGGAG (SEQ ID No: 298) |
| | | | wt/mut: |
| Promoter fragment 2 | 1625 (SNP 41) (only in RCC samples) | f: GGGAATCACT**C**AACCTCTCTG (SEQ ID No: 299) r: CAGAGAGGTT**G**AGTGATTCCC (SEQ ID No: 300) | f: GGGAATCACT**C/A**AACCTCTCTG (SEQ ID No: 301) r: CAGAGAGGTT**G/T**AGTGATTCCC (SEQ ID No: 302) |
| | | | mut/mut: f: GGGAATCACT**A**AACCTCTCTG (SEQ ID No: 303) r: CAGAGAGGTT**T**AGTGATTCCC (SEQ ID No: 304) |
| | Accession number U91318 | | wt/mut: |
| Exon 30 (intron 29) | 17900 (SNP 42) (only in RCC samples) | f: TGTCTCCTTT**C**GCTTCTCCCA (SEQ ID No: 305) r: TGGGAGAAGC**G**AAAGGAGACA (SEQ ID No: 306) | f: TGTCTCCTTT**C/T**GCTTCTCCCA (SEQ ID No: 307) r: TGGGAGAAGC**G/A**AAAGGAGACA (SEQ ID No: 308) |
| | | | mut/mut: f: TGTCTCCTTT**T**GCTTCTCCCA (SEQ ID No: 309) r: TGGGAGAAGC**A**AAAGGAGACA (SEQ ID No: 310) |
| | Accession number AC026452 | | wt/mut: |
| Promoter fragment 1 | 38646 (SNP 32) | f: CCTTAAACAG**G**ATTTGAAAAG (SEQ ID No: 311) r: CTTTTCAAAT**C**CTGTTTAAGG (SEQ ID No: 312) | f: CCTTAAACAG**G/C**ATTTGAAAAG (SEQ ID No: 313) r: CTTTTCAAAT**C/G**CTGTTTAAGG (SEQ ID No: 314) |
| | | | mut/mut: f: CCTTAAACAG**C**ATTTGAAAAG (SEQ ID No: 315) r: CTTTTCAAAT**G**CTGTTTAAGG (SEQ ID No: 316) |
| | Accession number AC025277 | | wt/mut: |
| Exon 5 (intron 5) | 33551 (SNP 36) | f: TGTGACCACA**G**ATGAGTGTGT (SEQ ID No: 317) r: ACACACTCAT**C**TGTGGTCACA (SEQ ID No: 318) | f: TGTGACCACA**G/A**ATGAGTGTGT (SEQ ID No: 319) r: ACACACTCAT**C/T**TGTGGTCACA (SEQ ID No: 320) |
| | | | mut/mut: f: TGTGACCACA**A**ATGAGTGTGT (SEQ ID No: 321) r: ACACACTCAT**T**TGTGGTCACA (SEQ ID No: 322) |

TABLE 3

New SNP's in the gene for MRP1

| Site | SNP | Var. | Pos. | GI no Acc no | Seq ID Forward[1] | Seq ID Reverse[1] | Seq ID IUB_Forward | Seq ID IUB_Reverse |
|---|---|---|---|---|---|---|---|---|
| P3 | mrys546 | a > g | 51798 | 3582311 | 329 TAACCAGGTTgT TGATCCTC | 330 GAGGATCAAcA ACCTGGTTA | 331 TAACCAGGTTrT TGATCCTC | 332 GAGGATCAAyA ACCTGGTTA |
| P1 | mryp282 | g > a | 37971 | 7363401 | 333 TGGGGTGGGGa TGGCGCGGGG | 334 CCCCGCGCCAt CCCCACCCCA | 335 TGGGGTGGGGr TGGCGCGGGG | 336 CCCCGCGCCAy CCCCACCCCA |
| P1 | mryp877 | g > a | 50892 | 3582311 | 337 TGGGCACGCGa CCCCCCACGCA | 338 TGCGTGGGGGG tCGCGTGCCC | 339 TGGGCACGCGr CCCCCCACGCA | 340 TGCGTGGGGGG yCGCGTGCCC |
| E22 | mryo336 | g > a | 55296 | 2815549 | 341 CCATGTGTCCa CGCTGGCTTC | 342 GAAGCCAGCGt GGACACATGG | 343 CCATGTGTCCrC GCTGGCTTC | 344 GAAGCCAGCGy GGACACATGG |
| I 21 | mryo172 | g > a | 55132 | 2815549 | 345 TGAAGCCCCCa ACCTTGTGGG | 346 CCCACAAGGTtG GGGGCTTCA | 347 TGAAGCCCCCrA CCTTGTGGG | 348 CCCACAAGGTy GGGGGCTTCA |
| I 21 | mryo154 | a > g | 55114 | 2815549 | 349 TGGGTGGCACg GTGCTGGTGA | 350 TCACCAGCACc GTGCCACCCA | 351 TGGGTGGCACr GTGCTGGTGA | 352 TCACCAGCACy GTGCCACCCA |
| I 21 | mryo152 | a > g | 55112 | 2815549 | 353 GCTGGGTGGCg CAGTGCTGGT | 354 ACCAAGCACTG cGCCACCCAGC | 355 GCTGGGTGGCr CAGTGCTGGT | 356 ACCAAGCACTG yGCCACCCAGC |
| P1 | mryp522 | delCC CGCCG CCCGG TG | 109 to 122 | 4826837 | 357 GGCCCGATCAC CCGCCGCCG | 358 CGGCGGCGGG TGATCGGGCC | 359 GGCCCGATCAn CCGCCGCCG | 360 CGGCGGCGGG nTGATCGGGCC |
| P1 | myrp491 | delGCC | 76 to 78 | 4826837 | 361 TCCCTGC[GCC]$_{13}$ AGCGCTAGCG | 362 CGCTAGCGCT [GGC]$_{13}$GCA GGGA | 363 TCCCTGC[GCC]$_{13}$ nAGCGCTAGCG | 364 CGCTAGCGCTn [GGC]$_{13}$GCAG GGA |
| P1 | mryp489 | del [GCC]$_2$ | 73 to 78 | 4826837 | 365 TCCCTGC[GCC]$_{12}$ AGCGCTAGCG | 366 CGCTAGCGCT [GGC]$_{12}$GCA GGGA | 367 TCCCTGC[GCC]$_{12}$ nAGCGCTAGCG | 368 CGCTAGCGCTn [GGC]$_{12}$GCAG GGA |
| P1 | myrp486 | del [GCC]$_3$ | 70 to 78 | 4826837 | 369 TCCCTGC[GCC]$_{11}$ AGCGCTAGCG | 370 CGCTAGCGCT [GGC]$_{11}$GCA GGGA | 371 TCCCTGC[GCC]$_{11}$ nAGCGCTAGCG | 372 CGCTAGCGCTn [GCC]$_{11}$GCAG GGA |
| P1 | myrp483 | del [GCC]$_4$ | 67 to 78 | 4826837 | 373 TCCCTGC[GCC]$_{10}$ AGCGCTAGCG | 374 CGCTAGCGCT [GGC]$_{10}$GCA GGGA | 375 TCCCTGC[GCC]$_{10}$ nAGCGCTAGCG | 376 CGCTAGCGCTn GGC]$_{10}$GCAGG GA |
| P1 | myrp474 | del [GCC]$_7$ | 58 to 78 | 4826837 | 377 TCCCTGC[GCC]$_7$ AGCGCTAGCG | 378 CGCTAGCGCT [GGC]$_7$GCAG GGA | 379 TCCCTGC[GCC]$_7$n AGCGCTAGCG | 380 CGCTAGCGCGTn [GGC]$_7$GCAGGG A |
| I 14 | mrzl154 | delAA | 20097 to 20098 | 2815549 | 381 TCAAGCAGAGA GAGAGTGTT | 382 AACACTCTCTCT CTGCTTGA | 383 TCAAGCAGAGn AGAGAGTGTT | 384 AACACTCTCTnC TCTGCTTGA |
| E9 | mrzr176 | c > t | 60357 | 7209451 | 385 CTGGGGCCTTt GTGTCATTCA | 386 TGAATGACACaA AGGCCCCAG | 387 CTGGGGCCTTy GTGTCATTCA | 388 TGAATGACACrA AGGCCCCAG |
| I 7 | mrzs129 | g > a | 61786 | 7209451 | 389 ACACAAGGAGa TGAAGCCGTT | 390 AACGGCTTCAtC TCCTTGTGT | 391 ACACAAGGAGrT GAAGCCGTT | 392 AACGGCTTCAy CTCCTTGTGT |
| I 6 | mrzu272 | insC | 76437/ 76438 | 7209451 | 393 CAGGCCCCCCc AGACCTCAGG | 394 CCTGAGGTCTg GGGGGGCCTG | 395 CAGGCCCCCCn AGACCTCAGG | 396 CCTGAGGTCTn GGGGGGCCTG |
| E 2 | mrzy349 | g > a | 39541 | 7209451 | 397 TACAGTTTTGaT TTTGTTGAG | 398 CTCAACAAAAtC AAAACTGTA | 399 TACAGTTTTGrT TTTGTTGAG | 400 CTCAACAAAAyC AAAACTGTA |

[1]Brackets depict repeats. Numbers indicate how often the sequence in brackets is repeated.

TABLE 4

| AAexchange | ProtAccNo | SeqID Protein mut | SeqID Protein |
|---|---|---|---|
| T731 | GI: 2828206 | 401 TPLNKiKTALG | 402 TPLNKxKTALG |
| A989T | GI: 2828206 | 403 CNHVStLASNY | 404 CNHVSxLASNY |

The invention claimed is:

1. A method of determining whether a human subject is at risk for drug-induced hepatic toxicity, comprising the steps of:

(a) detecting the MRP-1 genotype at a position corresponding to position 11 of SEQ ID NO:171 in the human subject; and (b) (i) based on the detection of a homozygous (C/C) at the position corresponding to position 11 of SEQ ID NO:171 in the human subject determining that the human subject is at risk for drug-induced hepatic toxicity; or (ii) based on the detection of a heterozygous (T/C) or homozygous (T/T) at the position corresponding to position 11 of SEQ ID NO:171 in the human subject determining that the human subject is at decreased risk for drug-induced hepatic toxicity relative to the detection of a homozygous (C/C) at said position.

2. The method of claim 1, wherein the human subject has a disorder caused by multidrug resistance.

3. The method of claim 1, wherein detecting the MRP-1 genotype comprises one or more techniques selected from the group consisting of PCR, ligase chain reaction, restriction digestion, direct sequencing, nucleic acid amplification techniques, and hybridization techniques.

4. An in vitro method for assessing the susceptibility of a human subject to drug-induced hepatic toxicity, (a) detecting the MRP-1 genotype at a position corresponding to position 11 of SEQ ID NO:171 in the human subject; and (b) (i) based on the detection of a homozygous (C/C) at the position corresponding to position 11 of SEQ ID NO:171 in the human subject determining that the human subject has an increased susceptibility to drug-induced hepatic toxicity; or (ii) based on the detection of a heterozygous (T/C) or homozygous (T/T) at the position corresponding to position 11 of SEQ ID NO:171 in the human subject determining that the human subject has a decreased susceptibility to drug-induced hepatic toxicity relative to the detection of a homozygous (C/C) at said position wherein detecting the MRP-1 genotype comprises one or more techniques selected from the group consisting of PCR, restriction digestion, direct sequencing, nucleic acid amplification techniques, and hybridization.

5. The method of claim 1, wherein the human subject has a disorder is associated with caused by drug-induced hepatotoxicity.

* * * * *

SEQUENCE LISTING

<160> NUMBER OF SEQ ID NOS: 406

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
gtagggggct ccgttcacg 19

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
cctggaaggt tgtttttaca gacgg 25

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
tggagactgg cgccgtctg 19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
aaggacagta tccgtcacca gg 22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
catggggttg tgaggattgc ac 22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
tgagattcaa acccgtgagc agc 23

<210> SEQ ID NO 7
<211> LENGTH: 24
<212> TYPE: DNA

-continued

<213> ORGANISM: Artificial Sequence
<220> FEATURE:
<223> OTHER INFORMATION: Description of Artificial Sequence: Primer

<400> SEQUENCE: 7
cttagaaact cattcaccct tggg 24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
gtgacaaggc ttcctaaggc tg 22

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
gattaacatc tgccatctta ccataag 27

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
cctcccccca atcaaaggac c 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11
agctggtttc atgctccagg c 21

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
ctagaagaag gaacttaggg tcaac 25

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
ttccagggcg gtctgttgta g 21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 14 attactttg gtctccactg agc 23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 15
aaaacccaac aactcctgtc ttg 23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
gcatctttcc ctccgggtcc 20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 17
acccagcccc agaatgtgat c 21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
gcacacacac tcatttgtgg tc 22

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 19
gagcagctga ctacttgcta agc 23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Primer -continued

<400> SEQUENCE: 20
cattcattca ttcactcccc acc 23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 21
ctgtcattga ctctcattgc ctaac 25

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 22
agtaacaggc agcactgcca g 21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 23
atctctggca gaccccacaa c 21

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 24
aactgaaaga tcaaagccaa ggag 24

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 25
ccccacgtgt cacaagtcat tc 22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
tgggctggaa atccccacgc 20

<210> SEQ ID NO 27
<211> LENGTH: 20
<212> TYPE: DNA

<213> ORGANISM: Artificial Sequence
<220> FEATURE:
<223> OTHER INFORMATION: Description of Artificial Sequence: Primer

<400> SEQUENCE: 27
gggaggagga gagatctgcg 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 28
tgaaccacag ccggaactgc 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
ggatggatca accggggaag 20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 30
tcagaatccc agatatgcag ccg 23

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 31
tgttgagtga tgggctgatc cc 22

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 32
ccttttaaaa atattcaggt acgcagag 28

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 33
cactgctcct aggatgatga ctc 23

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 34
gagtgtgatc tagaggctgc g 21

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 35
ggggaaaccc ttgaaagtta acc 23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 36
cagccaaggg aaagaaatgc aag 23

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 37
atgcctagcg ccattcgtgc 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 38
gggagcacgg tgggaattcg 20

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 39
gaaggaatgt tgaggccttc agtg 24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 40
gaaaagagac gttgctgctt tcgc 24

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 41
aagtgaggcc ctcctagcag g 21

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 42
tgatagcagc agactcacag cc 22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 43
acactcggcc tgcttctacg 20

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 44
aaggactcct aaaggggaca cg 22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
gctcctggat gctgttatcg c 21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 46
tggctggtgg caacctcaaa g 21

<210> SEQ ID NO 47
<211> LENGTH: 23
<212> TYPE: DNA

<213> ORGANISM: Artificial Sequence
<220> FEATURE:
<223> OTHER INFORMATION: Description of Artificial Sequence: Primer

<400> SEQUENCE: 47
cccttggttt tagcatctgc ctc 23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 48
gggctgaggc cttttttgt tcc 23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 49
tgtgtgcatg tggaaacact ccg 23

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 50
gacaggtgag ttaacataga caagg 25

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 51
tgctggtgaa gcccccgac 19

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 52
gtttggggtc ccacaaaacg c 21

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 53
ctccctgcag tgcctggtc 19

-continued

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 54
ccacactggg gacatggtaa g 21

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 55
agggcagccc ggctctaac 19

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 56
gccggggttt ggctttatac c 21

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 57
ctctctctgg aattactgcg gag 23

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 58
ctgctcctca aactccgtac c 21

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 59
gaaagtcaag tacgcccgct tac 23

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 60
aggtgcacag gatagggtcc 20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 61
ctgagagggt gctctgtatc g 21

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 62
cacttctgca agttgtatgc gctc 24

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 63
gagagggctg tcgagttggg 20

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 64
tcagtgcaat catagggctt gcc 23

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 65
ccagaagtcc ttaggtcgcc 20

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 66
cttcaaacac ccctaccgag atg 23

<210> SEQ ID NO 67
<211> LENGTH: 22
<212> TYPE: DNA

<213> ORGANISM: Artificial Sequence
<220> FEATURE:
<223> OTHER INFORMATION: Description of Artificial Sequence: Primer

<400> SEQUENCE: 67
ggacatgctt tcctggtcaa gc 22

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 68
gggctgtcac tagggataag g 21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 69
gcaaccagct ggaaggtact g 21

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 70
cagaagtctg gctgccaaaa ctc 23

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
gcgtgcccag tcctggggtt t 21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
aaaccccagg actgggcacg c 21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
gcgtgcccag ycctggggtt t 21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
aaaccccagg rctgggcacg c 21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
gcgtgcccag ccctggggtt t 21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
aaaccccagg gctgggcacg c 21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
agccttggag gatctggggt g 21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
caccccagat cctccaaggc t 21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
agccttggag ratctggggt g 21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
caccccagat yctccaaggc t 21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
agccttggag aatctggggt g 21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
caccccagat tctccaaggc t 21

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
actccaggca ggtagggggc tccg 24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
cggagccccc tacctgcctg gagt 24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(14)
<223> OTHER INFORMATION: these nucleotides may not be present

<400> SEQUENCE: 85

-continued actccaggca ggtagggggc tccg 24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(14)
<223> OTHER INFORMATION: these nucleotides may not be present

<400> SEQUENCE: 86
cggagccccc tacctgcctg gagt 24

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
actccaggca gggggctccg 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
cggagccccc tgcctggagt 20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
tgtgatcggc ccgcctcggc t 21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
agccgaggcg ggccgatcac a 21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
tgtgatcggc ycgcctcggc t 21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
agccgaggcg rgccgatcac a 21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
tgtgatcggc tcgcctcggc t 21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
agccgaggcg agccgatcac a 21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
ttaatttttt tattattatt t 21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
aaataataat aaaaaaatta a 21

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (11)..(11)
<223> OTHER INFORMATION: this nucleotide may not be present

<400> SEQUENCE: 97
ttaatttttt ttattattat tt 22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(11)
<223> OTHER INFORMATION: this nucleotide may not be present

<400> SEQUENCE: 98
aaataataat aaaaaaaatt aa 22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
ttaatttttt ttattattat tt 22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
aaataataat aaaaaaaatt aa 22

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 101
ttcctccttc cctcgctagg t 21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
acctagcgag ggaaggagga a 21

<210> SEQ ID NO 103
<211> LENGTH: 28
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(17)
<223> OTHER INFORMATION: these nucleotides may not be present

<400> SEQUENCE: 103
ttcctccttc ctccttccct cgctaggt 28

<210> SEQ ID NO 104
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(17)
<223> OTHER INFORMATION: these nucleotides may not be present

<400> SEQUENCE: 104
acctagcgag gaggaaggga aggaggaa 28

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
ttcctccttc ctccttccct cgctaggt 28

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
acctagcgag ggaaggagga aggaggaa 28

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
tgggggaccc aggccaataa a 21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108

-continued tttattggcc tgggtccccc a 21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
tgggggaccc rggccaataa a 21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
tttattggcc ygggtccccc a 21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
tgggggaccc gggccaataa a 21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
tttattggcc cgggtccccc a 21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
aagagtagca gttttatctt g 21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
caagataaaa ctgctactct t 21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aagagtagca rttttatctt g 21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
caagataaaa ytgctactct t 21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
aagagtagca attttatctt g 21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
caagataaaa ttgctactct t 21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aaaaaaatcc caatccaaaa a 21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tttttggatt gggatttttt t 21

<210> SEQ ID NO 121

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

aaaaaaatcc maatccaaaa a                                              21


<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

tttttggatt kggatttttt t                                              21


<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123

aaaaaaatcc aaatccaaaa a                                              21


<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

tttttggatt tggatttttt t                                              21


<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125

gtttcgttgt gggggtggg a                                               21


<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126

tcccaccccc cacaacgaaa c                                              21


<210> SEQ ID NO 127
<211> LENGTH: 21
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 127
gtttcgttgt rgggggtggg a 21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
tcccaccccc yacaacgaaa c 21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
gtttcgttgt agggggtggg a 21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
tcccaccccc tacaacgaaa c 21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
ccaggccccc cagacctcag g 21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
cctgaggtct gggggcctg g 21

<210> SEQ ID NO 133
<211> LENGTH: 21
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 133
ccaggccccc yagacctcag g 21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134
cctgaggtct rgggggcctg g 21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
ccaggccccc tagacctcag g 21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
cctgaggtct agggggcctg g 21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
cctttccact cctgtggcct c 21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
gaggccacag gagtggaaag g 21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
cctttccact mctgtggcct c 21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
gaggccacag kagtggaaag g 21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
cctttccact actgtggcct c 21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
gaggccacag tagtggaaag g 21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
cctgtggcct caatccagga t 21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
atcctggatt gaggccacag g 21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
cctgtggcct saatccagga t 21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
atcctggatt saggccacag g 21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
cctgtggcct gaatccagga t 21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
atcctggatt caggccacag g 21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
ccaggcagcc ggtgaaggtt g 21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
caaccttcac cggctgcctg g 21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
ccaggcagcc rgtgaaggtt g 21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
caaccttcac yggctgcctg g 21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153
ccaggcagcc agtgaaggtt g 21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
caaccttcac tggctgcctg g 21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
cggtgaaggt tgtgtactcc t 21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
aggagtacac aaccttcacc g 21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
cggtgaaggt ygtgtactcc t 21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
aggagtacac raccttcacc g 21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cggtgaaggt cgtgtactcc t 21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
aggagtacac gaccttcacc g 21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ctcatgagct tcttcttcaa g 21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cttgaagaag aagctcatga g 21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ctcatgagct kcttcttcaa g 21

<210> SEQ ID NO 164
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164

cttgaagaag magctcatga g                                              21


<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

ctcatgagct gcttcttcaa g                                              21


<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166

cttgaagaag cagctcatga g                                              21


<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167

agttcgtgaa tgacacgaag g                                              21


<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

ccttcgtgtc attcacgaac t                                              21


<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169

agttcgtgaa ygacacgaag g                                              21


<210> SEQ ID NO 170
<211> LENGTH: 21
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 170
ccttcgtgtc rttcacgaac t 21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
agttcgtgaa cgacacgaag g 21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ccttcgtgtc gttcacgaac t 21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aaggtagggg acgctgtgcc a 21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tggcacagcg tcccctacct t 21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aaggtagggg rcgctgtgcc a 21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 176
tggcacagcg ycccctacct t 21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
aaggtagggg gcgctgtgcc a 21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
tggcacagcg ccccctacct t 21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
acgctcagag gttcatggac t 21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
agtccatgaa cctctgagcg t 21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
acgctcagag kttcatggac t 21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
agtccatgaa mctctgagcg t 21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
acgctcagag tttcatggac t 21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
agtccatgaa actctgagcg t 21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
ggcagtgggc cgagggagtg g 21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186
ccactccctc ggcccactgc c 21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
ggcagtgggc ygagggagtg g 21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
ccactccctc rgcccactgc c 21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
ggcagtgggc tgagggagtg g 21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 190
ccactccctc agcccactgc c 21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
gccagttgga ctcacttggg g 21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 192
ccccaagtga gtccaactgg c 21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
gccagttgga stcacttggg g 21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
ccccaagtga stccaactgg c 21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
gccagttgga gtcacttggg g 21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
ccccaagtga ctccaactgg c 21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
actctcactc agggcacagc a 21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
tgctgtgccc tgagtgagag t 21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
actctcactc rgggcacagc a 21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
tgctgtgccc ygagtgagag t 21

<210> SEQ ID NO 201

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201

actctcactc ggggcacagc a                                            21


<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202

tgctgtgccc cgagtgagag t                                            21


<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203

gcaggtggcc ctgtgcacat t                                            21


<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204

aatgtgcaca gggccacctg c                                            21


<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205

gcaggtggcc ytgtgcacat t                                            21


<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206

aatgtgcaca rggccacctg c                                            21


<210> SEQ ID NO 207
<211> LENGTH: 21
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 207
gcaggtggcc ttgtgcacat t 21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
aatgtgcaca aggccacctg c 21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ttgccgtcta cgtgaccatt g 21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
caatggtcac gtagacggca a 21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ttgccgtcta ygtgaccatt g 21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
caatggtcac rtagacggca a 21

<210> SEQ ID NO 213
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 213
ttgccgtcta tgtgaccatt g 21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
caatggtcac atagacggca a 21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
tcgttgatca gatctgtctg t 21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
acagacagat ctgatcaacg a 21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 217
tcgttgatca satctgtctg t 21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
acagacagat stgatcaacg a 21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 219
tcgttgatca catctgtctg t 21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 220
acagacagat gtgatcaacg a 21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 221
gattctctcc gagaaaacat c 21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 222
gatgttttct cggagagaat c 21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 223
gattctctcc ragaaaacat c 21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 224
gatgttttct yggagagaat c 21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 225
gattctctcc aagaaaacat c 21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 226
gatgttttct tggagagaat c 21

<210> SEQ ID NO 227
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 227
agtctcacac atgtgcactc ac 22

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
gtgagtgcac atgtgtgaga ct 22

<210> SEQ ID NO 229
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (11)..(12)
<223> OTHER INFORMATION: these nucleotides may not be present

<400> SEQUENCE: 229
agtctcacac atgtgcactc ac 22

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (11)..(12)
<223> OTHER INFORMATION: these nucleotides may not be present

<400> SEQUENCE: 230
gtgagtgcac atgtgtgaga ct 22

<210> SEQ ID NO 231
<211> LENGTH: 20
<212> TYPE: DNA

-continued

<213> ORGANISM: Artificial Sequence
<220> FEATURE:
<223> OTHER INFORMATION: Description of Artificial Sequence: Synthetic oligonucleotide

<400> SEQUENCE: 231
agtctcacac gtgcactcac 20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 232
gtgagtgcac gtgtgagact 20

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 233
catgtgcact gacgtggccg g 21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 234
ccggccacgt cagtgcacat g 21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
catgtgcact sacgtggccg g 21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
ccggccacgt sagtgcacat g 21

<210> SEQ ID NO 237
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 237
catgtgcact cacgtggccg g 21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 238
ccggccacgt gagtgcacat g 21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 239
ggggctgggg ctgggtgcgt g 21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
cacgcaccca gccccagccc c 21

<210> SEQ ID NO 241
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(16)
<223> OTHER INFORMATION: these nucleotides may not be present

<400> SEQUENCE: 241
ggggctgggg ctggggctgg gtgcgtg 27

<210> SEQ ID NO 242
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(16)
<223> OTHER INFORMATION: these nucleotides may not be present

<400> SEQUENCE: 242
cacgcaccca ggccccaccc cagcccc 27

<210> SEQ ID NO 243
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 243
ggggctgggg ctggggctgg gtgcgtg 27

<210> SEQ ID NO 244
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 244
cacgcaccca gccccagccc cagcccc 27

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 245
tgtctaatta tagaaatgga t 21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 246
atccatttct ataattagac a 21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 247
tgtctaatta yagaaatgga t 21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 248
atccatttct rtaattagac a 21

<210> SEQ ID NO 249

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 249
tgtctaatta cagaaatgga t 21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
atccatttct gtaattagac a 21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
ctgggaagtc gtccctgacc c 21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
gggtcaggga cgacttccca g 21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 253
ctgggaagtc rtccctgacc c 21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
gggtcaggga ygacttccca g 21

<210> SEQ ID NO 255
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 255
ctgggaagtc atccctgacc c 21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 256
gggtcaggga tgacttccca g 21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 257
ccatgtcagc gtgacacagg t 21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 258
acctgtgtca cgctgacatg g 21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 259
ccatgtcagc rtgacacagg t 21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 260
acctgtgtca ygctgacatg g 21

<210> SEQ ID NO 261
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 261
ccatgtcagc atgacacagg t 21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
acctgtgtca tgctgacatg g 21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ctggtttttt tcttccggtc a 21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
tgaccggaag aaaaaaacca g 21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (11)..(11)
<223> OTHER INFORMATION: this nucleotide may not be present

<400> SEQUENCE: 265
ctggtttttt tcttccggtc a 21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (11)..(11)
<223> OTHER INFORMATION: this nucleotide may not be present

<400> SEQUENCE: 266
tgaccggaag aaaaaaacca g 21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 267
ctggtttttt cttccggtca 20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 268
tgaccggaag aaaaaaccag 20

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 269
cactggcaca gtggcctcta g 21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 270
ctagaggcca ctgtgccagt g 21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 271
cactggcaca rtggcctcta g 21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 272
ctagaggcca ytgtgccagt g 21

<210> SEQ ID NO 273

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 273
cactggcaca atggcctcta g 21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 274
ctagaggcca ttgtgccagt g 21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 275
cccaaaacac gcacaccctg c 21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 276
gcagggtgtg cgtgttttgg g 21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 277
cccaaaacac rcacaccctg c 21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 278
gcagggtgtg ygtgttttgg g 21

<210> SEQ ID NO 279
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 279
cccaaaacac acacaccctg c 21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 280
gcagggtgtg tgtgttttgg g 21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 281
gtgcactcac gtggccgggt g 21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 282
cacccggcca cgtgagtgca c 21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 283
gtgcactcac rtggccgggt g 21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 284
cacccggcca ygtgagtgca c 21

<210> SEQ ID NO 285
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 285
gtgcactcac atggccgggt g 21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 286
cacccggcca tgtgagtgca c 21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 287
ccacggcagc cgtggacctg g 21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 288
ccaggtccac ggctgccgtg g 21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 289
ccacggcagc ygtggacctg g 21

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 290
ccaggtccac rgctgccgtg g 21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 291
ccacggcagc tgtggacctg g 21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 292
ccaggtccac agctgccgtg g 21

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 293
ctccttccct cgctaggtcc t 21

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 294
aggacctagc gagggaagga g 21

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 295
ctccttccct ygctaggtcc t 21

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 296
aggacctagc ragggaagga g 21

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 297
ctccttccct tgctaggtcc t 21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 298
aggacctagc aagggaagga g 21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 299
gggaatcact caacctctct g 21

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 300
cagagaggtt gagtgattcc c 21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 301
gggaatcact maacctctct g 21

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 302
cagagaggtt kagtgattcc c 21

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 303
gggaatcact aaacctctct g 21

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 304
cagagaggtt tagtgattcc c 21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 305
tgtctccttt cgcttctccc a 21

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 306
tgggagaagc gaaaggagac a 21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 307
tgtctccttt ygcttctccc a 21

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 308
tgggagaagc raaaggagac a 21

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
tgtctccttt tgcttctccc a 21

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 310
tgggagaagc aaaaggagac a 21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 311
ccttaaacag gatttgaaaa g 21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 312
cttttcaaat cctgtttaag g 21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 313
ccttaaacag satttgaaaa g 21

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 314
cttttcaaat sctgtttaag g 21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 315
ccttaaacag catttgaaaa g 21

<210> SEQ ID NO 316
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 316
cttttcaaat gctgtttaag g 21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 317
tgtgaccaca gatgagtgtg t 21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 318
acacactcat ctgtggtcac a 21

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
tgtgaccaca ratgagtgtg t 21

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 320
acacactcat ytgtggtcac a 21

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
tgtgaccaca aatgagtgtg t 21

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
acacactcat ttgtggtcac a 21

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: sequence
      of G57998T (exon 10, Arg433Ser)
<220> FEATURE:
<221> NAME/KEY: CDS
<222> LOCATION: (3)..(20)

<400> SEQUENCE: 323 ac gct cag agt ttc atg gac t 21

Ala Gln Ser Phe Met Asp
1 5

<210> SEQ ID NO 324
<211> LENGTH: 6
<212> TYPE: PRT
<213> ORGANISM: Artificial Sequence
<220> FEATURE:
<223> OTHER INFORMATION: Description of Artificial Sequence: sequence
      of G57998T (exon 10, Arg433Ser)

<400> SEQUENCE: 324

Ala Gln Ser Phe Met Asp
1 5

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: sequence
      of G27258A (exon 17, Arg723Gln)
<220> FEATURE:
<221> NAME/KEY: CDS
<222> LOCATION: (1)..(21)

<400> SEQUENCE: 325 gat tct ctc caa gaa aac atc 21
Asp Ser Leu Gln Glu Asn Ile
1 5

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: sequence
      of G27258A (exon 17, Arg723Gln)

<400> SEQUENCE: 326

Asp Ser Leu Gln Glu Asn Ile
1 5

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: sequence of T249G (exon 8, Phe329Cys)
<220> FEATURE:
<221> NAME/KEY: CDS
<222> LOCATION: (1)..(21)

<400> SEQUENCE: 327 ctc atg agc tgc ttc ttc aag 21
Leu Met Ser Cys Phe Phe Lys
1 5

<210> SEQ ID NO 328
<211> LENGTH: 7
<212> TYPE: PRT
<213> ORGANISM: Artificial Sequence
<220> FEATURE:
<223> OTHER INFORMATION: Description of Artificial Sequence: sequence of T249G (exon 8, Phe329Cys)

<400> SEQUENCE: 328

Leu Met Ser Cys Phe Phe Lys
1 5

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 329
taaccaggtt gttgatcctc 20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 330
gaggatcaac aacctggtta 20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 331
taaccaggtt rttgatcctc 20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 332
gaggatcaay aacctggtta 20

<210> SEQ ID NO 333
<211> LENGTH: 21

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tggggtgggg atggcgcggg g                                            21

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ccccgcgcca tccccacccc a                                            21

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
tggggtgggg rtggcgcggg g                                            21

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ccccgcgcca yccccacccc a                                            21

<210> SEQ ID NO 337
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
tgggcacgcg accccccacg ca                                           22

<210> SEQ ID NO 338
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
tgcgtggggg gtcgcgtgcc ca                                           22

<210> SEQ ID NO 339
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 339
tgggcacgcg rccccccacg ca 22

<210> SEQ ID NO 340
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 340
tgcgtggggg gycgcgtgcc ca 22

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 341
ccatgtgtcc acgctggctt c 21

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 342
gaagccagcg tggacacatg g 21

<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 343
ccatgtgtcc rcgctggctt c 21

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 344
gaagccagcg yggacacatg g 21

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 345
tgaagccccc aaccttgtgg g 21

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 346
cccacaaggt tgggggcttc a 21

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 347
tgaagccccc raccttgtgg g 21

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 348
cccacaaggt ygggggcttc a 21

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
tgggtggcac ggtgctggtg a 21

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 350
tcaccagcac cgtgccaccc a 21

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 351
tgggtggcac rgtgctggtg a 21

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352
tcaccagcac ygtgccaccc a 21

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
gctgggtggc gcagtgctgg t 21

<210> SEQ ID NO 354
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 354
accaagcact gcgccaccca gc 22

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 355
gctgggtggc rcagtgctgg t 21

<210> SEQ ID NO 356
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 356
accaagcact gygccaccca gc 22

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 357
ggcccgatca cccgccgccg 20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
cggcggcggg tgatcgggcc 20

<210> SEQ ID NO 359
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (11)..(24)
<223> OTHER INFORMATION: these nucleotides may not be present

<400> SEQUENCE: 359
ggcccgatca cccgccgccc ggtgcccgcc gccg 34

<210> SEQ ID NO 360
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (11)..(24)
<223> OTHER INFORMATION: these nucleotides may not be present

<400> SEQUENCE: 360
cggcggcggg cagcgggcgg cgggtgatcg ggcc 34

<210> SEQ ID NO 361
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
tccctgcgcc gccgccgccg ccgccgccgc cgccgccgcc gccgccagcg ctagcg 56

<210> SEQ ID NO 362
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 362
cgctagcgct ggcggcggcg gcggcggcgg cggcggcggc ggcggcggcg caggga 56

<210> SEQ ID NO 363
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (47)..(49)
<223> OTHER INFORMATION: these nucleotides may not be present

<400> SEQUENCE: 363
tccctgcgcc gccgccgccg ccgccgccgc cgccgccgcc gccgccgcca gcgctagcg 59

<210> SEQ ID NO 364
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(13)
<223> OTHER INFORMATION: these nucleotides may not be present

<400> SEQUENCE: 364
cgctagcgct ggcggcggcg gcggcggcgg cggcggcggc ggcggcggcg gcgcaggga 59

<210> SEQ ID NO 365
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 365
tccctgcgcc gccgccgccg ccgccgccgc cgccgccgcc gccagcgcta gcg 53

<210> SEQ ID NO 366
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 366
cgctagcgct ggcggcggcg gcggcggcgg cggcggcggc ggcggcgcag gga 53

<210> SEQ ID NO 367
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (44)..(49)
<223> OTHER INFORMATION: these nucleotides may not be present

<400> SEQUENCE: 367
tccctgcgcc gccgccgccg ccgccgccgc cgccgccgcc gccgccgcca gcgctagcg 59

<210> SEQ ID NO 368
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

```
<220> FEATURE:
<221> NAME/KEY: misc_feature
<222> LOCATION: (11)..(16)
<223> OTHER INFORMATION: these nucleotides may not be present

<400> SEQUENCE: 368

cgctagcgct ggcggcggcg gcggcggcgg cggcggcggc ggcggcggcg gcgcaggga      59


<210> SEQ ID NO 369
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369

tccctgcgcc gccgccgccg ccgccgccgc cgccgccgcc agcgctagcg                50


<210> SEQ ID NO 370
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370

cgctagcgct ggcggcggcg gcggcggcgg cggcggcggc ggcgcaggga                50


<210> SEQ ID NO 371
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (41)..(49)
<223> OTHER INFORMATION: these nucleotides may not be present

<400> SEQUENCE: 371

tccctgcgcc gccgccgccg ccgccgccgc cgccgccgcc gccgccgcca gcgctagcg      59


<210> SEQ ID NO 372
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (11)..(19)
<223> OTHER INFORMATION: these nucleotides may not be present

<400> SEQUENCE: 372

cgctagcgct ggcggcggcg gcggcggcgg cggcggcggc ggcggcggcg gcgcaggga      59


<210> SEQ ID NO 373
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
```

tccctgcgcc gccgccgccg ccgccgccgc cgccgccagc gctagcg 47

<210> SEQ ID NO 374
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 374
cgctagcgct ggcggcggcg gcggcggcgg cggcggcggc gcaggga 47

<210> SEQ ID NO 375
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (38)..(49)
<223> OTHER INFORMATION: these nucleotides may not be present

<400> SEQUENCE: 375
tccctgcgcc gccgccgccg ccgccgccgc cgccgccgcc gccgccgcca gcgctagcg 59

<210> SEQ ID NO 376
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (11)..(22)
<223> OTHER INFORMATION: these nucleotides may not be present

<400> SEQUENCE: 376
cgctagcgct ggcggcggcg gcggcggcgg cggcggcggc ggcggcggcg gcgcaggga 59

<210> SEQ ID NO 377
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 377
tccctgcgcc gccgccgccg ccgccgccag cgctagcg 38

<210> SEQ ID NO 378
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 378
cgctagcgct ggcggcggcg gcggcggcgg cgcaggga 38

<210> SEQ ID NO 379
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (29)..(49)
<223> OTHER INFORMATION: these nucleotides may not be present

<400> SEQUENCE: 379
tccctgcgcc gccgccgccg ccgccgccgc cgccgccgcc gccgccgcca gcgctagcg 59

<210> SEQ ID NO 380
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(31)
<223> OTHER INFORMATION: these nucleotides may not be present

<400> SEQUENCE: 380
cgctagcgct ggcggcggcg gcggcggcgg cggcggcggc ggcggcggcg gcgcaggga 59

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 381
tcaagcagag agagagtgtt 20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 382
aacactctct ctctgcttga 20

<210> SEQ ID NO 383
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(12)
<223> OTHER INFORMATION: these nucleotides may not be present

<400> SEQUENCE: 383
tcaagcagag aaagagagtg tt 22

<210> SEQ ID NO 384
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<221> NAME/KEY: misc_feature
<222> LOCATION: (11)..(12)
<223> OTHER INFORMATION: these nucleotides may not be present

<400> SEQUENCE: 384
aacactctct ttctctgctt ga 22

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 385
ctggggcctt tgtgtcattc a 21

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 386
tgaatgacac aaaggcccca g 21

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 387
ctggggcctt ygtgtcattc a 21

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 388
tgaatgacac raaggcccca g 21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 389
acacaaggag atgaagccgt t 21

<210> SEQ ID NO 390
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 390
aacggcttca tctccttgtg t 21

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 391
acacaaggag rtgaagccgt t 21

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 392
aacggcttca yctccttgtg t 21

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 393
caggcccccc cagacctcag g 21

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 394
cctgaggtct gggggggcct g 21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (11)..(11)
<223> OTHER INFORMATION: this nucleotide may not be present

<400> SEQUENCE: 395
caggcccccc cagacctcag g 21

<210> SEQ ID NO 396
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (11)..(11)
<223> OTHER INFORMATION: this nucleotide may not be present

<400> SEQUENCE: 396

cctgaggtct gggggggcct g                                              21

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397

tacagttttg attttgttga g                                              21

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398

ctcaacaaaa tcaaaactgt a                                              21

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399

tacagttttg rttttgttga g                                              21

<210> SEQ ID NO 400
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400

ctcaacaaaa ycaaaactgt a                                              21

<210> SEQ ID NO 401
<211> LENGTH: 11
<212> TYPE: PRT
<213> ORGANISM: Artificial Sequence
<220> FEATURE:
<223> OTHER INFORMATION: Decsription of Artificial Sequence:
      Illustrative peptide

<400> SEQUENCE: 401

Thr Pro Leu Asn Lys Ile Lys Thr Ala Leu Gly
1               5                   10
```

```
<210> SEQ ID NO 402
<211> LENGTH: 11
<212> TYPE: PRT
<213> ORGANISM: Artificial Sequence
<220> FEATURE:
<223> OTHER INFORMATION: Decsription of Artificial Sequence:
      Illustrative peptide
<220> FEATURE:
<221> NAME/KEY: MISC_FEATURE
<222> LOCATION: (6)..(6)
<223> OTHER INFORMATION: Thr or Ile

<400> SEQUENCE: 402

Thr Pro Leu Asn Lys Xaa Lys Thr Ala Leu Gly
1               5                   10


<210> SEQ ID NO 403
<211> LENGTH: 11
<212> TYPE: PRT
<213> ORGANISM: Artificial Sequence
<220> FEATURE:
<223> OTHER INFORMATION: Decsription of Artificial Sequence:
      Illustrative peptide

<400> SEQUENCE: 403

Cys Asn His Val Ser Thr Leu Ala Ser Asn Tyr
1               5                   10


<210> SEQ ID NO 404
<211> LENGTH: 11
<212> TYPE: PRT
<213> ORGANISM: Artificial Sequence
<220> FEATURE:
<223> OTHER INFORMATION: Decsription of Artificial Sequence:
      Illustrative peptide
<220> FEATURE:
<221> NAME/KEY: MISC_FEATURE
<222> LOCATION: (6)..(6)
<223> OTHER INFORMATION: Ala or Thr

<400> SEQUENCE: 404

Cys Asn His Val Ser Xaa Leu Ala Ser Asn Tyr
1               5                   10


<210> SEQ ID NO 405
<211> LENGTH: 15
<212> TYPE: DNA
<213> ORGANISM: Artificial Sequence
<220> FEATURE:
<223> OTHER INFORMATION: Decsription of Artificial Sequence: Synthetic
      oligonucleotide

<400> SEQUENCE: 405

cccgccgccc gggtg                                                   15


<210> SEQ ID NO 406
<211> LENGTH: 14
<212> TYPE: PRT
<213> ORGANISM: Artificial Sequence
<220> FEATURE:
<223> OTHER INFORMATION: Description of Artificial Sequence:
      Illustrative transport family signature motif
<220> FEATURE:
<221> NAME/KEY: MISC_FEATURE
<222> LOCATION: (7)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any hydrophobic amino acid
<220> FEATURE:
<221> NAME/KEY: MISC_FEATURE
```

-continued

```
<222> LOCATION: (12)..(12)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any hydrophobic amino acid

<400> SEQUENCE: 406

Leu Ser Ser Gly Gly Gln Xaa Xaa Xaa Arg Xaa Xaa Xaa Ala
1               5                   10
```